(12) United States Patent
Perkins et al.

(10) Patent No.: US 10,124,066 B2
(45) Date of Patent: Nov. 13, 2018

(54) STABILIZED VANCOMYCIN FORMULATIONS

(71) Applicant: Insmed Incorporated, Bridgewater, NJ (US)

(72) Inventors: Walter Perkins, Pennington, NJ (US); Vladimir Malinin, Plainsboro, NJ (US)

(73) Assignee: INSMED INCORPORATED, Bridgewater, NJ (US)

( * ) Notice: Subject to any disclaimer, the term of this patent is extended or adjusted under 35 U.S.C. 154(b) by 0 days.

(21) Appl. No.: 14/648,203

(22) PCT Filed: Nov. 27, 2013

(86) PCT No.: PCT/US2013/072136
§ 371 (c)(1),
(2) Date: May 28, 2015

(87) PCT Pub. No.: WO2014/085526
PCT Pub. Date: Jun. 5, 2014

(65) Prior Publication Data
US 2015/0314002 A1 Nov. 5, 2015

Related U.S. Application Data

(60) Provisional application No. 61/731,363, filed on Nov. 29, 2012.

(51) Int. Cl.
A61K 47/28 (2006.01)
A61K 38/14 (2006.01)
(Continued)

(52) U.S. Cl.
CPC ............... *A61K 47/28* (2013.01); *A61K 9/10* (2013.01); *A61K 9/127* (2013.01); *A61K 31/575* (2013.01);
(Continued)

(58) Field of Classification Search
CPC ...................................... A61K 47/28
See application file for complete search history.

(56) References Cited

U.S. PATENT DOCUMENTS 3,091,572 A 5/1963 Luedemann et al.
3,136,704 A 6/1964 Charney
(Continued)

FOREIGN PATENT DOCUMENTS

CA 2174803A 1 10/1997
CA 2101241 C 12/1998
(Continued)

OTHER PUBLICATIONS

Supplementary European Search Report for European Application No. 13858844.7, dated Jun. 15, 2016, 4 pages.
(Continued)

*Primary Examiner* — Benjamin J Packard
(74) *Attorney, Agent, or Firm* — Cooley LLP

(57) ABSTRACT

In one aspect, the invention provides a stabilized lipid-based glycopeptide antibiotic composition and a process for producing the same. In another aspect, the invention provides methods for treating a bacterial pulmonary infection by administering to a subject in need thereof a therapeutically effective amount of the stabilized lipid-based glycopeptide antibiotic composition.

20 Claims, 18 Drawing Sheets

Vancomycin

(51) Int. Cl.
- *A61K 31/575* (2006.01)
- *A61K 31/685* (2006.01)
- *A61K 9/127* (2006.01)
- *A61K 47/18* (2017.01)
- *A61K 47/24* (2006.01)
- *A61K 9/10* (2006.01)

(52) U.S. Cl.
CPC .......... *A61K 31/685* (2013.01); *A61K 38/14* (2013.01); *A61K 47/183* (2013.01); *A61K 47/24* (2013.01)

(56) References Cited

U.S. PATENT DOCUMENTS

| | | |
|---|---|---|
| 4,235,871 A | 11/1980 | Paphadjopoulos et al. |
| 4,372,949 A | 2/1983 | Kodama et al. |
| 4,394,448 A | 7/1983 | Szoka, Jr. et al. |
| 4,396,630 A | 8/1983 | Riedl et al. |
| 4,451,447 A | 5/1984 | Kaplan et al. |
| 4,515,736 A | 5/1985 | Deamer |
| 4,522,803 A | 6/1985 | Lenk et al. |
| 4,547,490 A | 10/1985 | Ecanow et al. |
| 4,588,578 A | 5/1986 | Fountain et al. |
| 4,606,939 A | 8/1986 | Frank et al. |
| 4,684,625 A | 8/1987 | Eppstein et al. |
| 4,693,999 A | 9/1987 | Axelsson et al. |
| 4,721,612 A | 1/1988 | Janoff et al. |
| 4,767,874 A | 8/1988 | Shima et al. |
| 4,833,134 A | 5/1989 | Kishimoto et al. |
| 4,857,311 A | 8/1989 | Domb et al. |
| 4,895,452 A | 1/1990 | Yiournas et al. |
| 4,895,719 A | 1/1990 | Radhakrishnan et al. |
| 4,897,384 A | 1/1990 | Janoff et al. |
| 4,933,121 A | 6/1990 | Law et al. |
| 4,952,405 A | 8/1990 | Yau-Young |
| 4,963,367 A | 10/1990 | Ecanow |
| 4,975,282 A | 12/1990 | Cullis et al. |
| 4,981,692 A | 1/1991 | Popescu et al. |
| 5,000,958 A | 3/1991 | Fountain et al. |
| 5,006,343 A | 4/1991 | Benson et al. |
| 5,008,050 A | 4/1991 | Cullis et al. |
| 5,023,087 A | 6/1991 | Yau-Young |
| 5,030,453 A | 7/1991 | Lenk et al. |
| 5,041,278 A | 8/1991 | Janoff et al. |
| 5,049,388 A | 9/1991 | Knight et al. |
| 5,049,389 A | 9/1991 | Radhakrishnan |
| 5,059,421 A | 10/1991 | Loughrey et al. |
| 5,059,591 A | 10/1991 | Janoff et al. |
| 5,077,056 A | 12/1991 | Bally et al. |
| 5,169,637 A | 12/1992 | Lenk et al. |
| 5,178,876 A | 1/1993 | Khokhar et al. |
| 5,192,549 A | 3/1993 | Barenolz et al. |
| 5,211,955 A | 5/1993 | Legros et al. |
| 5,252,339 A | 10/1993 | Cristofori et al. |
| 5,264,618 A | 11/1993 | Felgner et al. |
| 5,269,979 A | 12/1993 | Fountain |
| 5,279,833 A | 1/1994 | Rose |
| 5,316,771 A | 5/1994 | Barenholz et al. |
| 5,320,906 A | 6/1994 | Eley et al. |
| 5,334,761 A | 8/1994 | Gebeyehu et al. |
| 5,401,511 A | 3/1995 | Margalit |
| 5,409,704 A | 4/1995 | Bally et al. |
| 5,415,867 A | 5/1995 | Minchey et al. |
| 5,459,127 A | 10/1995 | Felgner et al. |
| 5,508,269 A | 4/1996 | Smith et al. |
| 5,540,936 A | 7/1996 | Coe et al. |
| 5,543,152 A | 8/1996 | Webb et al. |
| 5,549,102 A | 8/1996 | Lintl et al. |
| 5,569,464 A | 10/1996 | Endo et al. |
| 5,578,320 A | 11/1996 | Janoff et al. |
| 5,580,575 A | 12/1996 | Unger et al. |
| 5,596,982 A | 1/1997 | Blaha-Schnabel |
| 5,610,198 A | 3/1997 | Barry, III et al. |
| 5,614,216 A | 3/1997 | Janoff |
| 5,616,334 A | 4/1997 | Janoff et al. |
| 5,616,341 A | 4/1997 | Mayer et al. |
| 5,631,018 A | 5/1997 | Zalipsky et al. |
| 5,641,662 A | 6/1997 | Debs et al. |
| 5,643,599 A | 7/1997 | Lee et al. |
| 5,662,929 A | 9/1997 | Legace et al. |
| 5,665,383 A | 9/1997 | Grinstaff et al. |
| 5,723,147 A | 3/1998 | Kim et al. |
| 5,736,155 A | 4/1998 | Bally et al. |
| 5,740,966 A | 4/1998 | Blaha-Schnabel |
| 5,741,516 A | 4/1998 | Webb et al. |
| 5,753,613 A | 5/1998 | Ansell et al. |
| 5,756,120 A | 5/1998 | Hersch et al. |
| 5,756,121 A | 5/1998 | Bracken |
| 5,756,353 A | 5/1998 | Debs |
| 5,759,571 A | 6/1998 | Hersch et al. |
| 5,766,627 A | 6/1998 | Sankaram et al. |
| 5,785,987 A | 7/1998 | Hope et al. |
| 5,795,589 A | 8/1998 | Mayer et al. |
| 5,814,335 A | 9/1998 | Webb et al. |
| 5,820,848 A | 10/1998 | Boni et al. |
| 5,823,178 A | 10/1998 | Lloyd et al. |
| 5,837,279 A | 11/1998 | Janoff et al. |
| 5,837,282 A | 11/1998 | Fenske et al. |
| 5,840,702 A | 11/1998 | Bedwell |
| 5,843,473 A | 12/1998 | Woodle et al. |
| 5,849,490 A | 12/1998 | Schonwetter et al. |
| 5,861,159 A | 1/1999 | Pardoll et al. |
| 5,871,710 A | 2/1999 | Bogdanov et al. |
| 5,875,776 A | 3/1999 | Vaghefi |
| 5,883,074 A * | 3/1999 | Boggs .................. C12Q 1/18 514/152 |
| 5,891,468 A | 4/1999 | Martin et al. |
| 5,922,350 A | 7/1999 | Janoff et al. |
| 5,939,096 A | 8/1999 | Clerc et al. |
| 5,945,122 A | 8/1999 | Abra et al. |
| 5,957,389 A | 9/1999 | Wunderlich et al. |
| 5,958,449 A | 9/1999 | Hersch et al. |
| 5,965,549 A | 10/1999 | Purwar et al. |
| 5,972,379 A | 10/1999 | Guo et al. |
| 5,993,850 A | 11/1999 | Sankaram et al. |
| 6,000,394 A | 12/1999 | Blaha-Schnabel et al. |
| 6,045,828 A | 4/2000 | Bystrom et al. |
| 6,051,251 A | 4/2000 | Zalipsky et al. |
| 6,051,549 A | 4/2000 | Roberts et al. |
| 6,085,741 A | 7/2000 | Becker |
| 6,086,851 A | 7/2000 | Boni et al. |
| 6,090,407 A | 7/2000 | Knight et al. |
| 6,106,479 A | 8/2000 | Wunderlich et al. |
| 6,106,858 A | 8/2000 | Ye et al. |
| 6,124,273 A | 9/2000 | Drohan et al. |
| 6,147,060 A | 11/2000 | Zasloff et al. |
| 6,162,462 A | 12/2000 | Bolotin et al. |
| 6,176,237 B1 | 1/2001 | Wunderlich et al. |
| 6,197,333 B1 | 3/2001 | Onyuksel et al. |
| 6,211,162 B1 | 4/2001 | Dale et al. |
| 6,221,385 B1 | 4/2001 | Camu et al. |
| 6,221,388 B1 | 4/2001 | Hersch et al. |
| 6,228,346 B1 | 5/2001 | Zhang et al. |
| 6,228,393 B1 | 5/2001 | DiCosmo et al. |
| 6,235,177 B1 | 5/2001 | Borland et al. |
| 6,274,175 B1 | 8/2001 | Gombotz et al. |
| 6,316,024 B1 | 11/2001 | Allen et al. |
| 6,338,859 B1 | 1/2002 | Leroux et al. |
| 6,348,069 B1 | 2/2002 | Vacanti et al. |
| 6,352,996 B1 | 3/2002 | Cao et al. |
| 6,355,267 B1 | 3/2002 | Collins |
| 6,387,886 B1 | 5/2002 | Montgomery et al. |
| 6,419,901 B2 | 7/2002 | Placke et al. |
| 6,440,393 B1 | 8/2002 | Waldrep et al. |
| 6,443,898 B1 | 9/2002 | Unger et al. |
| 6,447,753 B2 | 9/2002 | Edwards et al. |
| 6,451,784 B1 | 9/2002 | Placke et al. |
| 6,458,373 B1 | 10/2002 | Lambert et al. |
| 6,468,532 B1 | 10/2002 | Hsei et al. |
| 6,475,779 B2 | 11/2002 | Mathiowitz et al. |
| 6,481,438 B1 | 11/2002 | Gallem et al. |
| 6,492,560 B2 | 12/2002 | Wilbur et al. |
| 6,497,901 B1 | 12/2002 | Royer |
| 6,509,323 B1 | 1/2003 | Davis et al. |

(56) References Cited

U.S. PATENT DOCUMENTS

| | | |
|---|---|---|
| 6,511,676 B1 | 1/2003 | Boulikas |
| 6,513,727 B1 | 2/2003 | Jaser et al. |
| 6,518,243 B1 | 2/2003 | Kahne et al. |
| 6,521,211 B1 | 2/2003 | Unger et al. |
| 6,521,736 B2 | 2/2003 | Watterson et al. |
| 6,534,018 B1 | 3/2003 | Baker et al. |
| 6,546,927 B2 | 4/2003 | Litherland et al. |
| 6,554,201 B2 | 4/2003 | Klimowicz et al. |
| 6,596,305 B1 | 7/2003 | Edgerly-Plug |
| 6,599,912 B1 | 7/2003 | Au et al. |
| 6,606,990 B2 | 8/2003 | Stapleton et al. |
| 6,613,352 B2 | 9/2003 | Lagace et al. |
| 6,615,824 B2 | 9/2003 | Power |
| 6,623,671 B2 | 9/2003 | Coe et al. |
| 6,629,646 B1 | 10/2003 | Ivri |
| 6,676,034 B2 | 1/2004 | Tanaka et al. |
| 6,679,251 B1 | 1/2004 | Gallem et al. |
| 6,759,057 B1 | 7/2004 | Weiner et al. |
| 6,770,291 B2 | 8/2004 | Smyth-Templeton et al. |
| 6,843,942 B2 | 1/2005 | Katinger et al. |
| 6,845,770 B2 | 1/2005 | Klimowicz et al. |
| 6,855,296 B1 | 2/2005 | Baker et al. |
| 6,890,555 B1 | 5/2005 | Desai et al. |
| 6,900,184 B2 | 5/2005 | Cohen et al. |
| 6,915,962 B2 | 7/2005 | Power et al. |
| 6,916,490 B1 | 7/2005 | Garver et al. |
| 6,948,491 B2 | 9/2005 | Loeffler et al. |
| 6,962,151 B1 | 11/2005 | Knoch et al. |
| 6,983,747 B2 | 1/2006 | Gallem et al. |
| 6,991,809 B2 | 1/2006 | Anderson |
| 7,059,320 B2 | 6/2006 | Feiner et al. |
| 7,063,860 B2 | 6/2006 | Chancellor et al. |
| 7,077,126 B2 | 7/2006 | Kummer et al. |
| 7,100,600 B2 | 9/2006 | Loeffler et al. |
| 7,104,463 B2 | 9/2006 | Litherland et al. |
| 7,131,440 B2 | 11/2006 | Sonntag |
| 7,244,413 B2 | 7/2007 | Barbera-Guillem |
| 7,252,085 B2 | 8/2007 | Kunschir |
| 7,255,106 B2 | 8/2007 | Gallem et al. |
| 7,297,344 B1 | 11/2007 | Fleischer et al. |
| 7,331,339 B2 | 2/2008 | Smith et al. |
| 7,368,102 B2 | 5/2008 | Tarara et al. |
| D583,928 S | 12/2008 | Knoch |
| 7,458,372 B2 | 12/2008 | Feiner et al. |
| 7,472,701 B2 | 1/2009 | Pfichner et al. |
| 7,544,369 B2 | 6/2009 | Boni et al. |
| 7,600,511 B2 | 10/2009 | Power et al. |
| 7,686,014 B2 | 3/2010 | Boehm et al. |
| 7,718,189 B2 | 5/2010 | Boni et al. |
| 7,748,377 B2 | 7/2010 | Smith et al. |
| 7,758,886 B2 | 7/2010 | Jauernig et al. |
| 7,771,642 B2 | 8/2010 | Power et al. |
| 7,779,838 B2 | 8/2010 | Hetzer et al. |
| 7,879,351 B2 | 2/2011 | Li et al. |
| 7,891,352 B2 | 2/2011 | Gallem et al. |
| 7,931,212 B2 | 4/2011 | Urich et al. |
| D638,117 S | 5/2011 | Eckstein et al. |
| 7,958,887 B2 | 6/2011 | Kelliher et al. |
| 7,971,588 B2 | 7/2011 | Fink et al. |
| 7,980,247 B2 | 7/2011 | Boehm et al. |
| 8,006,698 B2 | 8/2011 | Boehm et al. |
| 8,071,127 B2 | 12/2011 | Cipolla et al. |
| D652,908 S | 1/2012 | Eckstein et al. |
| 8,100,162 B2 | 1/2012 | Joern et al. |
| 8,113,194 B2 | 2/2012 | Boehm et al. |
| 8,119,156 B2 | 2/2012 | Cipolla et al. |
| D656,604 S | 3/2012 | Eckstein et al. |
| 8,226,975 B2 | 7/2012 | Weers |
| 8,263,645 B2 | 9/2012 | Keller |
| 8,268,347 B1 | 9/2012 | Cipolla et al. |
| 8,333,187 B2 | 12/2012 | Gallem et al. |
| 8,342,171 B2 | 1/2013 | Boehm et al. |
| 8,347,878 B2 | 1/2013 | Schuschnig et al. |
| 8,387,895 B2 | 3/2013 | Stangl |
| 8,398,001 B2 | 3/2013 | Borland et al. |
| D680,214 S | 4/2013 | Eckstein et al. |
| 8,414,915 B2 | 4/2013 | Cipolla et al. |
| 8,459,252 B2 | 6/2013 | Gallem et al. |
| 8,511,581 B2 | 8/2013 | Urich et al. |
| 8,596,264 B2 | 12/2013 | Sommer |
| 8,616,195 B2 | 12/2013 | Power et al. |
| 8,632,804 B2 | 1/2014 | Weers |
| 8,642,075 B2 | 2/2014 | Weers |
| 8,671,933 B2 | 3/2014 | Boehm et al. |
| 8,673,348 B2 | 3/2014 | Weers |
| 8,673,349 B2 | 3/2014 | Weers |
| 8,679,532 B2 | 3/2014 | Weers |
| 8,720,432 B2 | 5/2014 | Borgschulte et al. |
| 8,720,435 B2 | 5/2014 | Gallem et al. |
| 8,739,777 B2 | 6/2014 | Kreutzmann et al. |
| 8,802,137 B2 | 8/2014 | Boni et al. |
| 8,852,557 B2 | 10/2014 | Keller et al. |
| 8,985,100 B2 | 3/2015 | Minocchieri et al. |
| 9,016,272 B2 | 4/2015 | Gallem et al. |
| 9,027,548 B2 | 5/2015 | Borgschulte et al. |
| 9,028,864 B2 | 5/2015 | Cipolla et al. |
| 9,046,092 B2 | 6/2015 | Boehm et al. |
| 9,061,303 B2 | 6/2015 | Waldner et al. |
| 9,072,464 B2 | 7/2015 | Haartsen et al. |
| 9,078,897 B1 | 7/2015 | Cipolla et al. |
| 9,084,862 B2 | 7/2015 | Blakey et al. |
| 9,095,676 B2 | 8/2015 | Gallem et al. |
| 9,108,211 B2 | 8/2015 | Ivri |
| 9,114,081 B2 | 8/2015 | Gupta |
| 9,119,783 B2 | 9/2015 | Gupta |
| 9,119,930 B2 | 9/2015 | Kreutzmann et al. |
| 9,149,588 B2 | 10/2015 | Gordon et al. |
| 9,161,963 B2 | 10/2015 | Keller et al. |
| 9,168,556 B2 | 10/2015 | Pumm et al. |
| 9,198,859 B2 | 12/2015 | Keller et al. |
| 9,259,424 B2 | 2/2016 | Cipolla et al. |
| 9,265,900 B2 | 2/2016 | Loenner et al. |
| 9,333,214 B2 | 5/2016 | Gupta |
| 9,402,845 B2 | 8/2016 | Weers |
| 9,511,082 B2 | 12/2016 | Weers |
| 9,549,925 B2 | 1/2017 | Weers |
| 9,549,939 B2 | 1/2017 | Weers |
| 9,724,301 B2 | 8/2017 | Gupta |
| 9,737,555 B2 | 8/2017 | Gupta |
| 9,827,317 B2 | 11/2017 | Boni et al. |
| 9,895,385 B2 | 2/2018 | Eagle et al. |
| 9,925,205 B2 | 3/2018 | Malinin |
| 2001/0006660 A1 | 7/2001 | Legace et al. |
| 2002/0035061 A1 | 3/2002 | Krieger et al. |
| 2002/0052390 A1 | 5/2002 | Ponikau |
| 2002/0086852 A1 | 7/2002 | Cantor et al. |
| 2002/0187105 A1 | 12/2002 | Zou et al. |
| 2003/0039615 A1 | 2/2003 | Katz |
| 2003/0059375 A1 | 3/2003 | Perez-Soler et al. |
| 2003/0096774 A1 | 5/2003 | Gonda et al. |
| 2003/0099697 A1 | 5/2003 | Panzner et al. |
| 2003/0118636 A1 | 6/2003 | Friesen et al. |
| 2003/0138481 A1 | 7/2003 | Zadi |
| 2003/0148964 A1 | 8/2003 | Dunne |
| 2003/0224039 A1 | 12/2003 | Boni et al. |
| 2004/0009126 A1 | 1/2004 | Pilkiewicz et al. |
| 2004/0032037 A1 | 2/2004 | Katinger et al. |
| 2004/0091541 A1 | 5/2004 | Unger |
| 2004/0101553 A1 | 5/2004 | Lee et al. |
| 2004/0142025 A1 | 7/2004 | MacLachlan et al. |
| 2004/0142026 A1 | 7/2004 | Boni et al. |
| 2004/0156888 A1 | 8/2004 | Jensen et al. |
| 2004/0180082 A1 | 9/2004 | Kang et al. |
| 2005/0019926 A1 | 1/2005 | Gonda et al. |
| 2005/0025822 A1 | 2/2005 | Wong et al. |
| 2005/0042341 A1 | 2/2005 | Thomas et al. |
| 2005/0113337 A1 | 5/2005 | Taneja et al. |
| 2005/0214224 A1 | 9/2005 | Weers et al. |
| 2005/0217666 A1 | 10/2005 | Fink et al. |
| 2005/0220752 A1 | 10/2005 | Charmot et al. |
| 2005/0249795 A1 | 11/2005 | Zhang et al. |
| 2006/0062738 A1 | 3/2006 | Hofmann et al. |
| 2006/0067998 A1 | 3/2006 | Kurzrock et al. |
| 2006/0073198 A1 | 4/2006 | Boni et al. |

(56) References Cited

U.S. PATENT DOCUMENTS

| | | |
|---|---|---|
| 2006/0110441 A1 | 5/2006 | Wong et al. |
| 2006/0217603 A1 | 9/2006 | Nagai et al. |
| 2006/0286038 A1 | 12/2006 | Rairkar et al. |
| 2007/0065367 A1 | 3/2007 | Condos et al. |
| 2007/0077290 A1 | 4/2007 | Li et al. |
| 2007/0081963 A1 | 4/2007 | Oh et al. |
| 2007/0105758 A1* | 5/2007 | May .................. A61K 31/7034 514/2.7 |
| 2007/0196461 A1 | 8/2007 | Weers |
| 2007/0267010 A1 | 11/2007 | Fink et al. |
| 2008/0089927 A1 | 4/2008 | Malinin |
| 2008/0108104 A1 | 5/2008 | Eckstein et al. |
| 2008/0131497 A1 | 6/2008 | Perkins et al. |
| 2008/0246472 A1 | 10/2008 | Igney et al. |
| 2009/0104256 A1 | 4/2009 | Gupta |
| 2009/0104257 A1 | 4/2009 | Li et al. |
| 2009/0105126 A1 | 4/2009 | Li et al. |
| 2009/0269396 A1 | 10/2009 | Cipolla et al. |
| 2009/0274754 A1 | 11/2009 | Cipolla et al. |
| 2010/0068257 A1 | 3/2010 | Boni et al. |
| 2010/0196455 A1 | 8/2010 | Malinin |
| 2010/0260829 A1 | 10/2010 | Boni et al. |
| 2011/0064796 A1 | 3/2011 | Cipolla et al. |
| 2011/0150983 A1 | 6/2011 | Cipolla et al. |
| 2011/0159079 A1 | 6/2011 | Li et al. |
| 2011/0256175 A1 | 10/2011 | Hope et al. |
| 2012/0010162 A1 | 1/2012 | Norling |
| 2012/0077786 A1 | 3/2012 | Byron et al. |
| 2012/0192861 A1 | 8/2012 | Surber |
| 2012/0244206 A1 | 9/2012 | Cipolla et al. |
| 2013/0028960 A1 | 1/2013 | Weers |
| 2013/0034534 A1 | 2/2013 | Kroneberg et al. |
| 2013/0052260 A1 | 2/2013 | Weers |
| 2013/0064883 A1 | 3/2013 | Weers |
| 2013/0071468 A1 | 3/2013 | Weers |
| 2013/0071469 A1 | 3/2013 | Weers |
| 2013/0087480 A1 | 4/2013 | Stark et al. |
| 2013/0089598 A1 | 4/2013 | Gupta |
| 2013/0121918 A1 | 5/2013 | Hong et al. |
| 2013/0136788 A1 | 5/2013 | Gupta |
| 2013/0177629 A1 | 7/2013 | Martin et al. |
| 2013/0330400 A1 | 12/2013 | Perkins et al. |
| 2013/0330440 A1 | 12/2013 | Fulgham |
| 2014/0018431 A1 | 1/2014 | Wade et al. |
| 2014/0072620 A1 | 3/2014 | Weers |
| 2014/0248335 A1 | 9/2014 | Malinin |
| 2014/0308304 A1 | 10/2014 | Manoharan et al. |
| 2014/0314835 A1 | 10/2014 | Boni et al. |
| 2014/0371293 A1 | 12/2014 | Brown et al. |
| 2015/0110855 A1 | 4/2015 | Cipolla et al. |
| 2015/0272880 A1 | 10/2015 | Seidel et al. |
| 2015/0283076 A1 | 10/2015 | Cipolla et al. |
| 2015/0283133 A1 | 10/2015 | Gonda et al. |
| 2015/0306173 A1 | 10/2015 | Chen et al. |
| 2015/0328244 A1 | 11/2015 | Eagle et al. |
| 2016/0113927 A1 | 4/2016 | Weers |
| 2016/0120806 A1 | 5/2016 | Cipolla et al. |
| 2016/0143849 A1 | 5/2016 | Gupta |
| 2016/0151402 A1 | 6/2016 | Gupta |
| 2016/0184301 A1 | 6/2016 | Weers |
| 2016/0184302 A1 | 6/2016 | Weers |
| 2016/0271125 A1 | 9/2016 | Boni et al. |
| 2016/0317563 A1 | 11/2016 | Weers |
| 2016/0317564 A1 | 11/2016 | Weers |
| 2016/0354371 A1 | 12/2016 | Weers |
| 2017/0014342 A1 | 1/2017 | Li et al. |
| 2017/0087155 A1 | 3/2017 | Weers |
| 2017/0100420 A1 | 4/2017 | Boni et al. |
| 2017/0165374 A1 | 6/2017 | Perkins et al. |
| 2017/0196900 A1 | 7/2017 | Perkins et al. |
| 2017/0360816 A1 | 12/2017 | Eagle et al. |
| 2017/0360818 A1 | 12/2017 | Gupta |
| 2018/0104345 A1 | 4/2018 | Boni et al. |

FOREIGN PATENT DOCUMENTS

| | | | |
|---|---|---|---|
| CA | 2215716 C | | 12/1999 |
| CA | 2614764 | | 1/2007 |
| CA | 2838111 | | 6/2007 |
| CN | 1747738 | | 3/2006 |
| EP | 0069307 | | 1/1983 |
| EP | 0274431 | | 5/1994 |
| EP | 0652008 | | 5/1995 |
| EP | 1083881 | | 3/2001 |
| EP | 1083886 | | 3/2001 |
| EP | 1190705 | | 3/2002 |
| EP | 1332755 A1 | | 8/2003 |
| EP | 0825852 | | 7/2004 |
| EP | 1559431 A1 | | 8/2005 |
| EP | 2457609 | | 5/2012 |
| GB | 2145107 | | 3/1985 |
| JP | S63-500175 | | 1/1988 |
| JP | S63-239213 | | 10/1988 |
| JP | 6-345663 | | 12/1994 |
| JP | H10-511363 | | 11/1998 |
| JP | 11-080022 | | 3/1999 |
| JP | 2006-028069 | | 2/2006 |
| JP | 2006-514016 | | 4/2006 |
| JP | 2006-514682 | | 5/2006 |
| UA | 27298 | | 10/2007 |
| UA | 27804 | | 11/2007 |
| WO | WO 85/00968 | | 3/1985 |
| WO | WO 86/06959 | | 12/1986 |
| WO | WO 87/00043 | | 1/1987 |
| WO | WO 87/02219 | | 4/1987 |
| WO | WO 88/04573 | | 6/1988 |
| WO | WO 91/09616 | | 7/1991 |
| WO | WO 91/16882 | | 11/1991 |
| WO | WO 93/12240 | | 6/1993 |
| WO | WO 94/12155 | | 6/1994 |
| WO | WO 94/12156 | | 6/1994 |
| WO | WO 94/22430 | | 10/1994 |
| WO | WO 96/08235 | | 3/1996 |
| WO | WO 96/19199 | | 6/1996 |
| WO | WO 96/19972 | | 7/1996 |
| WO | WO 1996/037194 A1 | | 11/1996 |
| WO | WO 97/29851 | | 8/1997 |
| WO | WO 99/30686 | | 6/1999 |
| WO | WO 99/51202 | | 10/1999 |
| WO | WO 99/61003 | | 12/1999 |
| WO | WO 99/65466 | | 12/1999 |
| WO | WO 00/27359 | | 5/2000 |
| WO | WO 00/29103 | | 5/2000 |
| WO | WO 00/45791 | | 8/2000 |
| WO | WO 01/00173 | | 1/2001 |
| WO | WO 01/05373 | | 1/2001 |
| WO | WO 01/15678 | | 3/2001 |
| WO | WO 01/18280 | | 3/2001 |
| WO | WO 01/32246 | | 5/2001 |
| WO | WO 2002/032400 | | 4/2002 |
| WO | WO 2002/043699 | | 6/2002 |
| WO | WO 2003/045965 | | 6/2003 |
| WO | WO 2003/075889 | | 9/2003 |
| WO | WO 2003/075890 | | 9/2003 |
| WO | WO 2004/002453 | | 1/2004 |
| WO | WO 2004/047802 | | 6/2004 |
| WO | WO 2004/054499 | | 7/2004 |
| WO | WO 2004/091623 A1 | | 10/2004 |
| WO | WO 2004/110346 | | 12/2004 |
| WO | WO 2004/110493 | | 12/2004 |
| WO | WO 2006/108556 | | 10/2006 |
| WO | WO 2007/011940 | | 1/2007 |
| WO | WO 2007/012191 | | 2/2007 |
| WO | WO 2007/067520 | | 6/2007 |
| WO | WO 2007/117509 A2 | | 10/2007 |
| WO | WO 2007/117550 | | 10/2007 |
| WO | WO 2008/039989 | | 4/2008 |
| WO | WO 2008/063341 | | 5/2008 |
| WO | WO 2008/137717 | | 11/2008 |
| WO | WO 2008/137917 | | 11/2008 |
| WO | WO 2009/045116 | | 4/2009 |
| WO | WO 2009/055571 | | 4/2009 |
| WO | WO 2009055568 A2 * | 4/2009 | ........... A61K 9/0078 |

(56) References Cited

FOREIGN PATENT DOCUMENTS

| WO | WO 2009126502 A2 * | 10/2009 | ............ A61K 38/14 |
|---|---|---|---|
| WO | WO 2010/045209 | 4/2010 | |
| WO | WO 2010/111641 | 9/2010 | |
| WO | WO 2011/050206 | 4/2011 | |
| WO | WO 2012/050945 | 4/2012 | |
| WO | WO 2012/069531 | 5/2012 | |
| WO | WO 2012/159103 A1 | 11/2012 | |
| WO | WO 2013/177226 | 11/2013 | |
| WO | WO 2014/052634 | 4/2014 | |
| WO | WO 2014/085526 A1 | 6/2014 | |
| WO | WO 2015/017807 | 2/2015 | |
| WO | WO 2015/175939 | 11/2015 | |
| WO | WO 2017/008076 | 1/2017 | |

OTHER PUBLICATIONS

International Search Report and Written Opinion for International Application No. PCT/US2013/072136, dated Feb. 12, 2014, 15 pages.
First Office Action and Search Report for Chinese Application No. 201380068974.7, dated Sep. 20, 2016, 8 pages.
Levy, D. E. et al., "PEGylated iminodiacetic acid zinc complex stabilizes cationic RNA-bearing nanoparticles," Bioorganic & Medicinal Chemistry Letters, 20:5499-5501 (Jul. 2010).
Extended European Search Report for European Application No. 17207115.1, dated Jun. 1, 2018, 10 pages.
Novosad, S. et al., "The Challenge of Pulmonary Nontuberculous Mycobacterial Infection," Curr Pulmonol Rep. Sep. 1, 2015; 4(3): 152-161. doi:10.1007/s13665-015-0119-3.
Harris, C. M. et al., "The stabilization of vancomycin by peptidoglycan analogs," J Antibiot (Tokyo). Jan. 1985;38(1):51-57.
Takeuchi, Y. et al., "Stabilizing effects of some amino acids on membranes of rabbit erythrocytes perturbed by chlorpromazine," J Pharm Sci. Jan. 1989;78(1):3-7.
U.S. Appl. No. 60/748,468, filed Dec. 8, 2005, Nicholson et al.
International Search Report and Written Opinion for International Application No. PCT/US2008/062469, dated Sep. 18, 2008, 9 pages.
International Preliminary Report on Patentability for International Application No. PCT/US2008/062469, dated Nov. 10, 2009, 7 pages.
International Search Report and Written Opinion for International Application No. PCT/US2008/062868, dated Sep. 18, 2008, 7 pages.
International Preliminary Report on Patentability for International Application No. PCT/US2008/062868, dated Nov. 10, 2009, 5 pages.
Supplementary European Search Report for European Application No. 09821103.0, dated Aug. 12, 2015, 10 pages.
Written Opinion for International Application No. PCT/US2009/060468, dated Jun. 24, 2010, 3 pages.
International Preliminary Report on Patentability for International Application No. PCT/US2009/060468, dated Apr. 19, 2011, 4 pages.
Supplementary European Search Report for European Application No. 03816990.0, dated Jan. 12, 2009, 5 pages.
International Search Report for International Application No. PCT/US2003/034240, dated Jul. 12, 2005, 1 page.
International Preliminary Report on Patentability for International Application No. PCT/US2003/034240, dated May 6, 2013, 5 pages.
Supplementary European Search Report for European Application No. 06787716.7, dated Dec. 29, 2011, 7 pages.
Generics [UK] Ltd.'s Notice of Opposition for European Application No. 06787716.7, filed Jun. 4, 2014, 17 pages.
Patentee's Response to Notice of Opposition and Declaration of Lee Leserman for European Application No. 06787716.7, filed Jan. 16, 2015, 58 pages.
International Search Report and Written Opinion for International Application No. PCT/US2006/027859, dated Aug. 14, 2007, 8 pages.
International Preliminary Report on Patentability for International Application No. PCT/US2006/027859, dated Jan. 22, 2008, 6 pages.
Supplementary European Search Report for European Application No. 07754853, dated Jan. 16, 2013, 8 pages.
International Search Report and Written Opinion for International Application No. PCT/US2007/008404, dated Sep. 26, 2008, 6 pages.
International Preliminary Report on Patentability for International Application No. PCT/US2007/008404, dated Oct. 21, 2008, 4 pages.
European Search Report for European Patent Application No. 11159754.8, dated Jun. 22, 2011, 5 pages.
European Search Report for European Patent Application No. 13175824.5, dated Sep. 16, 2013, 8 pages.
European Search Report for European Application No. 14183066.1, dated Dec. 16, 2014, 11 pages.
Supplementary European Search Report for European Application No. 06847502.9, dated Dec. 5, 2012, 7 pages.
International Search Report and Written Opinion for International Application No. PCT/US2006/046360, dated Oct. 17, 2007, 5 pages.
International Preliminary Report on Patentability for International Application No. PCT/US2006/046360, dated Jun. 11, 2008, 5 pages.
European Search Report for European Application No. 16156100.6, dated Jul. 25, 2016, 6 pages.
European Search Report for European Application No. 16156099.0, dated Jul. 25, 2016, 7 pages.
Supplementary European Search Report and Written Opinion for European Application No. 07754936.8, dated Jan. 18, 2013, 9 pages.
International Search Report and Written Opinion for International Application No. PCT/US2007/008500, dated Sep. 26, 2008, 9 pages.
International Preliminary Report on Patentability for International Application No. PCT/US2007/008500, dated Oct. 21, 2008, 8 pages.
Supplementary European Search Report for European Application No. 13793204.2, dated Sep. 25, 2015, 5 pages.
International Search Report and Written Opinion for International Application No. PCT/US2013/042113, dated Sep. 4, 2013, 13 pages.
International Preliminary Report on Patentability for International Application No. PCT/US2013/042113, dated Nov. 25, 2014, 9 pages.
International Search Report and Written Opinion for International Application No. PCT/US2015/031079, dated Aug. 5, 2015, 9 pages.
Extended European Search Report for European Application No. 15791964.8, dated Dec. 11, 2017, 10 pages.
International Search Report and Written Opinion for International Application No. PCT/US2016/041776, dated Sep. 16, 2016, 9 pages.
International Search Report and Written Opinion for International Application No. PCT/US2016/062894, dated Jan. 31, 2017, 10 pages.
United States Patent and Trademark Office, Before the Patent Trial and Appeal Board, *Aradigm Corporation v. Insmed Incorporated*, Case PGR2017-00021; U.S. Pat. No. 9,402,845, Petition for Post Grant Review, filed May 1, 2017, 111 pages.
United States Patent and Trademark Office, Before the Patent Trial and Appeal Board, *Aradigm Corporation v. Insmed Incorporated*, Case PGR2017-00021; U.S. Pat. No. 9,402,845, Declaration of A. Bruce Montgomery, M.D. dated May 1, 2017, Aradigm Exhibit 1020, 146 pages.
United States Patent and Trademark Office, Before the Patent Trial and Appeal Board, *Aradigm Corporation v. Insmed Incorporated*, Case PGR2017-00021; U.S. Pat. No. 9,402,845, Patent Owner's Preliminary Response, filed Aug. 16, 2017, 84 pages.
United States Patent and Trademark Office, Before the Patent Trial and Appeal Board, *Aradigm Corporation v. Insmed Incorporated*,

(56) References Cited

OTHER PUBLICATIONS

Case PGR2017-00021; U.S. Pat. No. 9,402,845, Declaration of Robert J. Lee, Ph.D. In Support of Patent Owner Insmed's Preliminary Response, dated Aug. 16, 2017, 92 pages.
Amikacin—DrugBank Accession No. DB00479 (APRD00550) [online], <https://www.drugbank.ca/drugs/DB00479>, Retrieved on Apr. 14, 2017, 10 pages.
The Asthma Center Education and Research Fund, Nebulizer Instructions [online], <http://www.theasthmacenter.org/index.php/disease_information/asthma/using_special_devices/nebulizer_instructions/>. Retrieved on Apr. 14, 2017, 1 page.
Ciprofloxacin—DrugBank, Accession No. DB00537 (APRD00424, EXPT00999) [online], <https://www.drugbank.ca/drugs/DB00537>. Retrieved on Apr. 14, 2017, 19 pages.
Prosecution history for U.S. Pat. No. 9,402,845, issued Aug. 2, 2016 (excerpted), 430 pages.
Allen, T. M. et al., "Effect of liposome size and drug release properties of pharmacokinetics of encapsulated drug to rats," The Journal of Pharmacology and Experimental Therapeutics, 226(2):539-544 (1983).
Alton et al., "Cationic lipid-mediated CFTR gene transfer to the lungs and nose of patients with cystic fibrosis: a double-blind placebo-controlled trial," The Lancet, 353(9157):947-954 (1999).
Anacona et al., "Synthesis and antibacterial activity of metal complexes of ciprofloxacin," Transition Metal Chemistry (2001) 26:228-231.
Andrews, J. M., "Determination of minimum inhibitory concentrations," Journal of Antimicrobial Chemotherapy, 48(S1):5-14 (2001).
Antos, M. et al., "Antibacterial activity of liposomal amikacin against Pseudomonas aeruginosa in vitro," Pharmacological Research, 32(1/2):84-87 (1995).
Bakker-Woudenberg, I. et al., "Efficacy of gentamicin or ceftazidine entrapped in liposomes with prolonged blood circulation and enhanced localization in Klebsiella pneumoniae-infected lung tissue," The Journal Infectious Diseases, 171:938-947 (1995).
Bakker-Woudenberg, I. A. J. M. et al., "Long-Circulating Sterically Stabilized Liposomes in the Treatment of Infections," Method in Enzymology, Available online Feb. 21, 2005, 391:228-260 (2005).
Bakker-Woudenberg et al. (2002). Ciprofloxacin in polyethylene glycol-coated liposomes: efficacy in rat models of acute or chronic Pseudomonas aeruginosa infection. Antimicrobial Agents and Chemotherapy 46(8):2575-2581.
Bakker-Woudenberg et al. (2001). Improved efficacy of ciprofloxacin administered in polyethylene glycol-coated liposomes for treatment of Klebsiella pneumoniae pneumonia in rats. Antimicrobial Agents and Chemotherapy 45(5), pp. 1487-1492.
Ball, V. et al., "Complexation mechanism of bovine serum albumin and poly(allylamine hydrochloride)," J. Phys. Chem. B., 106(9):2357-2364 (2002).
Bangham, A. D. et al., "Diffusion of univalent ions across the lamellae of swollen phospholipids," J. Mol. Biol., 13(1):238-252 (1965).
Bangham, A. D., Introduction, "Liposomes: An Historical Perspective," in: Liposomes, Ostro, M. J. (ed.), pp. 1-25, Marcel Dekker, Inc., New York (1983).
Bargoni, A. et al., "Transmucosal transport of tobramycin incorporated in solid lipid nanoparticles (SLN) after duodenal administration to rats. Part II—Tissue distribution," Pharmacological Research, 43(5):497-502 (2001).
Beaulac, C. et al., "Eradication of Mucoid Pseudomonas aeruginosa with Fluid Liposome-Encapsulated Tobramycin in an Animal Model of Chronic Pulmonary Infection," Antimicrobial Agents and Chemotherapy, 40(3):665-669 (1996).
Beaulac, C. et al., "In-vitro bactericidal efficacy of sub-MIC concentrations of liposome-encapsulated antibiotic against Gram-negative and Gram-positive bacteria," Journal of Antimicrobial Chemotherapy, 41:35-41 (1998).
Beaulac, C. et al., "Aerolization of low phase transition temperature liposomal tobramycin as a dry powder in an animal model of chronic pulmonary infection caused by Pseudomonas aeruginosa," Journal Drug Targeting, 7(1):33-41 (1999).
Beaulac, C. et al., "In vitro kinetics of drug release and pulmonary retention of microencapsulated antibiotic in liposomal formulations in relation to the lipid composition," Journal Microencapsulation 14(3):335-348 (1997).
Bedard et al. (1989). Interaction of the fluoroquinolone antimicrobial agents ciprofloxacin and enoxacin with liposomes. Antimicrobial Agents and Chemotherapy 33(8), pp. 1379-1382.
Bermudez, L. E. et al., "Treatment of disseminated mycobacterium avium complex infection of beige mice with liposome-encapsulated aminoglycosides," The Journal of Infectious Diseases, 161(6):1262-1268 (1990).
Betageri et al., Liposome Drug Delivery Systems, (Technomic Publishing Co. ed., 1993) (excerpted).
Bhavane, R. et al., "Agglomerated vesicle technology: a new class of particles for controlled and modulated pulmonary drug delivery," Journal of Controlled Release 93(1):15-28 (Nov. 2003).
Bhavane (2006). Nanoparticle agglomerates for pulmonary drug delivery. A dissertation presented to the faculty of the University of Texas Health Science Center at Houston of Health Information Sciences. UMI No. 3237380.
Biller, J. A. et al., "Efficacy of Liposomal Amikacin for Inhalation (LAI) in Achieving Nontuberculous Mycobacteria (NTM) Culture Negativity in Patients Whose Lung Infection Is Refractory to Guideline-Based Therapy," Poster presented at the ATS 2015 International Conference, May 15-20, 2015, Denver, CO, USA, 1 page.
Biller, J. A. et al., "Efficacy of Liposomal Amikacin for Inhalation (LAI) in Achieving Nontuberculous Mycobacteria (NTM) Culture Negativity in Patients Whose Lung Infection Is Refractory to Guideline-Based Therapy," Abstract, D108 Diagnosis and Management of Nontuberculous Mycobacteria Infections, Poster Discussion Session, May 20, 2015, Colorado Convention Center, Am J Respir Crit Care Med 191;2015:A6295, Online Abstracts Issue, 1 page.
Bilodeau, M. et al., "Kanamycin aerosol therapy in 200 cases of bronchopulmonary suppurations," Can. Med. Assoc. J., 89:537-541 (1963) (with English Abstract).
Blaser, J. et al., "Once daily dosing of aminoglycosides," Eur. Clin. Microbiol. Infect. Dis., 14(12):1029-1038 (1995).
Bolotin, E. M. et al., "Ammonium Sulfate Gradients for Efficient and Stable Remote Loading of Amphipathic Weak Bases into Liposomes and Ligandoliposomes," Journal of Liposome Research, vol. 4(1), 1994, pp. 455-479.
Bruinenberg, P. et al., "Inhaled Liposomal Ciprofloxacin: Once a Day Management of Respiratory Infections," Respiratory Drug Delivery, 1:73-82 (2010).
Bruinenberg, P., "Safety, tolerability and pharmacokinetics of novel liposomal ciprofloxacin of novel liposomal ciprofloxacin formulations for inhalation in healthy volunteers and in non-cystic bronchiectasis patients," Am. J. Respir. Crit. Care Med. (2010) 181:A3192.
Bucke, W. E. et al., "Surface-modified amikacin-liposomes: organ distribution and interaction with plasma proteins," Journal of Drug Targeting, 5(2):99-108 (1997).
Bunderberg de Jong, H. G. et al., Koazevation (Entmischung in Kolloidalen Systemen), Koll, Zeitsch, 50(10):39-48 (1930).
Cabanes et al., "Sustained release of liposome-encapsulated enrofloxacin after intramuscular administration in rabbits," American Journal of Veterinary Research, 56(11):1498-501 (1995).
Cantin, A. M. et al., "Aerosolized prolastin suppresses bacterial proliferation in a model of chronic pseudomonas aeruginosa lung infection," Am. J. Respir. Crit. Care Med., 160:1130-1135 (1999).
Carlier, M. B. et al., "Inhibition of lysosomal phospholipases by aminoglycoside antibiotics: in vitro comparative studies," Antimicrobial Agents and Chemotherapy, 23(3):440-449 (1983).
Carter, G., "Characterization of biofilm formation by *Mycobacterium avium* strains," J. Med. Microbial. (2003) 52:747-52.
Cash, H. A. et al., "A rat model of chronic respiratory infection with Pseudomonas aeruginosa," American Review of Respiratory Disease, 119(3):453-459 (1979).
Challoner, P. B. et al., "Gamma Scintigraphy Lung Deposition Comparison of TOBI in the PARI LC PLUS Nebulizer and the

(56) References Cited

OTHER PUBLICATIONS

Aerodose Inhaler," American Thoracic Society 97th International Conference, San Francisco, California, Aerogen, Inc. (2001).
Chambless, J. D. et al., "A three-dimensional computer model of four hypothetical mechanisms protecting biofilms from antimicrobials," Appl. Environ. Microbiol., 72(3):2005-2013 (2006).
Chan, C. H. S. et al., "Mycobacteria as a cause of infective exacerbation in bronchiectasis," Postgrad. Med. J., 68:896-899 (1992).
Chapman, D., "Physicochemical Properties of Phospholipids and Lipid-Water Systems," In: Liposome Technology, Chapter 1, vol. I, Preparation of Liposomes, Gregoriadis G. (ed.), CRC Press, Inc., Boca Raton, Florida, pp. 1-18 (1984).
Chmiel, J. F. et al., "State of the art: why do the lungs of patients with cystic fibrosis become infected and why can't they clear the infection?", Respiratory Research, 4:8-20 (2003).
Chono, S, et al., "Influence of particle size on drug delivery to rat alveolar macrophages following pulmonary administration of ciprofloxacin incorporated into liposomes," Journal of Drug Targeting, 14(8):557-566 (2006).
Chuchalin et al., "A formulation of aerosolized tobramycin (Bramitob) in the treatment of patients with cystic fibrosis and Pseudomonas aeruginosa infection: a double-blind, placebo-controlled, multicenter study," Paediatric Drugs, 9(Suppl. 1), pp. 21-31, 2007.
Ciofu, O. et al., "Occurrence of Hypermutable Pseudomonas aeruginosa in Cystic Fibrosis Patients Is Associated with the Oxidative Stress Caused by Chronic Lung Inflammation," Antimicrobial Agents and Chemotherapy, 49(6):2276-2282 (Jun. 2005).
Cipro® Products FDA Approval Letter (Mar. 2004), 4 pages.
Cipro® I.V. Label (Jan. 2005), 26 pages.
Cipolla, D., "Development and Characterization of an In Vitro Release Assay for Liposomal Ciproftoxacin for Inhalation," J. Pharm. Sci., 103(1):314-327 (2014).
Cipolla, D., "Liposomal Formulations for Inhalation," Ther. Deliv., 4(8):1047-1072 (2013).
Cipolla, D. et al., "Development of Liposomal Ciprofloxacin to Treat Lung Infections," Pharmaceutics 2016, vol. 8, No. 1, doi:10. 3390/pharmaceutics 8010006.
Cipolla et al., "Assessment of aerosol delivery systems for recombinant human deoxyribonuclease," S.T.P. Pharma Sciences, 4(1), pp. 50-62 (1994).
Clancy, J. P. et al., "Phase II studies of nebulised Arikace in CF patients with Pseudomonas aeruginosa infection," Thorax, 68(9):818-825 (2013).
Clay. M. M. et al., "Assessment of jet nebulisers for lung aerosol therapy," Lancet, 2:592-594 (1983).
ClinicalTrials.gov, "Safety and Efficacy Study of Ciprofloxacin for Inhalation in Patients With Non-Cystic Fibrosis Bronchiectasis 'ORBIT-1'", Identifier: NCT00889967, First Received: Apr. 27, 2009, 3 pages.
Colardyn, F., "The efficacy and safety of isepamicin and ceftazidime compared with amikacin and ceftazidime in acute lower respiratory tract infection," Journal of Chemotherapy, 7(2):129-135 (1995).
Coleman, L. T. et al., "Bronchiectasis in children," Journal of Thoracic Imaging, 10(4)268-279 (1995).
Comis, R. L., "Carboplatin in the treatment of non-small cell lung cancer: a review," Oncology, 50(2):37-41 (1993).
Conley et al., "Aerosol Delivery of Liposome-Encapsulated Ciprofloxacin: Aerosol Characterization and Efficacy against Francisella tularensis Infection in Mice," Antimicrobial Agents and Chemotherapy, 41(6):1288-1292 (Jun. 1997).
Cooksey, R. C. et al., "Antimicrobial susceptibility patterns of *Streptococcus pneumoniae*," Antimicrobial Agents and Chemotherapy, 13(4):645-648 (1978).
Costerton, J. W. et al., "Bacterial biofilms: A common cause of persistent infections," Science, 284:1318-1322 (1999).
Cremades, M. J. et al., "Repeated pulmonary infection by Nocardia asteroides complex in a patient with bronchiectasis," Respiration, 65:211-213 (1998).
Crowther, N. R. et al., "Inhaled aminoglycoside (gentamicin) in bronchiectasis: Dry powder vs. nebulization vs. intravenous therapy," Clinical and Investigative Medicine, Annual Meeting of the Canadian Society for Clinical Investigation, The Royal College of Physicians and Surgeons of Canada and Participating Societies, Toronto, Canada, Abstract 530 (Sep. 24-27, 1998).
Cullis et al., "Liposomes as Pharmaceuticals," Liposomes From Biophysics to Therapeutics, pp. 39-72 (M. Ostro ed., 1987).
Cullis et al., "Generating and loading of liposomal systems for drug delivery applications," Advanced Drug Delivery Reviews, 3, pp. 267-282 (1989).
Currie, D. C., "Nebulisers for bronchiectasis," Thorax, 52(Suppl. 2):S72-S74 (1997).
British Thoracic Society Nebuliser Project Group, Thorax, 1997, vol. 52 (Suppl. 2), S1-S24.
Cymbala, A. A. et al., "The Disease-Modifying Effects of Twice-Weekly Oral Azithromycin in Patients with Bronchiectasis," Treat Respir. Med. 2005;4(2):117-122.
Cynamon, M. H. et al., "Liposome-Encapsulated-Amikacin Therapy of *Mycobacterium avium* Complex Infection in Geige Mice," Antimicrobial Agents and Chemotherapy, 33(8):1179-1183 (1989).
Dally, M. B. et al., "Ventilatory effects of aerosol gentamicin," Thorax, 33:54-56 (1978).
Damaso, D. et al., "Susceptibility of current clinical isolates of Pseudomonas aeruginosa and enteric gram-negative bacilli to amikacin and other aminoglycoside antibiotics," The Journal of Infectious Diseases, 134:S394-S390 (1976).
Deamer, D. W. et al., "Liposome Preparation: Methods and Mechanisms," Chapter 1 in: Liposomes, Ostro, M. J. (ed.), Marcel Dekker, Inc., New York (1983), 27 pages.
Dees, C. et al., "The mechanism of enhanced intraphagocytic killing of bacteria by liposomes containing antibiotics," Veterinary Immunology and Immunopathology, 24:135-146 (1990).
Del Porto, P. et al., "Dysfunctional CFTR alters the bactericidal activity of human macrophages against Pseudomonas aeruginosa," PLoS ONE, 6(5):e19970 (2011).
Demaeyer, P. et al., "Disposition of liposomal gentamicin following intrabronchial administration in rabbits," Journal Microencapsulation, 10(1):77-88 (1993).
Deol, P. et al., "Lung specific stealth liposomes: stability, biodistribution and toxicity of liposomal antitubular drugs in mice," Biochimica et Biophysica Acta, 1334:161-172 (1997).
Dequin, P. F. et al., "Urinary excretion reflects lung deposition of aminoglycoside aerosols in cystic fibrosis," Eur. Respir. J., 18(2):316-322 (2001).
Desai et al., "A facile method of delivery of liposomes by nebulization," Journal of Controlled Release, 84(1-2):69-78 (2002).
Desai et al., "A Novel Approach to the Pulmonary Delivery of Liposomes in Dry Powder Form to Eliminate the Deleterious Effects of Milling," Journal of Pharmaceutical Sciences, 91(2):482-491 (Feb. 2002).
Desai, T. R. et al., "Determination of surface free energy of interactive dry powder liposome formulations using capillary penetration technique," Colloids and Surfaces B: Biointerfaces, 22:107-113 (2001).
Desai, "Delivery of liposomes in dry powder form: aerodynamic dispersion properties," European Journal of Pharmaceutical Sciences 20:459-467 (2003).
Di Ninno et al. (1993). Liposome-encapsulated ciprofloxacin is effective in the protection and treatment of BALB/c mice against Francisella tularensis. The Journal of Infectious Diseases 168, pp. 793-794.
Dickie, K. J. et al., "Ventilatory effects of aerosolized kanamycin and polymyxin," Chest, 63(5):694-697 (1973).
Dong, C. et al., "Acacia-gelatin microencapsulated liposomes: preparation, stability and release of acetylsalicylic acid," Pharmaceutical Research, 10(1):141-146 (1993).
Doring, G. et al., "Antibiotic therapy against Pseudomonas aeruginosa in cystic fibrosis: a European consensus," Eur Respir J., 16(4):749-767 (2000).
Drenkard, E. et al., "Pseudomonas biofilm formation and antibiotic resistance are linked to phenotypic variation," Nature, 416:740-743 (2002).

(56) References Cited

OTHER PUBLICATIONS

Driscoll et al., "Intratracheal Instillation as an Exposure Technique for the Evaluation of Respiratory Tract Toxicity: Uses and Limitations," Toxicological Sciences, 55, pp. 24-35 (2000).
Dupont et al., "A randomized placebo-controlled study of nebulized liposomal amikacin (Arikace) in the treatment of cystic fibrosis patients with chronic Pseudomonas aeruginosa lung infection," Journal of Cystic Fibrosis, 1(7):S26, Abstract 102, Jan. 2008.
Duzgunes, N. et al., "Treatment of intracellular *Mycobacterium avium* complex infection by free and liposome-encapsulated sparfloxacin," Antimicrobial Agents and Chemotherapy, 40(11):2618-2621 (Nov. 1996).
Eboka (2005). Aqueous solubility of ciprofloxacin in the presence of metal cations. Tropical Journal of Pharmaceutical Research, 4(1), pp. 349-354.
Ehlers, S. et al., "Liposomal amikacin for treatment of *M. avium* Infections in clinically relevant experimental settings," Zbl. Bakt., 284:218-231 (1996).
Eigen (1995). A multicenter study of alternate-day prednisone therapy in patients with cystic fibrosis. The Journal of Pediatrics, 126(4), pp. 515-523.
El-Din, M. A. T. et al., "Nebulizer therapy with antibiotics in chronic suppurative lung disease," Journal of Aerosol Medicine, 7(4):345-350 (1994).
Elhissi et al., "Formulations generated from ethanol-based proliposomes for delivery via medical nebulizers," Journal of Pharmacy and Pharmacology, 58:887-894 (Jul. 2006).
Eller, J. M. et al., "The therapy of bronchiectasis," Deutsche Medizinische Wochenschrift, 118(44):1608-1610 (1993).
Farber, J. E. et al., "The use of aerosol penicillin and streptomycin in bronchopulmonary infections," California Medicine, 73(3):214-217 (1950).
Fenske et al., "Encapsulation of weakly-basic drugs, antisense oligonucleotides, and plasmid DNA within large unilamellar vesicles for drug delivery applications," Liposomes Second Edition a Practical Approach, pp. 167-191, V. Torchilin et al. eds. (2003).
Fielding, R. M. et al., "Pharmacokinetics and Urinary Excretion of Amikacin in Low-Clearance Unilamellar Liposomes after a Single or Repeated Intravenous Administration in the Rhesus Monkey," Antimicrobial Agents and Chemotherapy, 43(3):503-509 (1999).
Finke, W., "Long-term antibiotic therapy in chronic bronchitis and infectious asthma. Control and prevention of bronchopulmonary disease." Antibiotics and Chemotherapy, 4(3):319-329 (1954).
Finlay, W. H. et al., "Regional lung deposition of nebulized liposome-encapsulated ciprofloxacin," International Journal of Pharmaceutics (Amsterdam), 167(1-2):121-127 (Jun. 1, 1998).
Fountain, M. W. et al., "Treatment of *Brucella canis* and *Brucella abortus* In vitro and in vivo by stable plurilamellar vesicle-encapsulated aminoolycosides," The Journal of Infectious Diseases, 152(3):529-535 (1985).
Furneri et al., "Ofloxacin-Loaded Liposomes: In Vitro Activity and Drug Accumulation in Bacteria," Antimicrobial Agents Chemotherapy, 44(9):2458-2464 (2000).
Garcia, A. T., "Efficacy of amikacin sulfate in lower respiratory infections," Investigacion Medica Internacional, 9(3):235-240 (1982) (with English Abstract).
Gay et al., "In Vitro Activities of Norfloxacin and Ciprofloxacin Against *Mycobacterium tuberculosis*, *M. avium* Complex, *M. chelonei*, *M. fortuitum*, and *M. kansaii*," Antimicrobial Agents and Chemotherapy, vol. 26, No. 1, pp. 94-96 (Jul. 1984).
Geller, D. E. et al., "Pharmacokinetics and bioavailability of aerosolized tobramycin in cystic fibrosis," Chest, 122(1):219-226 (2002).
Gibson, R. L. et al., "Pathophysiology and management of pulmonary infections in cystic fibrosis," American Journal of Respiratory and Critical Care Medicine, 168(8):918-951 (2003).
Gibson, R. L. et al., "Significant microbiological effect of inhaled tobramycin in young children with cystic fibrosis," American Journal of Respiratory and Critical Care Medicine, 167(6):841-849 (2003).
Gilbert, B. E. et al., "Tolerance of volunteers to cyclosporine A-dilauroylphosphatidylcholine liposome aerosol," American Journal of Respiratory and Critical Care Medicine, 156(6):1789-1793 (1997).
Gleiser, C. A. et al., "Pathology of experimental respiratory anthrax in Macaca mulatta," Brit. J. Exp. Path., 44:416-426 (1963).
Goldman, J. M. et al., "Inhaled micronised gentamicin powder: a new delivery system," Thorax, 45:939-940 (1990).
Goss, C. H. et al., "Update on cystic fibrosis epidemiology," Current Opinion in Pulmonary Medicine, 10(6):510-514 (2004).
Graczyk, J. et al., "*Staphylococcal pneumonia*—analysis of material of patients treated in lung diseases hospital in years 1981-1994," Pneumonologia I Alergologia Polska, 65(11-12):767-774 (1997) (with English Abstract).
Greene, K. E. et al., "Radiographic changes in acute exacerbations of cystic fibrosis in adults: A pilot study," AJR, 163:557-562 (1994).
Gubernator, J., "Active methods of drug loading into liposomes: recent strategies for stable drug entrapment and increased in vivo activity," Expert Opinion in Drug Delivery, vol. 8(5), 2011, pp. 565-580.
Gunther, A. et al., "Surfactant alteration and replacement in acute respiratory distress syndrome," Respiratory Research, 2(6): 353-364 (2001).
Gursoy et al. (1997). Characterization of ciprofloxacin liposomes; derivative ultraviolet spectrophotometric determinations. J. Microencapsulation 14(6), pp. 769-776.
Hansen, C. R. et al., "Long-term azithromycin treatment of cystic fibrosis patients with chronic pseudomonas aeruginosa infection: an observational cohort study," Journal of Cystic Fibrosis, 4(1):35-40 (2005).
Helbich, T. et al., "High-resolution computed tomography of the lung in young patients with cystic fibrosis," Radiologe, 33(3):142-146 (1993) (English Abstract).
Hess, D. et al., "Medication nebulizer performance. Effects of diluent volume, nebulizer flow, and nebulizer brand," Chest, 110:498-505 (1996).
Hess, D. R., "Nebulizers: Principles and Performance," Respiratory Care, 45(6):609-622 (2000).
Hewitt, W. L. et al., "Antibiotic therapy of abscess of the lung and bronchiectasis," California Medicine, 76(5):319-324 (1952).
Hoffman, L. R. et al., "Aminoglycoside antibiotics induce bacterial biofilm formation," Nature, 436:1171-1175 (2005).
Honeybourne, D., "Antibiotic penetration in the respiratory tract and implications for the selection of antimicrobial therapy," Current Opinion in Pulmonary Medicine 1997, 3(2):170-174.
Howell, S. B., "Clinical applications of a novel sustained-release injectable drug delivery system: DepoFoam Technology," Cancer Journal, 7(3):219-227 (2001).
Hrkach, J. S. et al., "Synthesis of poly(L-lactic acid-co-L-lysine) graft copolymers," Macromolecules, 28:4736-4739 (1995).
Hrkach, J. S. et al., "Poly(L-Lactic acid-co-amino acid) graft copolymers: A class of functional biodegradable biomaterials," In: Hydrogels and Biodegradable Polymers for Bioapplications, Chapter 8, ACS Symposium Series No. 627, Ottenbrite, R. M. et al. (eds.), American Chemical Society, pp. 93-102 (1996).
Huang, L. et al., "Progress of liposome's applications in biomedicine," International Journal of Biologicals, 29(3):130-132 and 137 (2006).
Huang et al. (2006). Pulmonary delivery of insulin by liposomal carriers. Journal of Controlled Release 113, pp. 9-14.
Hubble, D., "Discussion on respiratory catarrh in children," Proceedings of the Royal Society of Medicine, 52(9):701-710 (1959).
Hung, O. R. et al., "Pharmacokinetics of inhaled liposome-encapsulated fentanyl," Anesthesiology, 83(2): 277-284 (Aug. 1995).
Hung, J. C. et al., "Evaluation of two commercial jet nebulisers and three compressors for the nebulisation of antibiotics," Archives of Disease in Childhood, 71(4):335-338 (Oct. 1994).
Hunt, B. E. et al., "Macromolecular mechanisms of sputum inhibition of tobramycin activity," Antimicrobial Agents and Chemotherapy, 39(1):34-39 (1995).
Hyde et al., "Anatomy, pathology, and physiology of the treacheobronchial tree: Emphasis on the distal airways," J. Allergy Clin. Immunol., vol. 124, No. 6, pp. S72-S77 (2009).

(56) References Cited

OTHER PUBLICATIONS

Ikegami, M. et al., "Surfactant protein metabolism in vivo," Biochimica et Biophysica Acta, 1408:218-225 (1998).
Ikemoto, H. et al., "Susceptibility of bacteria isolated from the patients with lower respiratory tract infections to antibiotics," The Japanese Journal of Antibiotics, 42(11):2350-2353 (1989).
IP, M. S. M. et al., "Bronchiectasis and related disorders," Respirology, 1:107-114 (1996).
Ishii, F. et al., "Procedure for Preparation of Lipid Vesicles (Liposomes) Using the Coacervation (Phase Separation) Technique," Langmuir, 11(2):483-486 (1995).
Jayaraman, S. et al., "Noninvasive in vivo fluorescence measurement of airway-surface liquid depth, salt concentration, and pH," J. Clin. Invest. 107:317-324 (2001).
Johnston, M. J. W. et al., "Therapeutically optimized rates of drug release can be achieved by varying the drug-to-lipid ratio in liposomal vincristine formulations," Biochimica et Biophysica Acta, 1758:55-64 (2006).
Katare, O. P. et al., "Enhanced in vivo Performance of LiposomalIndomethacin Derived From Effervescent Granule Based Proliposomes," J. Microencapsulation, 12(5):487-493 (1995).
Kensil et al., "Alkaline Hydrolysis of Phospholipids in Model Membranes and the Dependence on Their State of Aggregation," Biochemistry, 20:6079-6085 (1981).
Kesavalu, L. et al., "Differential effects of free and liposome encapsulated amikacin on the survival of *Mycobacterium avium* complex in mouse peritoneal macrophages," Tubercle, 71(3):215-217 (1990).
Kim, E. K. et al., "Pharmacokinetics of intravitreally injected liposomes encapsulated tobramycin in normal rabbits," Yonsei Medical Journal, 31(4):308-314 (1990).
Klemens, S. P. et al., "Liposome-encapsulated-gentamicin therapy of *Mycobacterium avium* complex infection in beige mice," Antimicrobial Agents and Chemotherapy, 34(6):967-970 (1990).
Knoch, M. et al., "The customised electronic nebuliser: a new category of liquid aerosol drug delivery systems," Expert Opin. Drug Deliv., 2(2):377-390 (2005).
Knox, K. et al., "Chronic bronchitis. An attempt to control chronic infection with Haemophilus influenzae by aerosol therapy," The Lancet, pp. 120-122 (1955).
Kyriacos et al., "In Vitro Testing of Ciprofloxacin Formulations and Preliminary Study on BCS Biowaiver," Journal of Food and Drug Analysis, (2009) 17(2): 78-84.
Labiris, N. R. et al., "Pulmonary drug delivery. Part II: The role of inhalant delivery devices and drug formulations in Therapeutic effectiveness of aerosolized medications," Br.J.Clin.Pharmacol., 56(6):600-612 (2003).
Lagace, J. et al., "Liposome-encapsulated antibiotics: preparation, drug release and antimicrobial activity against Pseudomona aeruginosa," Journal Microencapsulation, 8(1) 53-61 (1991).
Landyshev, Y. S. et al., "Clinical and experimental aspects of liposomal hydrocortisone treatment of bronchial asthma," Ter. Arkh., 74(8):45-48 (2002) (with English Abstract).
Lasic et al., "Transmembrane gradient driven phase transitions within vesicles: lessons for drug delivery," Biochemica et Biophysica Acta, 1239:145-156 (1995).
Lasic, D. D., "Gelation of liposome interior: A novel method for drug encapsulation," FEBS Letters, 312(2.3):255-258 (Nov. 1992).
Lass, J. S. et al., "New advances in aerosolised drug delivery: vibrating membrane nebuliser technology," Expert Opin Drug Deliv., 3(5):693-702 (2006).
Le Brun, P. P. H. et al., "A review of the technical aspects of drug nebulization," Pharmacy World & Science, 22(3):75-81 (2000).
Le Brun, P. P. H. et al., "Inhalation of tobramycin in cystic fibrosis part 1: The choice of a nebulizer," International Journal of Pharmaceutics, 189:205-214 (1999).
Le Brun, P. P. H. et al., "Inhalation of tobramycin in cystic fibrosis part 2: Optimization of the tobramycin solution for a jet and ultrasonic nebulizer," International Journal of Pharmaceutics, 189:215-225 (1999).
Le Brun, P. P. H. et al., "Dry powder inhalation of antibiotics in cystic fibrosis therapy: part 2. Inhalation of a novel colistin dry powder formulation: a feasibility study in healthy volunteers and patients," European Journal of Pharmaceutics and Biopharmaceutics, 54:25-32 (2002).
Li, Z. et al., "Nebulization of liposomal amikacin formulations: SLIT Amikacin," Respiratory Drug Delivery, 3:801-804 (2006).
Li, Z. et al., "Characterization of nebulized liposomal amikacin (Arikace) as a function of droplet size," Journal of Aerosol Medicine and Pulmonary Drug Delivery, 21(3):245-253 (2008).
Lin, H.-C. et al., "Inhaled gentamicin reduces airway neutrophil activity and mucus secretion in bronchiectasis," Am. J. Respir. Crit. Care Med., 155:2024-2029 (1997).
Lipuma, J. J., "Microbiological and immunologic considerations with aerosolized drug delivery," Chest. Sep. 2001;120(3 Suppl):118S-123S.
Lowry et al., "Effects of pH and osmolarity on aerosol-induced cough in normal volunteers," Clinical Science, 74:373-376 (1988).
Lutwyche, P. et al., "Intracellular delivery and antibacterial activity of gentamicin encapsulated in pH-sensitive liposomes," Antimicrobial Agents and Chemotherapy, 42(10):2511-2520 (1998).
Magallanes, M. et al., "Liposome-incorporated ciprofloxacin in treatment of murine salmonellosis," Antimicrobial Agents and Chemotherapy, Nov. 1993, 37(11):2293-2297.
Majumdar, S. et al., "Efficacies of Liposome-Encapsulated Streptomycin and Ciprofloxacin against *Mycobacterium avium*-M. intracellulare Complex Infections in Human Peripheral Blood Monocyte/Macrophages," Antimicrobial Agents and Chemotherapy, 36(12):2808-2815 (Dec. 1992).
Marcotte, G. V. et al., "Chronic productive cough and bronchiectasis in a 40-year-old woman," Annals of Allergy, Asthma & Immunology, 78(6):559-564 (1997).
Marier, J. F. et al., "Liposomal tobramycin against pulmonary infections of Pseudomonas aeruginosa: a pharmacokinetic and efficacy study following single and multiple intratracheal administrations in rats," Journal Antimicrobial Chemotherapy, 52:247-252 (2003).
Marier, J-F. et al., "Pharmacokinetics and efficacies of liposomal and conventional formulations of tobramycin after intratracheal administration in rats with pulmonary burkholderia cepacia infection," Antimicrobial Agents and Chemotherapy, 46(12):3776-3781 (2002).
Mariotti, A. B. et al., "Aerosol therapy with tobramycin in exacerbations of chronic obstructive lung disease (7 cases)," 66(2):198-202 (1996) (with English Abstract).
Martini, W. Z. et al., "Lung surfactant kinetics in conscious pigs," Am J Physiol., 277(1 Pt 1): E187-E195 (1999).
Marwah, O. S. et al., "Bronchiectasis. How to identify, treat and prevent," Postgrad. Med., 97(2):149-150, 153-156, 159 (1995) (Abstract).
Maurer, N. et al., "Anomalous solubility behavior of the antibiotic ciprofloxacin encapsulated in liposomes: a 1H-NMR study," Biochimica et Biophysica Acta, 1374:9-20 (1998).
McAllister, S. M. et al., "Antimicrobial properties of liposomal polymyxin B," Journal of Antimicrobial Chemotherapy, 43:203-210 (1999).
Meers, P. et al., "Biofilm penetration, triggered release and in vivo activity of inhaled liposomal amikacin in chronic Pseudomonas aeruginosa lung infections," Journal of Antimicrobial Chemotherapy, 61(4):859-868 (2008).
Mendelman, P. M. et al., "Aminoglycoside penetration, inactivation, and efficacy in cystic fibrosis sputum," American Review of Respiratory Disease, 132(4):761-765 (1985).
Mercer, R. R. et al., "Cell Number and Distribution in Human and Rat Airways," Am. J. Respir. Cell Mol. Biol., vol. 10, pp. 613-624, 1994.
Mohanty, B. et al., "Systematic of alcohol-induced simple coacervation in aqueous gelatin solutions," Biomacromolecules, 4:1080-1086 (2003).
Mombelli, G. et al., "Anti-pseudomonas activity in bronchial secretions of patients receiving amikacin or tobramycin as a continuous infusion," Antimicrobial Agents and Chemotherapy, 19(1):72-75 (1981).

(56) References Cited

OTHER PUBLICATIONS

Montero et al. (1998). Fluoroquinolone-biomembrane interactions: monolayer and calorimetric studies. Langmuir 14(9), pp. 2451-2454.
Morgan, J. R. et al., "Preparation and properties of liposome-associated gentamicin," Antimicrobial Agents and Chemotherapy, 17(4):544-548 (1980).
Moss, R. B., "Administration of aerosolized antibiotics in cystic fibrosis patients," Chest, 120(3 Suppl):107S-113S (Sep. 2001).
Myers, M. A. et al., "Pulmonary effects of chronic exposure to liposome aerosols in mice," Experimental Lung Research, 19:1-19 (1993).
Nakazawa, S. et al., "Studies on a new aminoglycoside antibiotic, amikacin (BB-K8) in pediatrics," The Japanese Journal of Antibiotics, 27(4):438-445 (1974).
Nasu, M. et al., "Appropriate use of antimicrobial agents," Selection of Anti-infective, Clinic in Japan (Special Number) Infection Disease Study in New Era (first volume), 2003, 61st issue, pp. 718-723.
National Jewish Health, "Third sputum smear test negative for XDR TB patient Andrew Speaker," [Online], Retrieved from the Internet: <URL: https://www.nationaljewish.org/about/news/press-releases/2007/smear-test-3>, Jun. 5, 2007, 2 pages.
Fresenius Kabi USA, New Drug Application (NDA): 019887, NebuPent® on Drugs@FDA [online], <https://www.accessdata.fda.gov/scripts/cder/daf/index.cfm?event=BasicSearch.process>, Retrieved on Apr. 24, 2017.
Newton, D. W. et al., Chapter 4: "Coacervation: Principles and Applications," In: Polymers for Controlled Drug Delivery, Tarcha, P. J. (ed.), CRC Press, Boca Raton, pp. 67-81 (1991).
Nightingale, S. D. et al., "Liposome-encapsulated gentamicin treatment of *Mycobacterium avium-Mycobacterium intracellulare* complex bacteremia in AIDS patients," Antimicrobial Agents and Chemotherapy, 37(9):1869-1872 (1993).
Nikolaizik et al., "A pilot study to compare tobramycin 80 mg injectable preparation with 300 mg solution for inhalation in cystic fibrosis patients," Canadian Respiratory Journal, 15(5):259-262, Jul./Aug. 2008.
Niven, R. W. et al., "Nebulization of liposomes. I. Effects of lipid composition," Pharmaceutical Research, 7(11):1127-1133 (Nov. 1990).
Niven, R. W. et al., "Nebulization of liposomes. II. The effects of size and modeling of solute release profiles," Pharmaceutical Research, 8(2):217-221 (1991).
Niven, R. W. et al., "Nebulization of liposomes. III. The effects of operating conditions and local environment," Pharmaceutical Research, 9(4):515-520 (1992).
U.S. Department of Health and Human Services, "Nonclinical Safety Evaluation of Reformulated Drug Products and Products Intended for Administration by an Alternate Route, Guidance for Industry and Review Staff, Good Review Practice," Oct. 2015, 12 pages.
Oh, Y-K et al., "Formulation and Efficacy of Liposome-Encapsulated Antibiotics for Therapy of Intracellular *Mycobacterium avium* Infection," Antimicrobial Agents and Chemotherapy, 39(9):2104-2111 (Sep. 1995).
Oizumi, K. et al., "Therapeutic effect of amikacin for infections with gram-negative bacilli, especially for stubborn respiratory infections," The Japanese Journal of Antibiotics, 31(1):15-23 (1978).
Olsen, A. M., "Streptomycin aerosol in the treatment of chronic bronchiectasis: preliminary report," Staff Meetings of the Mayo Clinic, pp. 53-54 (1946).
Olsen, A. M., "Nebulization therapy in bronchiectasis: The use of penicillin and streptomycin aerosols," In: Collected Papers of the Mayo Clinic and the Mayo Foundation, Hewitt, R. M. et al. (eds.), 38:579-586 (1946).
Olsen, A. M., "Nebulization therapy in bronchiectasis: The use of penicillin and streptomycin aerosols," J.A.M.A., 134(11):947-953 (1947).
Omri, A. et al., "Incorporation, release and in-vitro antibacterial activity of liposomal aminoglycosides against Pseudomonas aeruginosa," Journal Antimicrobial Chemotherapy, 36(4):631-639 (1995).
Omri, A. et al., "Comparison of the bactericidal action of amikacin, netilmicin and tobramtcin in free and liposomal formulation against pseudomonas aeruginosa," Chemotherapy, 42:170-176 (1996).
Omri, A. et al., "Pulmonary retention of free and liposome-encapsulated tobramycin after intratracheal administration in uninfected rats and rats infected with Pseudomonas aeruginosa," Antimicrobial Agents and Chemotherapy, 38(5):1090-1095 (1994).
Pai, V. B. et al., "Efficacy and safety of aerosolized tobramycin in cystic fibrosis," Pediatric Pulmonology, 32(4):314-327 (2001).
Papahadjopoulos, D. et al., "Phospholipid model membranes. I. Structural characteristics of hydrated liquid crystals," Biochimica et Biophysica Acta., 135:624-638 (1967).
Paradisi, F. et al, "Acute and chronic bronchopulmonary infections and aminoglycoside antibiotics," Chemioterapia Antimicrobica, 1(2):224-227 (1978).
Parsek, M. R. et al., "Acyl-homoserine lactone quorum sensing gram-negative bacteria: a signaling mechanism involved in associations with higher organisms," Proc. Nat. Acad. Sci., 97(16):6789-6793 (2000).
Patton, J. S. et al., "The lungs as a portal of entry for systemic drug delivery, " Proc. Am. Thor. Soc., 1:338-344 (2004).
Perkins, W. R. et al., "Aerosolization of liposomal amikacin (Arikace) using different nebulizers: Selection of the eflow nebulizer," Poster and Oral Presentation at North American Cystic Fibrosis Conference (Oct. 2007), Pediatric Pulmonology, 42(30):356-357, abs. 434, 12 pages.
Perkins, W. R. et al., "Role of lipid polymorphism in pulmonary surfactant," Science, 273:330-332 (Jul. 1996).
Petersen, E. A. et al., "Liposomal amikacin: improved treatment of *Mycibacterium avium* complex infection in the beige mouse model," Journal Antimicrobial Chemotherapy, 38:819-828 (1996).
Petkowicz, J. et al., "Hypoglycemic Effect of Liposome-Entrapped Insulin Administered by Various Routes into Normal Rats," Pol. J. Pharmacol. Pharm., 41:299-304 (1989).
Piersimoni et al., "Pulmonary infections associated with non-tuberculous mycobacteria in immunocompetent patients," Lancet Infect Dis, 8: 323-334 (2008).
Pilewski, J. M. et al., "Role of CFTR in airway disease," Physiological Reviews, 79(1):S215-S255 (1999).
Pines, A. et al., "Treatment of severe pseudomonas infections of the bronchi," British Medical Journal, 1:663-665 (1970).
Pines, A. et al., "Gentamicin and colistin in chronic purulent bronchial infections," British Medical Journal, 2:543-545 (1967).
Potter, B. P., "Aerosol antibiotic therapy in suppurative diseases of the lung and bronchi," Diseases of the Chest, 15(4):436-448 (Apr. 1949).
Poyner, E. A. et al., "A comparative study on the pulmonary delivery of tobramycin encapsulated into liposomes and PLA microspheres following intravenous and endotracheal delivery," Journal of Controlled Release, 35(1):41-48 (1995).
Poyner, E. A. et al., "Preparation, properties and the effects of free and liposomal tobramycin on siderophore production by Pseudomonas aeruginosa," Journal of Antimicrobial Chemotherapy, 34:43-52 (1993).
Novartis Pharmaceuticals Corporation, TOBI, Tobramycin Inhalation Solution, USP, Nebulizer Solution, Prescribing Information, Oct. 2015, 14 pages.
Gilead Sciences, Inc., CAYSTON (aztreonam for inhalation solution) Highlights of Prescribing Information (2014), 19 pages.
Press Release, "Transave Announces Positive Phase II Results for Once-Daily Arikace in the Treatment of Cystic Fibrosis Patients Who Have Pseudomonas Lung Infections," Presented at the European Cystic Fibrosis Society Conference, Monmouth Junction, NJ, Jun. 13, 2008, 3 pages.
Price, C. I. et al., "Liposome delivery of aminoglycosides in burn wounds," Surgery, Gynecology & Obstetrics, 174(5):414-418 (May 1992).
Price, C. I. et al., "Liposome encapsulation: a method for enhancing the effectiveness of local antibiotics," Surgery, 115(4):480-487 (1994).

(56) References Cited

OTHER PUBLICATIONS

Price, C. I. et al., "Enhanced effectiveness of intraperitoneal antibiotics administered via liposomal carrier," Arch Surgery, 124:1411-1415 (1989).
Price, K. E. et al., "Amikacin, an aminoglycoside with marked activity against antibiotic-resistant clinical isolates," The Journal of Infectious Diseases, 134:S249-S261 (1976).
Ramsammy, L. S. et al., "The effect of gentamicin on the biophysical properties of phosphatidic acid liposomes is influenced by the O—C=O group of the lipid," Biochemistry, 27:8249-8254 (1988).
Ramsey, B. W. et al., "Intermittent administration of inhaled tobramycin in patients with cystic fibrosis. Cystic Fibrosis Inhaled Tobramycin Study Group," The New England Journal of Medicine, 340(1):23-30 (1999).
Ramsey, B. W. et al., "Efficacy of aerosolized tobramycin in patients with cystic fibrosis," The New England Journal of Medicine, 328:1740-1746 (1993).
Rastogi et al. (2006). Particulate and vesicular drug carriers in the management of tuberculosis. Current Drug Delivery 3(1), pp. 121-128.
Rau, J. L. et al., "Performance Comparison of Nebulizer Designs: Constant-Output, Breath-Enhanced, and Dosimetric," Respir. Care 2004;49(2):174-179.
Roehrborn, A. A. et al., "Lipid-based slow-release formulation of amikacin sulfate reduces foreign body-associated infections in mice," Antimicrobial Agents and Chemotherapy, 39(8):1752-1755 (1995).
Ross et al., "Aqueous solubilities of some variously substituted quinolone antimicrobials," International Journal of Pharmaceutics, 63(3): 237-250 (1990).
Sabra, W. et al., "Physiological responses of pseudomonas aeruginosa PAO1 to oxidative stress in controlled microaerobic and aerobic cultures," Microbiology, 148:3195-3202 (2002).
Saiman et al., "Antibiotic Susceptibility of Multiply Resistant Pseudomonas aeruginosa Isolated from Patients with Cystic Fibrosis, Including Candidates for Transplantation," Clinical Infectious Diseases, 23:532-537 (Sep. 1996).
Sangwan et al., "Aerosolized Protein Delivery in Asthma: Gamma Camera Analysis of Regional Deposition and Perfusion," Journal of Aerosol Medicine, vol. 14, No. 2, pp. 185-195 (2001).
Schaad, U. B. et al., "Efficacy of inhaled amikacin as adjunct to intravenous combination therapy (ceftazidime and amikacin) in cystic fibrosis," Journal of Pediatrics, 111(4):599-605 (Oct. 1987).
Schentag, J. J., Antimicrobial action and pharmacokinetics/pharmacodynamics: the use of AUIC to improve efficacy and avoid resistance, Journal of Chemotherapy, 11(6):426-439 (1999).
Schiffelers, R. et al., "Liposome-encapsulated aminoglycosides in pre-clinical and clinical studies," Journal of Antimicrobial Chemotherapy, 48:333-344 (2001).
Schiffelers, R. M. et al., "Therapeutic efficacy of liposomal gentamicin in clinically relevant rat models," International Journal of Pharmaceutics, 214:103-105 (2001).
Schiffelers, R. M. et al., "In vivo synergistic interaction of liposomecoencapsulated gentamicin and ceftazidime," Journal Pharmacology Experimental Therapeutics, 298(1):369-375 (2001).
Schlegel, L. et al., "In-vitro killing activity of combinations of beta-lactam agents with aminoglycosides against penicillin-resistant pneumococci," The Journal of Antimicrobial Chemotherapy, 39(1):95-98 (1997).
Schreier, H. et al., "Pulmonary delivery of amikacin liposomes and acute liposome toxicity in the sheep," International Journal of Pharmaceutics, 87(1-3):183-193 (1992).
Schreier, H. et al., "Pulmonary delivery of liposomes," Journal of Controlled Release, 24(1):209-223 (1993).
Sermet-Gaudelus, I. et al., "Nebulized antibiotics in cystic fibrosis," Pediatric Drugs, 4(7):455-467 (2002).
Sezer et al., "Encapsulation of Enrofloxacin in Liposomes I: Preparation and In Vitro Characterization of LUV," Journal of Liposome Research, 14(1-2):77-86 (2004).

Shah, S. P. et al., "Liposomal amikacin dry powder inhaler: effect of fines on in vitro performance," AAPS PharmSciTech, 5(4):e65:1-7 (2004).
Shek et al., "Liposomes in Pulmonary Applications: Physiochemical Considerations, Pulmonary Distribution and Antioxidant Delivery," Journal of Drug Targeting, 2:431-442 (1994).
Shima, K. et al., "A study of amikacin (BB-K8) on the clinical effects on the respiratory infection," Chemotherapy, 23(6):2128-2130 (1975) (with English Abstract).
Singh, P. K. et al., "Quorum-sensing signals indicate that cystic fibrosis lungs are infected with bacterial biofilms," Nature, 407:762-764 (2000).
Skubitz, K. M. et al., "Inhalational interleukin-2 liposomes for pulmonary metastases: a phase I clinical trial," Anti-Cancer Drugs, 11(7): 555-563 (2000).
Smith, A. L. et al., "Safety of aerosol tobramycin administration for 3 months to patients with cystic fibrosis," Pediatric Pulmonology, 7(4):265-271 (1989).
Smith et al. (1986). Pharmacokinetics and sputum penetration of ciprofloxacin in patients with cystic fibrosis. Antimicrobial Agents and Chemotherapy 30(4), pp. 614-616.
Stark, B., "Long-term stability of sterically stabilized liposomes by freezing and freeze-drying: Effects of cryoprotectants on structure," Eur. J. Pharm. Sci. 41:546-555 (2010).
Stott, P. W. et al., "Characterization of complex coacervates of some tricyclic antidepressants and evaluation of their potential for enhancing transdermal flux," Journal of Controlled Release, 41(3):215-227 (1996).
Strauss, G., "Stabilization of lipid bilayer by sucrose during freezing," PNAS (1986) 83:2422-2426.
Sunamoto et al., "Unexpected Tissue Distribution of Liposomes Coated With Amylopectin Derivatives and Successful Use in the Treatment of Experimental Legionnaires' Diseases," Receptor-Mediated Targeting of Drugs, vol. 82, pp. 359-371, G. Gregoriadis et al. eds. (1984).
Sunamoto et al., "Improved drug delivery directed to specific tissue using polysaccharide-coated liposomes," Multiphase Biomedical Materials, pp. 167-190, T. Tsuruta et al. eds. (1989).
Sweeney et al. (2005). Spray-freeze-dried liposomal ciprofloxacin powder for inhaled aerosol drug delivery. International Journal of Pharmaceutics 305, pp. 180-185.
Swenson, K. A. et al., "Pharmacokinetics and in vivo activity of liposome-encapsulated gentamicin," Antimicrobial Agents and Chemotherapy, 34(2)235-240 (1990).
Szoka, F. Jr. et al., "Comparative properties and methods of preparation of lipid vesicles (liposomes)," Ann. Rev. Biophys. Bioeng., 9:467-508 (1980).
Szoka, F. Jr. et al., "Procedure for preparation of liposomes with large internal aqueous space and high capture by reverse-phase evaporation," PNAS USA, 75(9):4194-4198 (Sep. 1978).
Tarran, R., "Regulation of Airway Surface Liquid Volume and Mucus Transport by Active Ion Transport," Proc. Am. Thorac. Soc., vol. 1, pp. 42-46, 2004.
Takamoto, M. et al., "Imipenem/cilastatin sodium alone or combined with amikacin sulfate in respiratory infections," The Japanese Journal of Antibiotics, 47(9):1131-1144 (1994) (with English Abstract).
Tateda, K. et al., "Efficacy of beta-lactam antibiotics combined with gentamicin against penicillin-resistant pneumococcal pneumonia in CBA/J mice," The Journal of Antimicrobial Chemotherapy, 43(3):367-371 (1999).
Taylor, K. M. G. et al., "The influence of liposomal encapsulation on sodium cromoglycate pharmacokinetics in man," Pharmaceutical Research, 6(7):633-636 (1989).
Ten, R. M. et al., "Interleukin-2 liposomes for primary immune deficiency using the aerosol route," International Immunopharmacology, 2(2-3):333-344 (2002).
Terzano, C. et al., "Tobramycin aerosol: could the delivery system influence the particle size and deposition in the lower airways?" Recenti. Prog. Med., 89(5):245-249 (1998) (English Abstract).
Thomas, D. A. et al., "Acute effects of liposome aerosol inhalation on pulmonary function in healthy human volunteers," Chest, 99(5):1268-1270 (1991).

(56) References Cited

OTHER PUBLICATIONS

Thomasin, C. et al., "Drug microencapsulation by PLA/PLGA coacervation in the light of thermodynamics. 2. Parameters determining microsphere formation," Journal of Pharmaceutical Sciences, 87(3):269-275 (1998).
Trafny, E. A. et al., "Effects of free and liposome-encapsulated antibiotics on adherence of Pseudomonas aeruginosa to collagen type I," Antimicrobial Agents and Chemotherapy, 39(12):2645-2649 (1995).
Ulrich, A. S., "Biophysical aspects of using liposomes as delivery vehicles," Bioscience Reports, 22(2):129-150 (Apr. 2002).
Van Der Straeten, M. et al., "Amikacin in the treatment of gram-negative bronchopulmonary infections," The Journal of Infectious Diseases, 134:S391-S393 (1976).
Van Heeckeren, A et al., "Effects of bronchopulmonary inflammation induced by Pseudomonas aeruginosa on adenovirus-mediated gene transfer to airway epithelial cells in mice," Gene Ther., 5(3):345-351 (Mar. 1998).
Van Heeckeren, A. et al., "Delivery of CFTR by adenoviral vector to cystic fibrosis mouse lung in a model of chronic Pseudomonas aeruginosa lung infection," Am J Physiol Lung Cell Mol Physiol. Apr. 2004;286(4):L717-26. Epub Sep. 26, 2003.
Van Heeckeren, A. et al., "Effect of Pseudomonas infection on weight loss, lung mechanics, and cytokines in mice," Am J Respir Crit Care Med. Jan. 2000;161(1):271.
Van Heeckeren, A. et al., "Murine models of chronic Pseudomonas aeruginosa lung infection," Lab Anim., 36(3):291-312 (Jul. 2002).
Van Heeckeren, A. et al., "Role of CFTR genotype in the response to chronic Pseudomonas aeruginosa lung infection in mice," Am J Physiol Lung Cell Mol Physiol. Nov. 2004;287(5):L944-52. Epub Jul. 9, 2004.
Vecellio, L., "The mesh nebuliser: a recent technical innovation for aerosol delivery," Breathe, 2(3):253-260 (2006).
Veldhuizen, R. et al., "The role of lipids in pulmonary surfactant," Biochimica et Biophysica Acta, 1408:90-108 (1998).
Vidgren, M. et al., "A study of 99m technetium-labelled beclomethasone dipropionate dilauroylphosphatidylcholine liposome aerosol in normal volunteers," International Journal of Pharmaceutics, 115:209-216 (1995).
Vitas, A. I. et al., "Effect of composition and method of preparation of liposomes on their stability and interaction with murine monocytes infected with *Brucella abortus*," Antimicrobial Agents and Chemotherapy, 40(1):146-151 (1996).
Wang, W. et al., "Research progress in pulmonary administration of liposome," Journal of Shenyang Pharmaceutical University, 17(3):226-229 (2000).
Wang, Z. et al., "Improved drug delivery: Spray freeze dried nano-liposomal inhaled aerosols," Proceedings of the 2004 International Conference on MEMS, NANO and Smart Systems (ICMENS 2004), Badawy W. et al. (eds.), (University of Calgary), 1 page.
Webb, M. S. et al., "Antibacterial Efficacy against an In Vivo *Salmonella typhimurium* Infection Model and Pharmacokinetics of a Liposomal Ciprofloxacin Formulation," Antimicrobial Agents and Chemotherapy, 42(1):45-52 (Jan. 1998).
Weber et al. (1997). Effect of nebulizer type and antibiotic concentration on device performance. Pediatric Pulmonology 23, pp. 249-260.
Weber, A. et al., "Nebulizer delivery of tobramycin to the lower respiratory tract," Pediatr Pulmonol., 17(5):331-339 (May 1994).
Wichert, B. V. et al., "Amikacin liposomes: characterization, aerosolization, and in vitro activity against *Mycobacterium avium*-intracellulare in alveolar macrophages," International Journal of Pharmaceutics, 78(1-3):227-235 (1992).
Wise et al. (1983). In vitro activity of Bay 09867, a new quinolone derivate compared with those of other antimicrobial agents. Antimicrobial Agents and Chemotherapy 23(4), pp. 559-564.
Westerman, E. M. et al., "Effect of nebulized colistin sulphate and colistin sulphomethate on lung function in patients with cystic fibrosis: a pilot study," Journal of Cystic Fibrosis, 3(1):23-28 (2004).
Whitehead, T. C. et al., "Kinetics and Toxicity of Liposomal and Conventional Amikacin in a Patient with Multidrug-Resistant Tuberculosis," Eur J Clin Microbiol. Infect. Dis., 17:794-797 (1998).
Winthrop, K. L. et al., "Subgroup Analyses of Baseline Demographics and Efficacy in Patients With Refractory Nontuberculous Mycobacteria (NTM) Lung Infection Treated With Liposomal Amikacin for Inhalation (LAI)," Poster presented at the ATS 2015 International Conference, May 15-20, 2015, Denver, CO, USA, 1 page.
Winthrop, K. L. et al., "Subgroup Analyses of Baseline Demographics and Efficacy in Patients With Refractory Nontuberculous Mycobacteria (NTM) Lung Infection Treated With Liposomal Amikacin for Inhalation (LAI)," Abstract, Diagnosis and Management of Nontuberculous Mycobacteria Infections, Poster Discussion Session, May 20, 2015, Colorado Convention Center, Am J Respir Crit Care Med 191;2015:A6294, Online Abstracts Issue, 2 pages.
Wolff, R. K. et al., "Toxicologic testing of inhaled pharmaceutical aerosols," Critical Reviews in Toxicology, 23(4):343-369 (1993).
Wolkers, W. F. et al., "Preservation of dried liposomes in the presence of sugar and phosphate," Biochimica et Biophysica Acta, 1661:125-134 (2004).
Wong et al., "Liposome delivery of ciprofloxacin against intracellular Francisella tularensis infection," Journal of Controlled Release, 92(3):265-273 (2003).
Worlitzsch, D. et al., "Effects of reduced mucus oxygen concentration in airway pseudomonas infections of cystic fibrosis patients," J. Clin. Invest., 109:317-325 (2002).
Xiu, L. et al., "Drug Resistant Analysis of Pseudomonas Aeruginosa in Patients with Mechanical Ventilation," Med. J. Chin. PLA, 27(6):544-545 (2002) (with English Abstract).
Yamazaki, Y. et al., "The ability to form biofilm influences *Mycobacterium avium* invasion and translocation of bronchial epithelial cells," Cellular Microbiology, 8(5):806-814 (2006).
Yanagihara, K. et al., "Design of anti-bacterial drug and anti-Mycobacterial drug for drug delivery system," Current Pharmaceutical Design, 8:475-482 (2002).
Yim, D. et al., "The Development of Inhaled Liposome-Encapsulated Ciprofloxacin to Treat Cystic Fibrosis," Respiratory Drug Delivery, pp. 425-428 (2006).
Yu et al., "The Effect of Temperature and pH on the Solubility of Quinolone Compounds: Estimation of Heat of Fusion," Pharmaceutical Research, vol. 11, No. 4, pp. 522-527 (1994).
Zeng, S. et al., "Intravitreal Pharmacokinetics of Liposome-encapsulated Amikacin in a Rabbit Model," Ophthamology, 100:1640-1644 (1993).
Zhanel et al., "A Critical Review of the Fluoroquinolones Focus on Respiratory Tract Infections," Drugs, 62(1):13-59 (2002).
Zhang, J. H. et al., "A Novel Method to Prepare Liposomes Containing Amikacin," Journal Microencapsulation, 16(4):511-516 (1999).
Zhang, X. et al., "Antibacterial drug treatment of community acquired pneumonia," Chinese Journal of Respiratory and Critical Care Medicine, 4(4):258-260 (2005).
Zhigaltsev, I. V. et al., "Formation of drug-arylsulfonate complexes inside liposomes: A novel approach to improve drug retention," Journal of Controlled Release, 110:378-386 (2006). Available online Nov. 28, 2005.
Xie, C., Respiratory Diseases, Scientific and Technological Documentation Press, Jun. 2000, pp. 79-81, Chapter II Section XI Pseudomonas aerugiosa Pneumonia.
Zlatanov, Z. et al., "Gentamycin-pharmachim. Aerosol inhalation treatment of patients with chronic bronchitis," Medico Biologic Information 2, pp. 5-8 (1976).
Abranches, J. et al., "Invasion of human coronary artery endothelial cells by *Streptococcus mutans* OMZ175," Oral Microbiol Immunol. Apr. 2009; 24(2):141-145. doi:10.1111/j.1399-302X.2008.00487.x.
Ahmad, S. et al., "Azithromycin effectiveness against intracellular infections of Francisella," BMC Microbiology 2010, 10:123.
Bahar, A. A. et al., "Antimicrobial peptides," Pharmaceuticals 2013, 6:1543-1575; doi:10.3390/ph6121543.
Chi, F. et al., "Vimentin-mediated signalling is required for IbeA+ *E. coli* K1 invasion of human brain microvascular endothelial cells," Biochem. J. (2010) 427, 79-90 (Printed in Great Britain) doi:10.1042/BJ20091097.

(56) References Cited

OTHER PUBLICATIONS

Cordeiro, C. et al., "Antibacterial Efficacy of Gentamicin Encapsulated in pH-Sensitive Liposomes against an In Vivo *Salmonella enterica* Serovar Typhimurium Intracellular Infection Model," Antimicrobial Agents and Chemotherapy, Mar. 2000, vol. 44, No. 3, p. 533-539.
Deshpande, R. G. et al., "Invasion of Aortic and Heart Endothelial Cells by Porphyromonas gingivalis," Infection and Immunity, Nov. 1998, vol. 66, No. 11, p. 5337-5343.
Domingue, G. J. et al., "Bacterial Persistence and Expression of Disease," Clinical Microbiology Reviews, Apr. 1997, vol. 10, No. 2, p. 320-344.
Dorn, B. R. et al., "Invasion of Human Coronary Artery Cells by Periodontal Pathogens," Infection and Immunity, Nov. 1999, vol. 67, No. 11, p. 5792-5798.
Samoshina, N. M. et al., "Fliposomes: pH-Sensitive Liposomes Containing a trans-2-morpholinocyclohexanol-Based Lipid That Performs a Conformational Flip and Triggers an Instant Cargo Release in Acidic Medium," Pharmaceutics 2011, 3, 379-405; doi:10.3390/pharmaceutics3030379.
Helguera-Repetto, A. C. et al., (May 2014) "Differential Macrophage Response to Slow- and Fast-Growing Pathogenic Mycobacteria," Hindawi Publishing Corporation, BioMed Research International, vol. 2014, Article ID 916521, 10 pages, http://dx.doi.org/10.1155/2014/916521.
Jo, E-K., "Innate immunity to mycobacteria: vitamin D and autophagy," Cellular Microbiology (2010) 12(8):1026-1035, doi:10.1111/j.1462-5822.2010.01491.x, First published online Jun. 15, 2010.
Kozarov, E., "Bacterial invasion of vascular cell types: vascular infectology and atherogenesis," Future Cardiol. Jan. 2012; 8(1):123-138. doi:10.2217/fca.11.75.
Leite, E. A. et al., "Encapsulation of cisplatin in long-circulating and pH-sensitive liposomes improves its antitumor effect and reduces acute toxicity," International Journal of Nanomedicine 2012:7 5259-5269.
Lutwyche, P. et al., "Intracellular Delivery and Antibacterial Activity of Gentamicin Encapsulated in pH-Sensitive Liposomes," Antimicrobial Agents and Chemotherapy, Oct. 1998, vol. 42, No. 10, p. 2511-2520.
Martin, D. W. et al., "Invasion and Intracellular Survival of Burkholderia cepacia," Infection and Immunity, Jan. 2000, vol. 68, No. 1, p. 24-29.
Nahire, R. et al., "pH-Triggered Echogenicity and Contents Release from Liposomes," Mol. Pharmaceutics 2014, 11, 4059-4068.
Nakano, K. et al., "Detection of Cariogenic Streptococcus mutans in Extirpated Heart Valve and Atheromatous Plaque Specimens," Journal of Clinical Microbiology, Sep. 2006, vol. 44, No. 9, p. 3313-3317.
Nightingale, S. D. et al., "Liposome-Encapsulated Gentamicin Treatment of *Mycobacterium avium-Mycobacterium intracellulare* Complex Bacteremia in AIDS patients," Antimicrobial Agents and Chemotherapy, Sep. 1993, vol. 37, No. 9, p. 1869-1872.
Niu, J. et al., "Role of MCP-I in cardiovascular disease: molecular mechanisms and clinical implications," Clinical Science (2009) 117:95-109 (Printed in Great Britain) doi:10.1042/CS20080581.
Oswald-Richter, K. A. et al., "Multiple mycobacterial antigens are targets of the adaptive immune response in pulmonary sarcoidosis," Respiratory Research 2010, 11:161.
Pierce, E. S., "Where Are All the *Mycobacterium avium* Subspecies *paratuberculosis* in Patients with Crohn's Disease?," Mar. 2009, PLoS Pathogens 5(3):e1000234. doi:10.1371/journal.ppat.1000234.
Pujol, C. et al., "Yersinia pestis Can Reside in Autophagosomes and Avoid Xenophagy in Murine Macrophages by Preventing Vacuole Acidification," Infection and Immunity, Jun. 2009, vol. 77, No. 6, p. 2251-2261.
Pollock, S. et al., "Uptake and trafficking of liposomes to the endoplasmic reticulum," FASEB J. 24, 1866-1878 (2010).
Rahman, S. A. et al., "Comparative Analyses of Nonpathogenic, Opportunistic, and Totally Pathogenic Mycobacteria Reveal Genomic and Biochemical Variabilities and Highlight the Survival Attributes of *Mycobacterium tuberculosis*," mBio, Nov./Dec. 2014, 5(6):e02020-14. doi:10.1128/mBio.02020.
Rose, S. J. et al., "Delivery of Aerosolized Liposomal Amikacin as a Novel Approach for the Treatment of Nontuberculous Mycobacteria in an Experimental Model of Pulmonary Infection," Sep. 2014, PLoS ONE 9(9): e108703. doi:10.1371/journal.pone.0108703.
Savage, P. B. et al., "Antibacterial properties of cationic steroid antibiotics," FEMS Microbiology Letters 217 (2002) 1-7.
Simoes, S. et al., "On the formulation of pH-sensitive liposomes with long circulation times," Advanced Drug Delivery Reviews 56 (2004) 947-965.
Sudimack, J. J. et al., "A novel pH-sensitive liposome formulation containing oleyl alcohol," Biochimica et Biophysica Acta 1564 (2002) 31-37.
Gerasimov, O. V. et al., "Cytosolic drug delivery using pH- and light-sensitive liposomes," Advanced Drug Delivery Reviews 38 (1999) 317-338.
Zeituni, A. E. et al., "Porphyromonas gingivalis-dendritic cell interactions: consequences for coronary artery disease," Journal of Oral Microbiology 2010, 2: 5782. doi: 10.3402/jom.v2i0.5782.
Supplementary European Search Report for European Application No. 08840993.3, dated Aug. 22, 2013.
International Preliminary Report on Patentability for International Application No. PCT/US2008/080954, dated Apr. 27, 2010, 6 pages.
International Search Report and Written Opinion for International Application No. PCT/US2008/080954, dated Jul. 17, 2009.
Anderson, K. E. et al., "Formulation and Evaluation of a Folic Acid Receptor-Targeted Oral Vancomycin Liposomal Dosage Form," Pharmaceutical Research, 18(3):316-322 (2001).
Couvreur, P. et al., "Liposomes and nanoparticles in the treatment of intracellular bacterial infections," Pharmaceutical Research, 8(9):1079-1085 (1991).
Vancomycin (Systemic), VA Classification Primary: AM900, Drugs.com [online], Retrieved from the Internet on Apr. 7, 2011: <URL: http://www.drugs.com/mmx/vancomycin-hydrochloride.html?printable=1>, dated Jun. 15, 1999, 15 pages.
Gonzales-Rothi, R. J. et al., "Liposomes and pulmonary alveolar macrophages: functional and morphologic interactions," Experimental Lung Research, 17:687-705 (1991).
Hagwood, S. et al., "Structure and properties of surfactant protein B," Biochimica et Biophysica Acta., 1408:150-160 (1998).
Janoff, A. S. et al., "Unusual lipid structures selectively reduce the toxicity of amphotericin B," Proc. Nat. Acad. Sci. USA, 85:6122-6126 (1988).
Johansson, J., "Structure and properties of surfactant protein C," Biochimica et Biophysica Acta, 1408:161-172 (1998).
Jones, M. N., "Use of Liposomes to Deliver Bactericides to Bacterial Biofilms," Methods of Enzymology, 391:211-228 (2005).
Kadry, A. A. et al., "Treatment of experimental osteomyelitis by liposomal antibiotics," Journal of Antimicrobial Chemotheraphy, 54(6):1103-1108 (2004).
Maiz, L. et al., "Aerosolized vancomycin for the treatment of methicillin-resistant *Staphylococcus aureus* infection in cystic fibrosis," Pediatric Pulmonology, 26(4):287-289 (1998).
Onyeji, C. O. et al., "Enhanced killing of methicillin-resistant *Staphylococcus aureus* in human macrophages by liposome-entrapped vancomycin and teicoplanin," Infection, 22(5):338-342 (1994).
Sanderson, N. M. et al., "Encapsulation of vancomycin and gentamicin within cationic liposomes for inhibition of growth of *Staphylococcus epidermidis*," Journal of Drug Targeting, 4(3):181-189 (1996).
Shek, P. N. et al., "Liposomes in pulmonary applications: Physicochemical considerations, pulmonary distribution and antioxidant delivery," J. Drug Target, 2:431-442 (1994).
Swenson, C. E. et al., "Liposomal aminoglycosides and TLC G-65," AIDS Patient Care, pp. 290-296 (1991).
Weiner, A. L., "Liposomes as carriers for polypeptides," Advanced Drug Delivery Review, 3(3):307-341 (May-Jun. 1989).

* cited by examiner

STABILIZED VANCOMYCIN FORMULATIONS

CROSS REFERENCE TO RELATED APPLICATIONS

This application is a 371 national phase entry of PCT Application No. PCT/US2013/072136, filed Nov. 27, 2013, which claims priority from U.S. Provisional Application Ser. No. 61/731,363, filed Nov. 29, 2012, both of which are incorporated herein by reference in their entirety for all purposes.

BACKGROUND OF THE INVENTION

Vancomycin is a branched tricyclic glycosylated non ribosomal peptide antibiotic produced by the fermentation of the *Actinobacteria* species *Amycolaopsis orientalis*, and is believed to act by inhibiting proper cell wall synthesis in Gram-positive bacteria. Additionally, it is believed that vancomycin alters cell membrane permeability and RNA synthesis. Accordingly, vancomycin is generally used in the prophylaxis and treatment of infections caused by Gram-positive bacteria that are unresponsive to other types of antibiotics.

Vancomycin has been reported as a treatment of last resort for infections that are resistant to other first line antibiotics. This is because vancomycin is given intravenously for most indications. Additionally, vancomycin presents toxicity concerns, and semi-synthetic penicillins have been developed and used preferentially over vancomycin. Nevertheless, the use of vancomycin has increased particularly with the spread of multiple-resistant *Staphylococcus aureus* (MRSA).

Methods for treating pulmonary disorders using liposomal vancomycin formulations are described in U.S. Publication Nos. US 2009-0105126 and US 2009-0104257, and U.S. Provisional Application Nos. 61/103,725 and 60/981,990, all of which are hereby incorporated by reference in their entireties. There is a need in the art for cost-effective vancomycin formulations that degrade at a slower rate and therefore exhibit improved stability. The present invention addresses these and other needs.

SUMMARY OF THE INVENTION

In one aspect, a stabilized lipid-based glycopeptide antibiotic composition is provided. In one embodiment, the composition comprises a lipid component, a glycopeptide antibiotic, and an amino acid or a derivative thereof. In a further embodiment, the amino acid or derivative thereof binds to the glycopeptide antibiotic and forms a stabilized glycopeptide antibiotic-amino acid complex. In even a further embodiment, the stabilized glycopeptide antibiotic-amino acid complex is entrapped by, or complexed with, the lipid component. In one embodiment, the antibiotic is vancomycin. In another embodiment, the antibiotic is teicoplanin, telavancin, oritavancin, decaplanin or dalbavancin. In one embodiment, the lipid component is a mixture of two or three lipids.

In one embodiment, a pharmaceutical composition comprising a lipid-based glycopeptide antibiotic is provided. In a further embodiment, the composition comprises a lipid component, a glycopeptide antibiotic, and an amino acid or derivative thereof. In a further embodiment, the amino acid or the derivative thereof stabilizes the glycopeptide antibiotic. In a yet further embodiment, the antibiotic and amino acid are entrapped by, or complexed with, the lipid. In one embodiment, the antibiotic is vancomycin, teicoplanin, telavancin, oritavancin, decaplanin or dalbavancin. In a further embodiment, the antibiotic is vancomycin.

In one embodiment, a stabilized lipid-based vancomycin formulation is provided that produces product degradants at a rate less than about 0.05% by weight per week at 4° C. In another embodiment, a stabilized lipid-based vancomycin composition is provided, and the composition produces product degradants at a rate less than about 0.03% by weight per week at 4° C. In a further embodiment, a stabilized lipid-based vancomycin composition is provided that produces product degradants at a rate less than about 0.02% by weight per week at 4° C. In yet a further embodiment, a stabilized lipid-based vancomycin composition is provided that produces product degradants at a rate less than about 0.01% by weight per week at 4° C. In one embodiment, the product degradants are crystalline degradation products.

In one embodiment, a stabilized lipid-based vancomycin formulation is provided that produces product degradants at a rate less than about 0.5% by weight per week at room temperature (RT). In another embodiment, a stabilized lipid-based vancomycin composition is provided that produces product degradants at a rate less than about 0.4% by weight per week at RT. In a further embodiment, a stabilized lipid-based vancomycin composition is provided where the composition produces product degradants at a rate less than about 0.2% by weight per week at RT. In one embodiment, the product degradants are crystalline degradation products.

In one embodiment, the stabilized lipid-based glycopeptide antibiotic composition comprising a lipid component, a glycopeptide antibiotic, and an amino acid or derivative thereof is at least about 44% more stable, or at least about 55% more stable, or at least about 66% more stable, or at least about 77% more stable, or at least about 88% more stable than a lipid-based glycopeptide antibiotic composition that does not comprise an amino acid or derivative thereof.

In another embodiment, the present invention relates to a stabilized lipid-based glycopeptide antibiotic comprising a lipid component, a glycopeptide antibiotic, and an amino acid or a derivative thereof, wherein the lipid component comprises a phospholipid. In a further embodiment, the phospholipid is phosphatidylcholine (PC), phosphatidylglycerol (PG), phosphatidylinositol (PI), phosphatidylserine (PS), phosphatidylethanolamine (PE), phosphatidic acid (PA), egg phosphatidylcholine (EPC), egg phosphatidylglycerol (EPG), egg phosphatidylinositol (EPI), egg phosphatidylserine (EPS), phosphatidylethanolamine (EPE), phosphatidic acid (EPA), soy phosphatidylcholine (SPC), soy phosphatidylglycerol (SPG), soy phosphatidylserine (SPS), soy phosphatidylinositol (SPI), soy phosphatidylethanolamine (SPE), soy phosphatidic acid (SPA), hydrogenated egg phosphatidylcholine (HEPC), hydrogenated egg phosphatidylglycerol (HEPG), hydrogenated egg phosphatidylinositol (HEPI), hydrogenated egg phosphatidylserine (HEPS), hydrogenated phosphatidylethanolamine (HEPE), hydrogenated phosphatidic acid (HEPA), hydrogenated soy phosphatidylcholine (HSPC), hydrogenated soy phosphatidylglycerol (HSPG), hydrogenated soy phosphatidylserine (HSPS), hydrogenated soy phosphatidylinositol (HSPI), hydrogenated soy phosphatidylethanolamine (HSPE), hydrogenated soy phosphatidic acid (HSPA), dipalmitoylphosphatidylcholine (DPPC), dimyristoylphosphatidylcholine (DMPC), dimyristoylphosphatidylglycerol (DMPG), dipalmitoylphosphatidylglycerol (DPPG), distcaroylphosphatidylcholine (DSPC), distcaroylphosphatidylglycerol (DSPG), dioleoylphosphatidylcholine (DOPC), dioleylphosphatidylethanolamine (DOPE), palmitoylstearoylphosphatidyl-choline (PSPC), palmitoylstearolphosphatidylglycerol (PSPG), mono-oleoyl-phosphatidylethanolamine (MOPE), tocopherol, tocopherol hemisuccinate, cholesterol sulfate, cholesteryl hemisuccinate, cholesterol derivatives, ammonium salts of fatty acids, ammonium salts of phospholipids, ammonium salts of glycerides, myristylamine, palmitylamine, laurylamine, stearylamine, dilauroyl ethylphosphocholine (DLEP), dimyristoyl ethylphosphocholine (DMEP), dipalmitoyl ethylphosphocholine (DPEP) and distearoyl ethylphosphocholine (DSEP). N-(2,3-di-(9-(Z)-octadecenyloxy)-prop-1-yl-N,N,N-trimethylammonium chloride (DOTMA), 1,2-bis(oleoyloxy)-3-(trimethylammonio) propane (DOTAP), distearoylphosphatidylglycerol (DSPG), dimyristoylphosphatidylacid (DMPA), dipalmitoylphosphatidylacid (DPPA), distearoylphosphatidylacid (DSPA), dimyristoylphosphatidylinositol (DMPI), dipalmitoylphosphatidylinositol (DPPI), distearoylphospatidylinositol (DSPI), dimyristoylphosphatidylserine (DMPS), dipalmitoylphosphatidylserine (DPPS), distearoylphosphatidylserine (DSPS), or mixtures thereof. In one embodiment, the lipid component comprises DPPC. In another embodiment, the lipid component comprises DPPG. In another embodiment, the lipid component comprises DPPC and DPPG. In one embodiment, the lipid component comprises one lipid, two lipids or three lipids. In yet another embodiment, the lipid component consists of one lipid, two lipids or three lipids.

In another embodiment, a stabilized lipid-based glycopeptide antibiotic comprising a sterol, a glycopeptide antibiotic, and an amino acid or a derivative thereof is provided. In one embodiment, the sterol is cholesterol. In another embodiment, the composition further comprises DPPC.

In another embodiment, the present invention comprises a stabilized lipid-based glycopeptide antibiotic comprising a lipid component comprising a phospholipid and a sterol, a glycopeptide antibiotic, and an amino acid or a derivative thereof. In one embodiment, the phospholipid and sterol are dipalmitoylphosphatidylcholine (DPPC) and cholesterol, respectively. In another embodiment, the phospholipid and sterol are dipalmitoylphosphatidylglycerol (DPPG) and cholesterol. In another embodiment, the phospholipid and sterol comprise DPPC, DPPG and cholesterol.

In one embodiment, the present invention comprises a stabilized lipid-based glycopeptide antibiotic comprising a lipid component, a glycopeptide antibiotic, and an amino acid or a derivative thereof, wherein the amino acid or derivative thereof is conjugated to the glycopeptide antibiotic to form a stabilized glycopeptide antibiotic-amino acid complex. In a further embodiment, the stabilized glycopeptide antibiotic-amino acid complex is entrapped by the lipid component. In a further embodiment, the lipid component is in a lipid clathrate, proliposome, micelle or liposome. In a further embodiment, the liposome has a mean particle size of about 0.05 to about 10 microns, 0.05 to about 1 microns, 0.05 to about 0.5 microns, about 0.1 to about 5.0 microns, about 0.1 to about 3.0 microns, about 0.1 to about 2.0 microns, about 0.1 to about 1.0 microns, about 0.1 to about 0.5 microns, about 0.1 to about 0.4 microns, about 0.1 to about 0.3 microns, or about 0.1 to about 0.2 microns. In another embodiment, the mean particular size of the liposome is about 1.0 microns or less, about 0.9 microns or less, about 0.8 microns or less, about 0.7 microns or less, about 0.6 microns or less, about 0.5 microns or less, about 0.4 microns or less, about 0.3 microns or less, or about 0.2 microns or less.

In one embodiment, the present invention provides a stabilized lipid-based glycopeptide antibiotic composition comprising a lipid component, vancomycin, and an amino acid or a derivative thereof. In one embodiment, the amino acid is D-alanine. In another embodiment, the amino acid is aspartic acid. In another embodiment, the amino acid derivative is bicine. In another embodiment, the amino acid is D-glutamic acid. In another embodiment, the amino acid derivative is glycylglycine (GLY-GLY). In yet another embodiment, the amino acid derivative is iminodiacetic acid (IDAA). In one embodiment, the vancomycin is conjugated to the amino acid or derivative thereof.

In one embodiment, a stabilized lipid-glycopeptide antibiotic comprising a lipid component, a glycopeptide antibiotic, and an amino acid or derivative thereof is provided, wherein the molar ratio of the glycopeptide antibiotic to the amino acid derivative thereof is from about 1:1 to about 1:4. In a further embodiment, the molar ratio of the glycopeptide antibiotic to the amino acid or derivative thereof is from about 1:1 to about 1:2. In a further embodiment, the molar ratio of the glycopeptide antibiotic to the amino acid or derivative thereof is about 1:1. In another embodiment, the molar ratio of the glycopeptide antibiotic to the amino acid or derivative thereof is about 1:2.

In another embodiment, the present invention relates to a stabilized lipid-glycopeptide antibiotic composition comprising a lipid component, a glycopeptide antibiotic, and an amino acid or derivative thereof, wherein the weight ratio of the total lipid component to the glycopeptide antibiotic is from about 0.1:1 to about 5:1. In a further embodiment, the weight ratio of the lipid component to the glycopeptide antibiotic is about 3:1 or less. In a further embodiment, the weight ratio of the lipid component to the glycopeptide antibiotic is about 1:1 or less. In another embodiment, the weight ratio of the lipid component to the glycopeptide antibiotic is less than 1:1.

In another aspect of the invention, a method for preparing a stabilized lipid-based glycopeptide antibiotic composition is provided. In some embodiments, the glycopeptide antibiotic is vancomycin. In a further embodiment, the method comprises mixing a first stream of a lipid solution containing a lipid in a solvent with a second stream of an aqueous solution comprising a glycopeptide antibiotic (e.g., vancomycin) and an amino acid or a derivative thereof. In one embodiment, the mixing of the two streams comprises infusing, in an in-line fashion, the first stream of the lipid solution with the second stream of the aqueous solution containing the glycopeptide antibiotic and amino acid or derivative thereof. In a further embodiment, the glycopeptide antibiotic and amino acid or derivative thereof is present as a conjugated complex. In a further embodiment, the glycopeptide antibiotic-amino acid complex is entrapped by the lipid when mixed in an in-line fashion. In a further embodiment, the solvent is ethanol. In another embodiment, the first stream of lipid solution is provided at a first flow rate and the second stream of aqueous solution is provided at a second flow rate. In a further embodiment, the first flow rate is about 1 L/min and the second flow rate is about 1.5 L/min.

In one embodiment, the second stream of the aqueous solution comprises the amino acid D-alanine. In another embodiment, the amino acid in the aqueous solution is aspartic acid. In another embodiment, the amino acid derivative in the aqueous solution is bicine. In another embodiment, the amino acid in the aqueous solution is D-glutamic acid. In another embodiment, the amino acid derivative in the aqueous solution is gycylglycine (GLY-GLY). In another embodiment, the amino acid derivative in the aqueous solution is iminodiacetic acid (IDAA).

In yet another aspect of the invention, a method for treating a bacterial pulmonary infection with a stabilized glycopeptide antibiotic composition is provided. In one embodiment, the method comprises administering to a subject in need thereof a therapeutically effective amount of an amino acid stabilized lipid-based glycopeptide antibiotic composition. In a further embodiment, the glycopeptide antibiotic is vancomycin. In another embodiment, the bacterial pulmonary infection is caused by a Gram-positive bacteria selected from the group consisting of *Staphylococcus, Streptococcus, Enterococcus, Bacillus, Corynebacterium, Nocardia, Clostridium*, and *Listeria*. In a further embodiment, the Gram-positive bacteria are selected from the group consisting of Methicillin-resistant *Staphylococcus aureus* (MRSA), *Escherichia coli, Klebsiella, Enterobacter, Serratia, Haemophilus, Yersinia pesos, Burkholderia pseudomallei, Burkholderia cepacia, Burkholderia gladioli, Burkholderia multivorans, Burkholderia vietnamiensis, Mycobacterium tuberculosis, Mycobacterium avium* complex (MAC)(*Mycobacterium avium* and *Mycobacterium intracellulare*), *Mycobacterium kansasii, Mycobacterium xenopi, Mycobacterium marinum, Mycobacterium mucogenicum, Mycobacgerium gordonae, Mycobacterium ulcerans*, and *Mycobacterium fortuitum* complex (including, but not limited to, *Mycrobacterium fortuitum, Mycrobacterium peregrinum, Mycrobacterium chelonae, Mycrobacterium abscessus*, and *Mycrobacterium mucogenicum*.

In one embodiment, a method for treating a pulmonary disease with a stabilized glycopeptide antibiotic composition is provided. In one embodiment, the pulmonary disease is cystic fibrosis, bronchiectasis, pneumonia, or chronic obstructive pulmonary disease (COPD). In another embodiment, a method for treating osteomyelitis; endocarditis; bronchitis; hepatitis; myocarditis; nephritis; bacteremia; a skin or connective tissue infection including, but not limited to, folliculitis, cellulitis, furuncules, or pymyositis; or a wound or surgical site infection with a stabilized glycopeptide antibiotic composition is provided.

In one embodiment, a composition comprising a stabilized lipid-based glycopeptide antibiotic for use in the therapy of cystic fibrosis, bronchiectasis, pneumonia, or chronic obstructive pulmonary disease (COPD) is provided. In another embodiment, a composition comprising a stabilized lipid-based glycopeptide antibiotic for use in the therapy of osteomyelitis; endocarditis; bronchitis; hepatitis; myocarditis; nephritis; bacteremia; a skin or connective tissue infection including, but not limited to, folliculitis, cellulitis, furuncules, or pymyositis; or a wound or surgical site infection is provided. In one embodiment, the composition for use in the therapy comprises a lipid component, a glycopeptide antibiotic, and an amino acid or a derivative thereof. In a further embodiment, the amino acid or derivative thereof binds to the glycopeptide antibiotic and forms a stabilized glycopeptide antibiotic-amino acid complex. In even a further embodiment, the stabilized glycopeptide antibiotic-amino acid complex is entrapped by, or complexed with, the lipid component. In one embodiment, the antibiotic is vancomycin. In another embodiment, the antibiotic is teicoplanin, telavancin, oritavancin, decaplanin or dalbavancin.

In one embodiment, a composition comprising a stabilized lipid-based glycopeptide antibiotic for use as a medicament in the treatment of cystic fibrosis, bronchiectasis, pneumonia, or chronic obstructive pulmonary disease (COPD) is provided. In another embodiment, a composition comprising a stabilized lipid-based glycopeptide antibiotic for use as a medicament in the treatment of osteomyelitis; endocarditis; bronchitis; hepatitis; myocarditis; nephritis; bacteremia; a skin or connective tissue infection including, but not limited to, folliculitis, cellulitis, furuncules, or pymyositis; or a wound or surgical site infection is provided. In one embodiment, the composition for use as a medicament comprises a lipid component, a glycopeptide antibiotic, and an amino acid or a derivative thereof. In a further embodiment, the amino acid or derivative thereof binds to the glycopeptide antibiotic and forms a stabilized glycopeptide antibiotic-amino acid complex. In even a further embodiment, the stabilized glycopeptide antibiotic-amino acid complex is entrapped by, or complexed with, the lipid component. In one embodiment, the antibiotic is vancomycin. In another embodiment, the antibiotic is teicoplanin, telavancin, oritavancin, decaplanin or dalbavancin.

In one embodiment, a composition comprising a stabilized lipid-based glycopeptide antibiotic for use in the manufacture of a medicament for cystic fibrosis, bronchiectasis, pneumonia, or chronic obstructive pulmonary disease (COPD) is provided. In another embodiment, a composition comprising a stabilized lipid-based glycopeptide antibiotic for use in the manufacture of a medicament for osteomyelitis; endocarditis; bronchitis; hepatitis; myocarditis; nephritis; bacteremia; a skin or connective tissue infection including, but not limited to, folliculitis, cellulitis, furuncules, or pymyositis; or a wound or surgical site infection is provided. In one embodiment, the composition for use in the manufacture of a medicament comprises a lipid component, a glycopeptide antibiotic, and an amino acid or a derivative thereof. In a further embodiment, the amino acid or derivative thereof binds to the glycopeptide antibiotic and forms a stabilized glycopeptide antibiotic-amino acid complex. In even a further embodiment, the stabilized glycopeptide antibiotic-amino acid complex is entrapped by, or complexed with, the lipid component. In one embodiment, the antibiotic is vancomycin. In another embodiment, the antibiotic is teicoplanin, telavancin, oritavancin, decaplanin or dalbavancin.

In another embodiment, the therapeutically effective amount of a stabilized lipid-based glycopeptide antibiotic composition is an amount greater than a minimum inhibitory concentration (MIC) for the bacterial pulmonary infection. In another embodiment, the therapeutically effective amount of a stabilized lipid-based glycopeptide antibiotic composition is a dose of about 50 to 1000 mg/day, about 100 to 500 mg/day, or about 250 to 500 mg/day. In a further embodiment, the dose is about 100 mg/day. In other embodiments, the dose is about 200 mg, about 300 mg, about 400 mg, or about 500 mg per day. In another embodiment, the composition is administered 1 time to 4 times a day. In a further embodiment, the composition is administered once a day, twice a day, three times a day or four times a day. In another embodiment, the composition is administered in a daily treatment cycle for a period of time, or is administered in a cycle of every other day, every third day, every fourth day, every firth day, every $6^{th}$ day or once a week for a period of time, the period of time being from one week to several months, for example, 1, 2, 3, or 4 weeks, or 1, 2, 3, 4, 5, or 6 months.

In another embodiment, the lipid based glycopeptide antibiotic composition is administered by inhalation as a nebulized spray, powder, or aerosol. In a further embodiment, the stabilized lipid based glycopeptide composition is administered via a nebulizer.

DETAILED DESCRIPTION OF THE INVENTION

Figure 1:
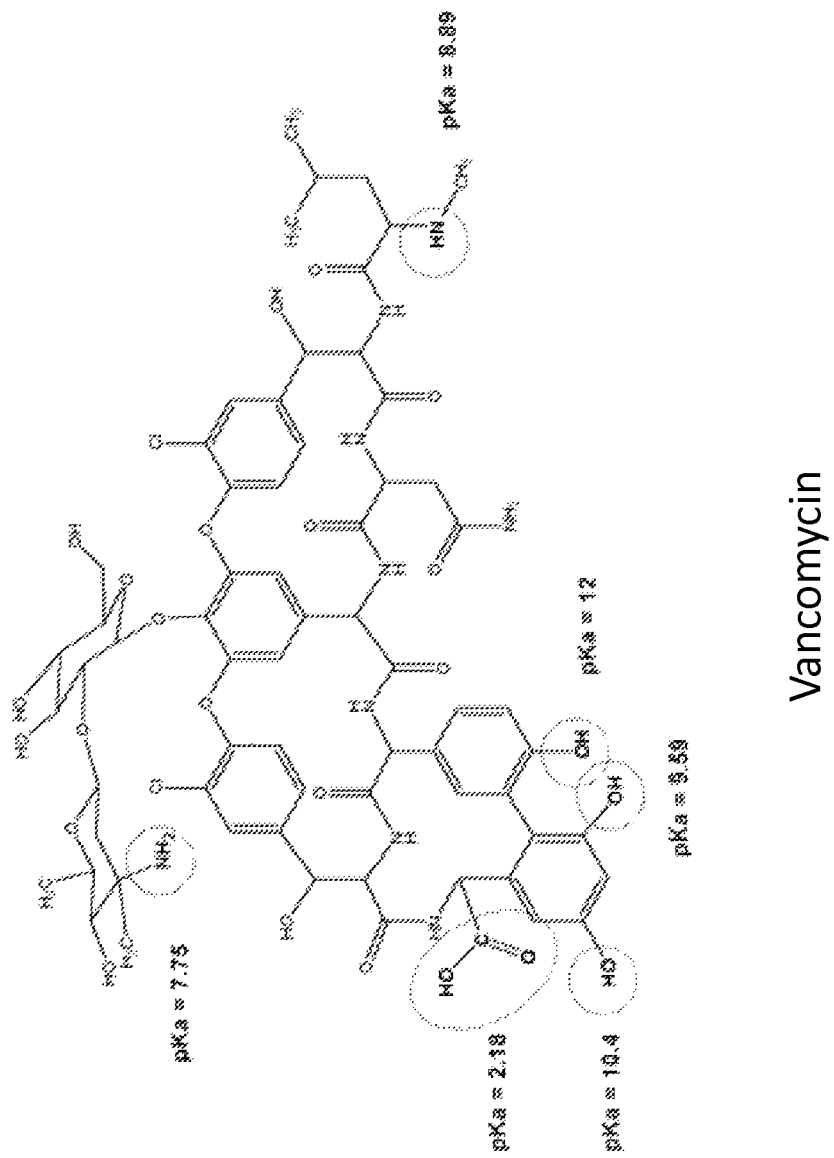
FIG. 1 shows the structure of vancomycin.

The abbreviations used herein for amino acids are those abbreviations which are conventionally used: A=Ala=Alanine; R=Arg=Arginine; N=Asn=Asparagine; D=Asp=Aspartic acid; C=Cys=Cysteine; Q=Gln=Glutamine; E=Glu=Gutamic acid; G=Gly=Glycine; H=His=Histidine; =Ile=lsoleucine; L=Leu=Leucine; K=Lys=Lysine; M=Met=Methionine; F=Phe=Phenylalanine; P=Pro=Proline; S=Ser=Serine; T=Thr=Threonine; W=Trp=Tryptophan; Y=Tyr=Tyrosine; V=Val=Valine. The amino acids in the compositions provided herein are L- or D-amino acids. In one embodiment, a synthetic amino acid is used in the compositions provided herein. In one embodiment, the amino acid increases the half-life, efficacy and/or bioavailability of the glycopeptide antibiotic in the composition. In a further embodiment, the glycopeptide antibiotic is vancomycin.

The term "amino acid derivative" as used herein refers to a moiety having both an amine functional group, either as $NH_2$, NHR, or $NR_2$, and a carboxylic acid functional group, either as $NH_2$, NHR, or $NR_2$, and a carboxylic acid functional group. The term "amino acids" encompasses both natural and unnatural amino acids, and can refer to alpha-amino acids, beta-amino acids, or gamma amino acids. Unless specified otherwise, an amino acid structure referred to herein can be any possible stereoisomer, e.g., the D or L enantiomer. In some embodiments, the amino acid derivatives are short peptides, including dipeptides and tripeptides. Exemplary amino acids and amino acid derivatives suitable for the invention include alanine (ALA), D-alanine (D-ALA), alanine-alanine (ALA-ALA), beta-alanine (bALA), alanine-beta-alanine (ALA-bALA), 3-aminobutanoic acid (3-ABA), gamma-aminobutyric acid (GABA), glutamic acid (GLU or GLUt), D-glutamic acid (D-GLU), glycine (GLY), glycylglycine (GLY-GLY), glycine-alanine (GLY-ALA), alanine-glycine (ALA-GLY), aspartic acid (ASP), D-aspartic acid (D-ASP), lysine-alanine-alanine (LYS-ALA-ALA), L-Lysine-D-alanine-D-alanine (L-LYS-D-ALA-D-ALA), bicine, tricine, sarcosine, and iminodiacetic acid (IDAA). Amino acids and derivatives thereof can be synthesized according to known techniques, or can be purchased from suppliers, e.g., Sigma-Aldrich (Milwaukee, Wis.).

The term "administering" includes in vive administration, as well as administration directly to tissue ex vivo. Generally, compositions may be administered systemically either orally, buccally, parenterally, topically, by inhalation or insufflation (i.e., through the mouth or through the nose), or rectally in dosage unit formulations containing conventional nontoxic pharmaceutically acceptable carriers, adjuvants, and vehicles as desired, or may be locally administered by means such as, but not limited to, injection, implantation, grafting, topical application, or parenterally.

In one embodiment, the composition of the invention is administered via inhalation. In a further embodiment, the composition of the invention is administered via nebulization, vaporization, aerosolization, or dry powder inhalation. A "nebulizer" or an "aerosol generator" in one embodiment, is used to administer the compositions of the present invention to a patient in need thereof. A "nebulizer" or an "aerosol generator" is a device that converts a liquid into an aerosol of a size that can be inhaled into the respiratory tract. Pneumonic, ultrasonic, electronic nebulizers, e.g., passive electronic mesh nebulizers, active electronic mesh nebulizers and vibrating mesh nebulizers are amenable for use with the invention if the particular nebulizer emits an aerosol with the required properties, and at the required output rate.

The process of pneumatically converting a bulk liquid into small droplets is called atomization. The operation of a pneumatic nebulizer requires a pressurized gas supply as the driving force for liquid atomization. Ultrasonic nebulizers use electricity introduced by a piezoelectric element in the liquid reservoir to convert a liquid into respirable droplets. Various types of nebulizers are described in Respiratory Care, Vol. 45, No. 6, pp. 609-622 (2000), the disclosure of which is incorporated herein by reference in its entirety. The terms "nebulizer" and "aerosol generator" are used interchangeably throughout the specification. "Inhalation device", "inhalation system" and "atomizer" are also used in the literature interchangeably with the terms "nebulizer" and "aerosol generator."

"Mass median aerodynamic diameter" or "MMAD" is normalized regarding the aerodynamic separation of aqua aerosol droplets and is determined by impactor measurements, e.g., the Anderson Cascade Impactor (ACI) and the Next Generation Impactor (NGI). The gas flow rate, in one embodiment, is 28 Liter per minute by the Anderson Cascade Impactor (ACI) and 15 liter per minute by the Next Generation Impactor (NGI). "Geometric standard deviation" or "GSD" is a measure of the spread of an aerodynamic particle size distribution.

In one embodiment, the MMAD of the aerosol of the pharmaceutical composition is less than about 4.9 m, less than about 4.5 µm, less than about 4.3 µm, less than about 4.2 µm, less than about 4.1 µm, less than about 4.0 µm or less than about 3.5 m, as measured by the ACI at a gas flow rate of about 28 L/minute, or by the Next Generation Impactor (NGI) at a gas flow rate of about 15 L/minute.

In one embodiment, the MMAD of the aerosol of the pharmaceutical composition is about 1.0 µm to about 4.2 µm, about 3.2 µm to about 4.2 µm, about 3.4 µm to about 4.0 µm, about 3.5 µm to about 4.0 µm or about 3.5 m to about 4.2 µm, as measured by the ACI. In one embodiment, the MMAD of the aerosol of the pharmaceutical composition is about 2.0 µm to about 4.9 µm, about 4.4 µm to about 4.9 µm, about 4.5 µm to about 4.9 µm, or about 4.6 m to about 4.9 µm, as measured by the NGI.

"Fine particle fraction" or "FPF", as used herein, refers to the fraction of the aerosol having a particle size less than 5 µm in diameter, as measured by cascade impaction. FPF is usually expressed as a percentage.

In one embodiment, the fine particle fraction (FPF) of the composition post nebulization, i.e., the aerosolized pharmaceutical composition, is about 50%, or about 55%, or about 60%, or about 65%, or about 70%, or about 75%, as measured by NGI or ACI. In a further embodiment, the FPF of the aerosol is greater than or equal to about 64%, as measured by the ACI, greater than or equal to about 70%, as measured by the ACI, greater than or equal to about 51%, as measured by the NGI, or greater than or equal to about 60%, as measured by the NGI.

In one embodiment, the FPF of the aerosolized composition is greater than or equal to 50%, greater than or equal to 60%, greater than or equal to 70%, greater than or equal to 80%, greater than or equal to 90%, greater than or equal to 95%, greater than or equal to 97.5%, or greater than or equal to 99%, as measured by cascade impaction. In a further embodiment, the composition comprises vancomycin and a liposome.

The terms "carrier," "excipient," and "vehicle" are used interchangeably herein and refer to materials suitable for formulation and administration of the pharmaceutically acceptable compositions described herein. Carriers useful herein include any materials known in the art which are nontoxic, do not interact with other components, do not cause significant irritation to an organism, and do not abrogate the biological activity and properties of the compound of the composition of the described invention. Carriers must be of sufficiently high purity and of sufficiently low toxicity to render them suitable for administration to the mammal being treated. The term "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio. The term "coacervation" refers to a separation into two liquid phases in colloidal systems. The phase more concentrated in the colloid component (active agent) is referred herein as the "coacervate." and the other phase is the equilibrium solution. Coacervate formation leads to higher internal active agent concentrations relative to external active agent concentrations and lower lipid to drug ratios.

The term "colloidal" refers to being of or relating to or having the properties of a colloid, meaning aggregates of atoms or molecules in a finely divided state (submicroscopic), dispersed in a gaseous, liquid or solid medium, and resisting sedimentation, diffusion, and filtration. A solution of macromolecules is a simple and the most common colloid system. Small molecules also can form association colloids as reversible aggregates. An association colloid is a reversible chemical combination due to weak chemical bonding forces wherein up to hundreds of molecules or ions aggregate to form colloidal structures with sizes of from about 1 to about 2000 nanometers or larger.

The term "effective amount" refers to the amount necessary or sufficient to realize a desired biologic effect.

The term "hydrophilic" refers to a material or substance having an affinity for polar substances, such as water. The term "lipophilic" refers to preferring or possessing an affinity for a non-polar environment compared to a polar or aqueous environment.

The term "solvent" as used herein refers to a substance capable of dissolving another substance ("a solute") to form a solution.

"Solvent infusion" is a process that includes dissolving one or more lipids in a small, minimal, amount of a process compatible solvent to form a lipid suspension or solution and then adding the solution to an aqueous medium containing bioactive agents. Typically a process compatible solvent is one that can be washed away in an aqueous process such as dialysis. The composition that is cool/warm cycled in one embodiment, is formed by solvent infusion. In one embodiment, the solvent is an alcohol. In a further embodiment, the alcohol is ethanol. "Ethanol infusion" is a type of solvent infusion, and is a process that includes dissolving one or more lipids in a small, minimal, amount of ethanol to form a lipid solution and then adding the solution to an aqueous medium containing bioactive agents. A "small" amount of solvent is an amount compatible with forming liposomes or lipid complexes in the infusion process. The term "solvent infusion" also includes an in-line infusion process where two streams of formulation components are mixed in-line.

The term "symptom" as used herein refers to a phenomenon that arises from and accompanies a particular disease or disorder and serves as an indication of it.

The term "therapeutic effect" refers to a consequence of treatment, the results of which are judged to be desirable and beneficial. A therapeutic effect may include, directly or indirectly, the arrest, reduction, or elimination of a disease manifestation. A therapeutic effect may also include, directly or indirectly, the arrest reduction or elimination of the progression of a disease or condition, or delay in the recurrence of a disease or condition.

The term "treat" or "treating" includes abrogating, substantially inhibiting, slowing or reversing the progression of a disease, condition or disorder, substantially ameliorating clinical or esthetical symptoms of a condition, substantially preventing the appearance of clinical or esthetical symptoms of a disease, condition, or disorder, and protecting from harmful or annoying symptoms. The term "treat" or "treating" as used herein further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in patients that have previously had the disorder(s); and (e) limiting recurrence of symptoms in patients that were previously symptomatic for the disorder(s).

The term "minimum inhibitory concentration" or "MIC" as used herein refers to the lowest concentration of an antimicrobial agent that will inhibit visible growth of a microorganism after overnight incubation (this period is extended for organisms such as anaerobes, which require prolonged incubation for growth). "$MIC_{10}$," "$MIC_{50}$," or "$MIC_{90}$," as used herein, refer to the concentration of an antimicrobial agent that will inhibit growth of the microorganism by 10%, 50%, or 90%, respectively. When no subscript is used, MIC, it is assumed that it is the $MIC_{50}$ that is being discussed. The range of antibiotic concentrations used for determining MICs is accepted universally to be in doubling dilution steps up and down from 1 mg/mL as required (Andrews, J., J. Antimicrob. Chemother., 2001, 48, (Suppl. 1), 5-16, incorporated herein in its entirety).

In one aspect of the invention, a stabilized lipid-based glycopeptide antibiotic composition is provided, comprising a lipid component, a glycopeptide antibiotic and an amino acid or a derivative thereof, wherein the amino acid or derivative thereof is conjugated to the glycopeptide antibiotic. The conjugation of the amino acid or derivative thereof to the glycopeptide antibiotic forms a stabilized glycopeptide antibiotic-amino acid complex. In one embodiment, the glycopeptide antibiotic-amino acid complex is associated with the lipid. For example, in one embodiment, the lipid is conjugated (e.g., bound) to the glycopeptide antibiotic-amino acid complex. In one embodiment, the glycopeptide antibiotic-amino acid complex is entrapped by the lipid component, for example, where the lipid is in the form of a liposome.

The composition described herein, in one embodiment, comprises a liposome, proliposome, lipid colloidal dispersion, micelle, inverted micelle, discoid structure, or a combination thereof. In a further embodiment, the composition comprises a liposome. The glycopeptide antibiotic and amino acid or derivative thereof, in one embodiment, is complexed to the liposome, or encapsulated by the liposome.

"Encapsulated" and "encapsulating" are used to refer to adsorption of active agents on the surface of a lipid based formulation, an association of active agents in the interstitial region of bilayers or between two monolayers, capture of active agents in the space between two bilayers, or capture of active agents in the space surrounded by the inner most bilayer or monolayer.

The lipids used in the compositions of the present invention can be synthetic, semi-synthetic or naturally-occurring lipids, including phospholipids such as phosphatidylglycerols (PGs), phosphatidic acids (PAs), phosphotidylcholines (PCs), phosphatidylinositols (PIs), and phosphatidylserines (PSs); fatty acids; ammonium salts of fatty acids; tocopherols; tocopherol derivatives; sterols; sterol derivatives; and glycerides. The fatty acids have carbon chain lengths of from 12 to 26 carbon atoms, which are either saturated or unsaturated. The lipids can be anionic, cationic, or neutral, where neutral includes both uncharged lipids and zwitterionic lipids. According to one embodiment, the lipid component is substantially free of anionic lipids. According to another embodiment, the lipid component comprises only neutral lipids. According to another embodiment, the lipid component is free of anionic lipids.

According to another embodiment, the lipid in the composition comprises a phospholipid. Phospholipids are comprised of ester linkages of fatty acids in the 2 and 3 of glycerol positions containing chains of 12 to 26 carbon atoms, and different head groups in the 1 position of glycerol that include choline, glycerol, inositol, serine, ethanolamine, as well as the corresponding phosphatidic acids. The chains on these fatty acids can be saturated or unsaturated, and the phospholipid can be made up of fatty acids of different chain lengths and different degrees of unsaturation.

Almost all biologically occurring phospholipids are constructed from combinations of apolar and "backbone" moieties: a glycerol (or other polyol) moiety substituted with one or two acyl or alkyl chains or an N-acylated sphingoid base (i.e., a ceramide). Typically, the hydroxyl group at position 3 of the glycerol is esterified to phosphoric acid, whereas the hydroxyl groups at positions 1 and 2 of the glycerol are esterified with long chain fatty acids, which provide the lipid characteristic of the phospholipid. One of the remaining oxygen groups of phosphoric acid can be esterified further to a variety of organic molecules including glycerol, choline, ethanolamine, serine, and inositol. The phosphate moiety along with the attached alcohol represent the head group of phospholipid. The fatty acid part of a phospholipid is important in that differences in the fatty acid part can change the characteristics of the phospholipid. Fatty acids can differ in the length of their carbon chain (e.g., short, medium, or long chain) and in the level of saturation.

In one embodiment, one or more phospholipids are present in the composition of the present invention. The most abundant phospholipid in plants and animals is phosphatidylcholine (also known as lecithin) and phosphatidylethanolamine, which constitute the major structural part of most biological membranes. In phosphatidylserine, the phosphoric acid moiety is esterified to the hydroxyl group of the amino acid L-serine, whereas, in phosphatidylinositol, the phosphoric acid moiety is esterified to the cyclic sugar alcohol inositol. The other type of phospholipid found in human is phosphatidylglyccrol, which is a natural component of the lung surfactant. In the case of phosphatidylglycerol, the alcohol that is esterified to the phosphate moiety is glycerol instead of phosphoric acid (Vemuri, S. and Rhodes, C., 1995, Pharmaceutica Acta Helvetiae 70: 95-111).

Examples of phospholipids that can be used in the composition of the present invention include, but are not limited to, phosphatidylcholine (PC), phosphatidylglycerol (PG), phosphatidylinositol (PI), phosphatidylserine (PS), phosphatidylethanolamine (PE), phosphatidic acid (PA), egg phosphatidylcholine (EPC), egg phosphatidylglycerol (EPG), egg phosphatidylinositol (EPI), egg phosphatidylserine (EPS), phosphatidylethanolamine (EPE), phosphatidic acid (EPA), soy phosphatidylcholine (SPC), soy phosphatidylglycerol (SPG), soy phosphatidylserine (SPS), soy phosphatidylinositol (SPI), soy phosphatidylethanolamine (SPE), soy phosphatidic acid (SPA), hydrogenated egg phosphatidylcholine (HEPC), hydrogenated egg phosphatidylglycerol (HEPG), hydrogenated egg phosphatidylinositol (HEPI), hydrogenated egg phosphatidylserine (HEPS), hydrogenated phosphatidylethanolamine (HEPE), hydrogenated phosphatidic acid (HEPA), hydrogenated soy phosphatidylcholine (HSPC), hydrogenated soy phosphatidylglycerol (HSPG), hydrogenated soy phosphatidylserine (HSPS), hydrogenated soy phosphatidylinositol (HSPI), hydrogenated soy phosphatidylethanolamine (HSPE), hydrogenated soy phosphatidic acid (HSPA), dipalmitoylphosphatidylcholine (DPPC), dimyristoylphosphatidylcholine (DMPC), dimyristoylphosphatidylglycerol (DMPG), dipalmitoylphosphatidylglycerol (DPPG), distearoylphosphatidylcholine (DSPC), distearoylphosphatidylglycerol (DSPG), dioleoylphosphatidylcholine (DOPC), dioleylphosphatidylethanolamine (DOPE), palmitoylstearoylphosphatidyl-choline (PSPC), palmitoylstearolphosphatidylglycerol (PSPG), mono-oleoyl-phosphatidylethanolamine (MOPE), tocopherol, tocopherol hemisuccinate, cholesterol sulfate, cholesteryl hemisuccinate, cholesterol derivatives, ammonium salts of fatty acids, ammonium salts of phospholipids, ammonium salts of glycerides, myristylamine, palmitylamine, laurylamine, stearylamine, dilauroyl ethylphosphocholine (DLEP), dimyristoyl ethylphosphocholine (DMEP), dipalmitoyl ethylphosphocholine (DPEP) and distearoyl ethylphosphocholine (DSEP), N-(2,3-di-(9-(Z)-octadecenyloxy)-prop-1-yl-N,N,N-trimethylammonium chloride (DOTMA), 1,2-bis(oleoyloxy)-3-(trimethylammonio) propane (DOTAP), distearoylphosphatidylglycerol (DSPG), dimyristoylphosphatidylacid (DMPA), dipalmitoylphosphatidylacid (DPPA), distearoylphosphatidylacid (DSPA), dimyristoylphosphatidylinositol (DMPI), dipalmitoylphosphatidylinositol (DPPI), distearoylphospatidylinositol (DSPI), dimyristoylphosphatidylserine (DMPS), dipalmitoylphosphatidylserine (DPPS), distearoylphosphatidylserine (DSPS), or a mixture thereof.

In one embodiment, the composition comprises DPPC and/or DPPG.

According to another embodiment, the phospholipid used in the composition of the present invention is a mixed phospholipid, including, but not limited to, palmitoylstearoylphosphatidylcholine (PSPC) and palmitoylstearoylphosphatidylglycerol (PSPG)), triacylglycerol, diacylglycerol, ceramide, sphingosine, sphingomyelin, and single acylated phospholipids, such as mono-oleoyl-phosphatidylethanol amine (MOPE).

In one embodiment, the lipid component of the present invention comprises one or more sterols. In a further embodiment, the sterol is cholesterol. The sterols, of which cholesterol and its derivatives are the most widely studied in mammalian systems, constitute a component of membrane lipids, along with the glycerophospholipids and sphingomyelins (Bach et al., 2003, Biochem. Biophys. Acta., 1610: 187-197). Sterol lipids are subdivided primarily on the basis of biological function. There are many examples of unique sterols from plant, fungal, and marine sources that are designated as distinct subclasses of sterols. These are subdivided on the basis of the number of carbons in the core skeleton. The $C_{18}$ sterols include the estrogen family, whereas the $C_{19}$ sterols comprise the androgens, such as testosterone and androsterone. The $C_{21}$ subclass, containing a two carbon side chain at the $C_{17}$ position, includes the progestogens as well as the glucocorticoids and mineralocorticoids. The secosterols, comprising various forms of vitamin D, are characterized by cleavage of the B ring of the core structure, hence the "seco" prefix. Additional classes within the sterols category are the bile acids, which in mammals are primarily derivatives of cholan-24-oic acid synthesized from cholesterol in the liver and their conjugates (sulfuric acid, taurine, glycine, glucuronic acid, and others) (Fahy, E. et al., 2005, J. Lipid Res., 46:839-861). Each of the publications referenced in this paragraph are incorporated by reference herein in their entireties.

As provided herein, in one embodiment, the lipid component of the present invention comprises cholesterol. Cholesterol is found in animal membranes and has been used in the preparation of liposomes to improve bilayer characteristics of the liposomes. The cholesterol molecule orients itself among the phospholipid molecules with its hydroxyl group facing towards the water phase, the tricyclic ring sandwiched between the first few carbons of the fatty acyl chains, into the hydrocarbon core of the bilayer (Vemuri, S. and Rhode, C., Pharmacecutica Acta Helvetiae, 1995, 70: 95-111). Cholesterol improves the fluidity of the bilayer membrane, reduces the permeability of water soluble molecules through the membrane, and improves the stability of the bilayer membrane in the presence of biological fluids such as blood/plasma. Liposomes without cholesterol tend to react with blood proteins, such as albumin, m-transferrin, and macroglobulin, which tend to destabilize the liposomes and reduce the utility of liposomes as drug delivery systems.

According to another embodiment, the lipid component consists essentially of a phosphatidylcholine. According to another embodiment, the lipid component consists essentially of dipalmitoylphosphatidylcholine (DPPC). According to another embodiment, the lipid component consists essentially of palmitoyloleoylphosphatidylcholine (POPC).

According to another embodiment, the lipid component consists essentially of phosphatidylglycerol. According to another embodiment, the lipid component consists essentially of 1-palmitoyl-2-oleoyl-sn-glycero-3-phosphoglycerol (POPG).

According to one embodiment, the stabilized glycopeptide antibiotic is entrapped by or complexed with the lipid component. In one embodiment, the lipid component is in the form of a liposome. Liposomes are completely closed lipid bilayer membranes containing an entrapped aqueous volume. It has been reported that liposomes spontaneously form when phospholipids are dispersed in aqueous medium (Bangham et al., 1974, In Korn, E. D. ed., Methods in Membrane Biology, Vol. 1. Plenum Press, New York, pp. 1-68, incorporated by reference herein in its entirety). The hydrophilic interaction of the lipid head groups with water results in the formation of vesicles composed of simple lipid bilayers that resemble biological membranes, in the form of a spherical shell. Liposomes can be unilamellar vesicles (possessing a single membrane bilayer) or multilamellar vesicles (onion-like structures characterized by multiple membrane bilayers, each separated from the next by an aqueous layer), or a combination thereof. The bilayer is composed of two lipid monolayers having a hydrophobic "tail" region and a hydrophilic "head" region. The structure of the membrane bilayer is such that the hydrophobic (nonpolar) "tails" of the lipid monolayers orient toward the center of the bilayer while the hydrophilic "heads" orient towards the aqueous phase.

Depending on the method of preparation, liposomes of the invention vary widely in size (e.g., 0.02-10 μm) and in the number of lamellae (i.e., number of bilayers present within a liposome). Typically, liposomes are classified into three categories on the basis of their size and lamellarity: small unilamellar vesicles (SUVs), small oligolamellar vesicles (OLVs), large unilamellar vesicles (LUVs), and multilamellar vesicles (MLVs). More detailed classification based on structure is shown in Table 1. (Smad, A. et al., Current Drug Delivery, 2007, 4: 297-305, incorporated by reference herein in its entirety).

According to one embodiment, the pharmaceutical composition comprises a liposome or a plurality of liposomes. The glycopeptides antibiotic and amino acid (or derivative thereof) is entrapped by the liposome (or plurality of liposomes), complexed to the liposome (or plurality of liposomes), for example, complexed to the bilayer of the liposome, or a combination of entrapped and complexed.

In one embodiment, the liposome is a unilamellar vesicle (UV). According to further embodiment, the liposome is a small unilamellar vesicle (SUV), a medium unilamellar vesicle (MUV), a large unilamellar vesicle (LUV) or a giant unilamellar vesicle (GUV). According to another embodiment, the liposome is an oligolamellar vesicle (OV). According to another embodiment, the plurality of liposomes comprise liposome is a multilamellar vesicle (MV) and unilamellar vesicles. According to another embodiment, the liposome comprises a multilamellar vesicle (MV).

TABLE 1

Vesicle Types with their Size and Number of Lipid layers

| Vesicle Type | Abbreviation | Diameter | Number of Lipid Bilayer |
|---|---|---|---|
| Unilamellar vesicle | UV | All size ranges | One |
| Small Unilamellar vesicle | SUV | 20-100 nm | One |
| Medium Unilamellar vesicle | MUV | >100 nm | One |
| Large Unilamellar vesicle | LUV | >100 nm | One |
| Giant Unilamenar vesicle | GUV | >1 μm | One |
| Oligolamellar vesicle | OLV | 0.1-1 μm | Approximately 5 |
| Multilamellar vesicle | MLV | >1 μm | 5-25 |
| Multi vesicular vesicle | MV | >1 μm | Multi compartmental structure |

According to one embodiment, the liposome has a mean particle size of about 0.05 to about 10 microns, 0.05 to about 1 microns, 0.05 to about 0.5 microns, about 0.1 to about 5.0 microns, about 0.1 to about 3.0 microns, about 0.1 to about 2.0 microns, about 0.1 to about 1.0 microns, about 0.1 to about 0.5 microns, about 0.1 to about 0.4 microns, about 0.1 to about 0.3 microns, or about 0.1 to about 0.2 microns. In another embodiment, the mean particular size of the liposome is about 1.0 microns or less, about 0.9 microns or less, about 0.8 microns or less, about 0.7 microns or less, about 0.6 microns or less, about 0.5 microns or less, about 0.4 microns or less, about 0.3 microns or less, or about 0.2 microns or less.

According to one embodiment, the lipid component of the present invention is in the form of a micelle or plurality of micelles. Many surfactants can assemble in a bulk solution into aggregates or micelles. The concentration at which surfactants begin to form micelles is known as the "critical micelle concentration" ("CMC"). The lipid in the compositions provided herein, in one embodiment, is a surfactant with an extremely low CMC.

According to another embodiment, the stabilized glycopeptide antibiotic is entrapped by a lipid clathrate. A lipid clathrate is a three-dimensional, cage-like structure employing one or more lipids wherein the structure entraps a bioactive agent. Such clathrates are included in the scope of the present invention.

According to anther embodiment, the stabilized glycopeptide antibiotic is entrapped by a proliposome or plurality of proliposomes. Proliposomes are formulations that can become liposomes or lipid complexes upon coming in contact with an aqueous liquid, and include for example dry powders. Agitation or other mixing may be necessary. Such proliposomes are included in the scope of the present invention.

The tissue distribution and clearance kinetics of drug-containing liposomes are known to be affected by lipid composition and surface charge (Juliano and Stamp, Biochem. Biophys. Res. Commun., 1975, 63: 651, incorporated by reference herein in its entirety). There are a number of synthetic phospholipids available and utilized in the preparation of liposomes. Gangliosides, a class of sphingolipids, sometimes are included in liposome formulations to provide a layer of surface charged groups, which provide longer circulating liposomes in the blood stream. Such liposome formulations comprising sphingolipids are included in the scope of the present invention.

The composition of the present invention includes one or more glycopeptides antibiotics. Glycopeptide antibiotics, including vancomycin and teicoplanin, are large, rigid molecules that inhibit a late stage in bacterial cell wall peptidoglycan synthesis. Glycopeptides are characterized by a multi-ring peptide core containing six peptide linkages, an unusual triphenyl ether moiety, and sugars attached at various sites. Over 30 antibiotics designated as belonging to the glycopeptide class have been reported. Among the glycopeptides, vancomycin and teicoplanin are used widely and are recommended for treatment of severe infections, especially those caused by multiple-drug-resistant Gram-positive pathogens. The glycopeptide avoparcin has been introduced as a growth promoter in animal husbandry in the past, and represents the main reservoir for the VanA type of vancomycin resistance in enterococci. Semisynthetic derivatives of vancomycin and teicoplanin, lipoglycopeptides, showed an extended spectrum of activity against multi-resistant and partly vancomycin-resistant bacteria (Reynolds P., Eur. J. Clin Microbiol Infect Dis, 1989, 8: 943-950; Renolds, 1989; Nordmann et al., Curr. Opin. Microbiol., 2007, 10: 436-440). Each of the publications referenced in this paragraph are incorporated by reference herein in their entireties.

Glycopeptide antibiotics are active against Gram-positive organisms and a few anaerobes. The main indications for glycopeptide antibiotics are infections caused by beta-lactamase-producing *Staphylococcus aureus* (for which beta-lactamase-resistant penicillins, cephalosporins, and combinations of penicillins with inhibitors of beta-lactamases proved safer alternatives), and colitis caused by *Clostridium difficile*. The emergence and rapid spread of methicillin-resistant *S. aureus* (MRSA) strains, which were resistant not only to all beta-lactams but also to the main antibiotic classes, renewed the interest in vancomycin and pushed teicophalnin, another natural glycopeptide, onto the market. Teicoplanin is comparable to vancomycin in terms of activity, but presents pharmacokinetic advantages, such as prolonged half-life, allowing for a once-daily administration (van Bambeke F., Curr. Opin. Pharm., 4(5):471-478).

Prior to 1984, the glycopeptide class included few members beyond vancomycin, teicoplanin, ristocetin, and avoparcin. With the acknowledgement of the threat posed by antibiotic resistance, the class expanded to include thousands of natural and semi-synthetic compounds. Structural studies on these compounds have clarified the biological mode of action and have served as a basis for reasonable predictions regarding structure-activity relationships.

The structures of hundreds of natural and semisynthetic glycopeptides have been determined. These structures are highly related and fall within five structural subtypes, I-V. Of the varying structural subtypes, type I structures contain aliphatic chains, whereas types II, III, and IV include aromatic side chains within these amino acids. Unlike types I and II, types III and IV contain an extra F-O-G ring system. Type IV compounds have, in addition, a long fatty-acid chain attached to the sugar moiety. Structures of type V, such as complestatin, chloropeptin I, and kistamincin A and B, contain the characteristic tryptophan moiety linked to the central amino acid. The structures of the subtypes are known in the art and described in Nicolaou et al. (Angew. Chem. Int. Ed., 1999, 38: 2096-2152, incorporated by reference herein in its entirety), the entire contents of which are incorporated herein by reference. Compounds of each of the structural subtypes mentioned above can be used in the compositions described herein.

Biochemical studies of the mode of action of glycopeptide antibiotics indicate that these substances inhibit cell wall peptidoglycan synthesis. Treatment of intact bacteria with vancomycin at concentrations close to the minimum inhibitory concentration (MIC) resulted in the accumulation of cytoplasmically located wall precursors (Reynolds et al., Biochimica et Biophysica Acta. 1961, 52: 403-405; Jordan. Biochemical and Biophysical Research Communications, 1961, 6: 167-170), suggesting that glycopeptides interfered with a late stage in the assembly of the peptidoglycan. Vancomycin, and other glycopeptides, cannot penetrate the cytoplasmic membrane (Perkins et al., Biochemical Journal, 1970, 116: 83-92), and thus the critical transglycosylation reaction is the first to be inhibited (Jordan and Reynolds: Vancomycin. In: Corcoran, J. W., Hahn, F. E. (ed.): Antibiotics, volume III. Mechanism of action of antimicrobial and antitumor agents. Springer-Verlag, Berlin, 1974, 704-718). Inhibition of this reaction results in the accumulation of lipid intermediates in the biosynthetic pathway and of UDP-MurNAc-pentapeptide in the cytoplasm. Each of the publications referenced in this paragraph are incorporated by reference herein in their entireties.

Glycopeptide antibiotics tend to be unstable in solution, resulting in a loss of activity. Stability of glycopeptides can be enhanced using one of the two peptides Ac-D-Ala-D-Ala and Di-Ac-L-Lys-D-Ala-D-Ala (Harris et al., 1985, J. Antibiot, 38(1):51-7, incorporated by reference herein in its entirety). However, a need exists for more improvement in stability of glycopeptide antibiotics, preferably in a cost-effective manner. Unexpectedly, the compositions of the present invention, comprising a glycopeptide antibiotic, an amino acid or derivative thereof, and a lipid component, exhibited superior stability compared glycopeptide antibiotic compositions that are not lipid-based and/or do not comprise an amino acid or derivative thereof.

A representative number of glycopeptides that can be used in the compositions of the present invention are provided in Table 2. The antibiotic complexes are listed in alphabetical order along with the structure type producing organism. These metabolites are elaborated by a diverse group of actinomycetes ranging from the more prevalent *Streptomyces* species to the relatively rare genera of *Streptosporangium* and *Saccharomonospora*. The less common *Actionplanes* and *Amycolatopsis* account for almost half of the producing organisms (Nagarajan, R., Glycopeotide Antibiotics, CRC Press, 1994, incorporated by reference herein in its entirety).

TABLE 2

Glycopeptide Antibiotics and Producing Organisms

| Antibiotic | Type | Producing Organism |
|---|---|---|
| A477 | ND | *Actinoplanes* sp. NRRL 3884 |
| A35512 | III | *Streptomyces candidus* NRRL 8156 |
| A40926 | IV | *Actinomadura* sp. ATTC39727 |
| A41030 | III | *Streptomyces virginiae* NRRL 15156 |
| A42867 | I | *Nocardia* sp. ATTC 53492 |
| A47934 | III | *Streptomyces toyocaensis* NRRL 15009 |
| A80407 | III | *Kibdelosporangium philippinensis* NRRL 18198 or NRRL 18199 |
| A82846 | I | *Amycolatopsis orientalis* NRRL 18100 |
| A83850 | I | *Amycolatopsis albus* NRRL 18522 |
| A84575 | I | *Streptosporangium carneum* NRRL 18437, 18505 |
| AB-65 | ND | *Saccharomonospora viride* T-80 FERM-P 2389 |
| Actaplanin | III | *Actinoplanes missouriensis* ATCC 23342 |
| Actinoidin | II | *Proactinomyces actinoides* |
| Ardacin | IV | *Kibdelosporangium aridum* ATCC 39323 |
| Avoparcin | II | *Streptomyces candidus* NRRL 3218 |

TABLE 2-continued

Glycopeptide Antibiotics and Producing Organisms

| Antibiotic | Type | Producing Organism |
|---|---|---|
| Azureomycin | ND | *Pseudonocardia azurea* NRRL11412 |
| Chloroorienticin | I | *Amyclolatopsis orientalis* PA-45052 |
| Chloropolysporin | II | *Micropolyspora* sp. FERM BP-538 |
| Decaplanin | I | *Kibdelosporangium deccaensis* DSM 4763 |
| N-demethylvancomycin | I | *Amycolatops orientalis* NRRL 15252 |
| Eremomycin | I | *Actinomycetes* sp. INA 238 |
| Galacardin | II | *Actinomycetes* strain SANK 64289 FERM P-10940 |
| Helvecardin | II | *Pseudonocardia compacta* subsp. *helvetica* |
| Izupeptin | ND | Norcardia AM-5289 FERM P-8656 |
| Kibdelin | IV | *Kibdelosporangium aridum* ATCC 39922 |
| LL-AM374 | ND | *Streptomyces eburosporeus* NRRL 3582 |
| Mannopeptin | ND | *Streptomyces platenis* FS-351 |
| MM45289 | I | *Amycolatopsis orientalis* NCIB12531 |
| MM47761 | I | *Amycolatopsis orientalis* NCIB 12608 |
| MNI47766 | II | *Amycolatopsis orientalis* NCBI 40011 |
| MM55266 | IV | *Amycolatopsis* sp. NCIB 40089 |
| MM55270 | ND | *Amycolatopsis* sp. NCIB 40086 |
| OA-7653 | I | *Streptomyces hygromscopicus* ATCC 31613 |
| Orienticin | I | *Nocardia orientalis* FERM BP-1230 |
| Parvodicin | IV | *Actinomadura parvosata* ATCC 532463 |
| Ristocetin | III | *Amycolatopsis orientalis* subsp. *lurida* NRRL 2430 |
| Ristomycin | III | *Proactinomyces fructiferi* |
| Synmonicin | II | *Synnemomyces mamnoorii* ATCC 53296 |
| Teicoplanin | IV | *Actinoplanes teichomyceticus* ATCC 31121 |
| UK-68597 | III | *Actinoplanes* ATCC 53533 |
| UK-69542 | III | *Saccharothix aerocolonigenes* |
| UK-72051 | I | *Amycolatopsis orientalis* |
| Vancomycin | I | *Amycolatoposis orientalis* NRRL 2450 |

According to another embodiment, the glycopeptide antibiotic used in the composition of the present invention includes, but is not limited to, A477, A35512, A40926, A41030, A42867, A47934, A80407, A82846, A83850, A84575, AB-65, Actaplanin, Actinoidin, Ardacin, Avoparcin, Azureomycin, Chloroorienticin Chloropolysporin, Decaplanin, N-demethylvancomycin, Eremomycin, Galacardin. Helvecardin Izupeptin, Kibdelin, LL-AM374, Mannopeptin, MM45289, MM47761, MM47766, MM55266, MM55270, OA-7653, Orienticin, Parvodicin, Ristocetin, Ristomycin, Synmonicin, Teicoplanin, UK-68597, UK-69542, UK-72051, vancomycin, and a mixture thereof.

According to one embodiment, the glycopeptide antibiotic of the present invention is vancomycin. Vancomycin is a water soluble amphoteric glycopeptide bactericidal antibiotic that inhibits gram-positive bacterial mucopeptide biosynthesis. It consists of a tricyclic nonribosomal heptapeptide core structure to which is attached a disaccharide unit consisting of the aminodeoxy sugar, vancosamine, and D-glucose (FIG. 1). This natural antibiotic of ~1450 Daltons is obtained from *Streptomyces orientalis* (also known as; *Norcardia orientalis*, or *Amycolatopsis orientalis*). Vancomycin has one carboxyl group with pKa 2.18, and two amino groups: primary amine with pKa 7.75 and the secondary amine with pKa 8.89. At sub-physiological pH vancomycin has a net positive charge.

Although vancomycin has been reported to be bactericidal, it is not necessarily the case that the bacteria are killed. Without wishing to be bound by theory, the bacteria are instead prevented from growing by the saturation of the available growth points of the peptidoglycan. The non-covalent nature of the binding of vancomycin to the important target sites is indicated by the ease with which the inhibition of either bacterial growth or peptidoglycan synthesis could be reversed. Such reversal has been accomplished by the addition to the growth or incubation medium of a suitable peptide that competed effectively with the natural wall peptides at the growth points for the available glycopeptide (Nieto, M. et al., Biochemical Journal, 1972, 126: 139-149, incorporated by reference herein).

Studies have shown that vancomycin binds reversibly to the L-Lys-D-Ala-D-Ala fragment of the peptidoglycan monomer. This reversible, noncovalent interaction inhibits transglycosidation and transpeptidation from occurring. Inhibition of these processes leads to the collapse of the peptidoglycan by decisively shifting its dynamic equilibrium towards de-assembly, which precipitates cell lysis and bacterial death.

The strong binding of vancomycin to L-Lys-D-Ala-D-Ala is a consequence of five well-defined hydrogen bonds. In Gram-positive bacteria, the glycopeptide antibiotics easily diffuse through the peptidoglycan layer and reach the periplastic space where the peptidoglycan polymerization takes place. By grabbing onto the L-Lys-D-Ala-D-Ala tails of the monomers the antibiotic positions itself to inhibit the transglycosidase from joining the carbohydrate.

Figure 2:
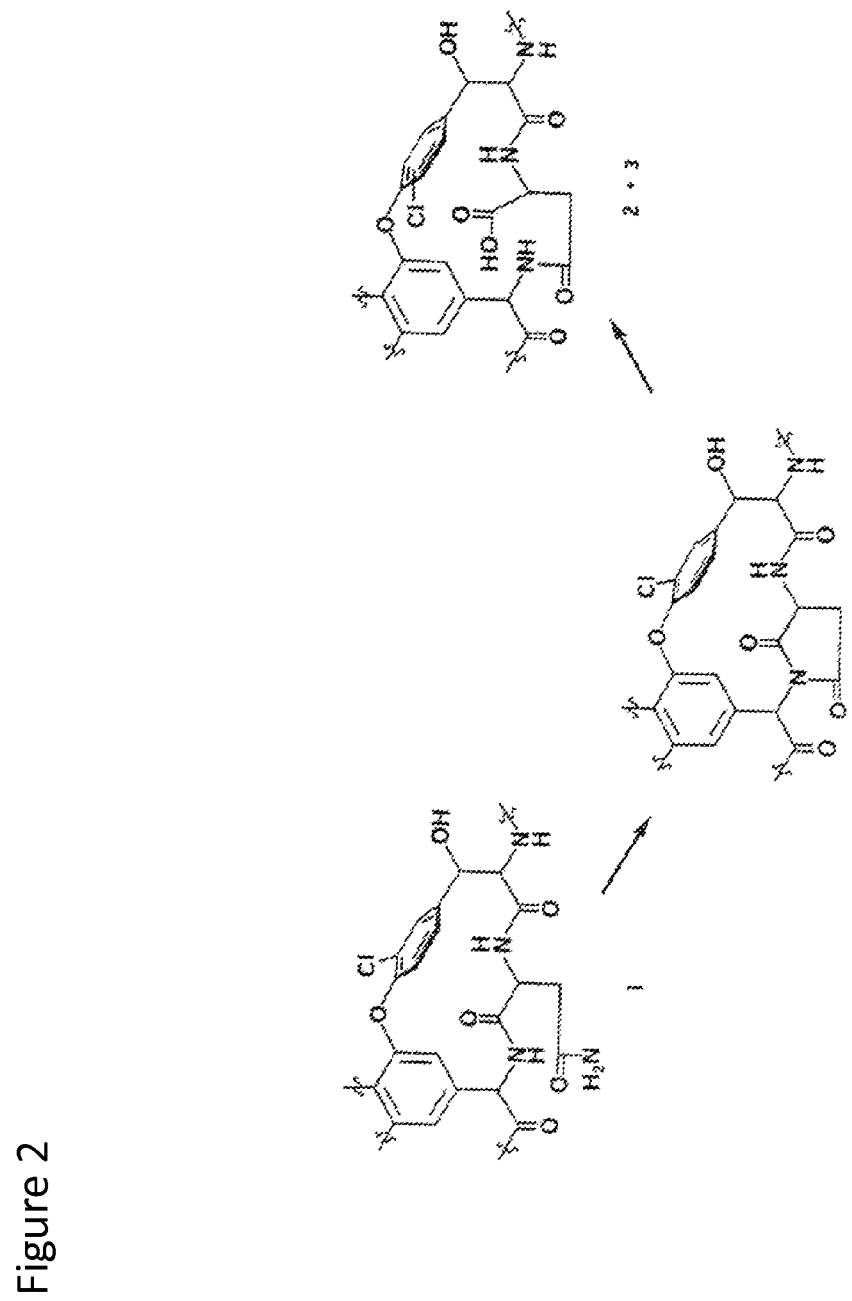
FIG. 2 shows the structural changes during vancomycin degradation to Crystalline Degradation Product-I (CDP-I).

Due to the nature of the manufacturing process for vancomycin, the raw material usually contains a number of impurities. In addition, vancomycin is not very stable in solution and degrades to several products, known as product degradants. It is believed that the main degradation product of vancomycin is crystalline degradation product one (CDP-I), and results from deamidation of an asparagine residue. The structural changes during vancomycin degradation to CDP-I are shown in FIG. 2. CDP-I has limited aqueous solubility and exists in two isomeric forms often referred to as CDP-I-m (minor) and CDP-I-M (major). These are the atropisomers involving different orientations of the CI substituted aromatic ring of residue 2. The order of the CDP formation is thought to be: vancomycin→succinimide intermediate→CDP-I-m→CDP-I-M (Harris, C. et al., 1983, Journal of the American Chemical Society, 105 (23):6915-6922, incorporated by reference herein). In equilibrium, the ratio of the two forms in solution is approximately 1:2 and the equilibrium time is 24 hours at pH 6.5 at 25° C. CDP-I can be converted further into crystalline hydrochloride CDP-II by incubating with 0.6N HCl (Marshall, 1965. J. Med Chem, 8:18-22, incorporated by reference herein in its entirety). CDP-II seems to not form in measurable quantities under normal conditions.

Figure 3:
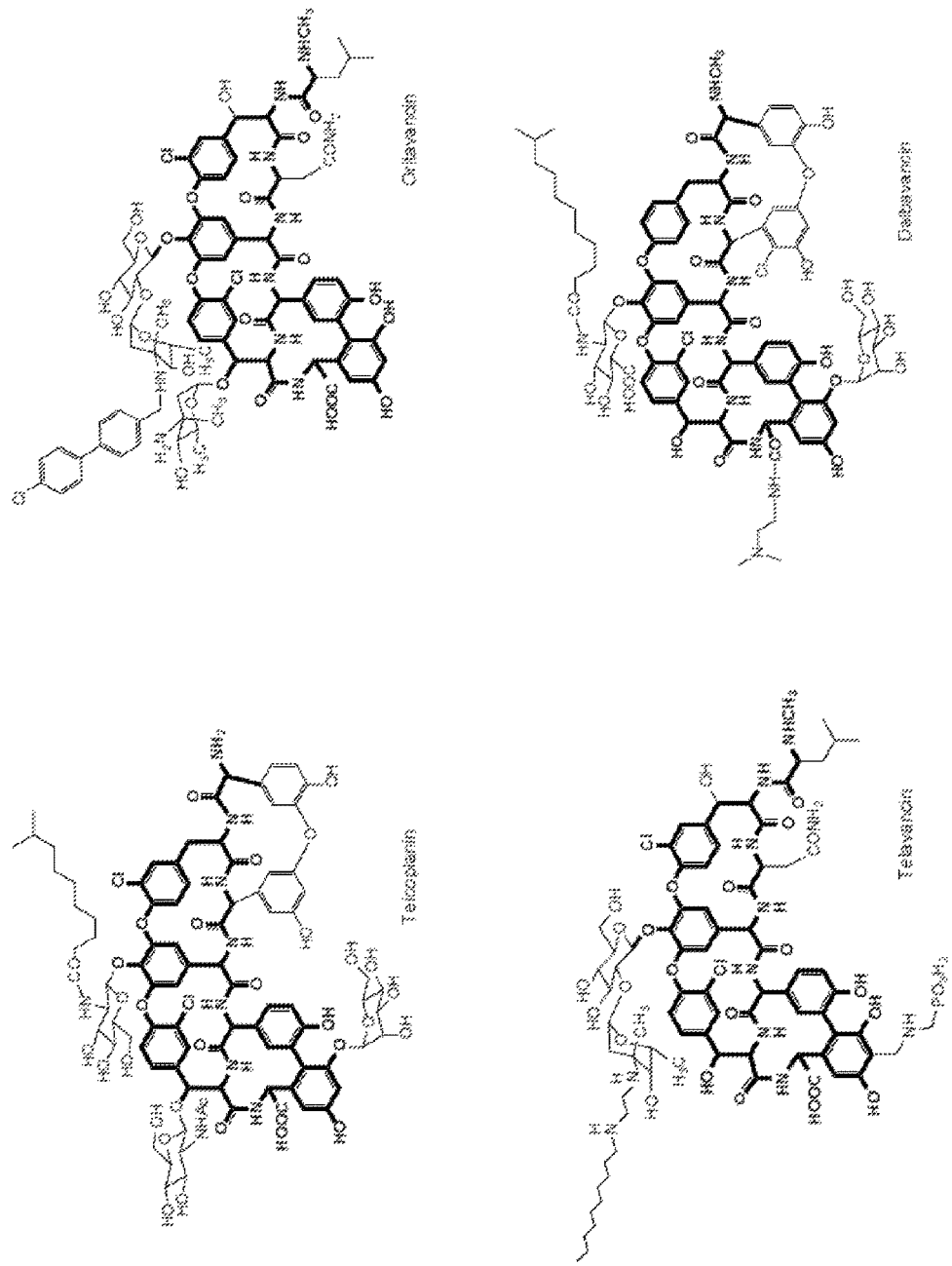
FIG. 3 shows the general structure of four types of natural glycopeptide antibiotics.

According to one embodiment, the glycopeptide antibiotic of the present invention is oritavancin (LY333328). Oritavancin is obtained by reductive alkylation with 4' chloro-biphenylcarboxaldehyde of the natural glycopeptide chloroeremomycin, which differs from vancomycin by the addition of a 4-epi-vancosamine sugar and the replacement of the vancosamine by a 4-epivancosamine (Cooper, R. et al., J Antibiot (Tokyo) 1996, 49:575-581, incorporated by reference herein in its entirety). The structure of oritavancin is shown in FIG. 3. Although oritavancin presents a general spectrum of activity comparable to that of vancomycin, it offers considerable advantages in terms of intrinsic activity (especially against streptococci), and remains insensitive to the resistance mechanisms developed by staphylococci and *enterococci*. Because the binding affinity of vancomycin and oritavancin to free D-Ala-D-Ala and D-Ala-D-Lac are of the same order of magnitude, the difference in their activity has been attributed to the cooperative interactions that can occur between the drug and both types of precursors in situ. The previous study suggested that the effect is caused possibly by a much stronger ability to dimerize and the anchoring in the cytosolic membrane of the chlorobiphenyl side chain (Allen, et al., FEMS Microbiol Rev, 2003, 26:511-532, incorporated by reference herein).

The efficacy of oritavancin has been demonstrated in animal models of meningitis caused by pneumococci susceptible or resistant to β-lactams (even though the concentration in cerebrospinal fluid is only 5% of the serum level) (Gerber et al., Antimicrob Agents Chemother, 2001, 45:2169-2172, incorporated by reference herein in its entirety; Cabellos et al., Antimicrob Agents Chemother, 2003, 47:1907-1911, incorporated by reference herein in its entirety); in models of central venous catheter-associated infection by vancomycin-resistant *Enterococcus faecium* (Rupp et al., J Antimicrob Chemother 2001, 47:705-707, incorporated by reference herein in its entirety); and in models of endocarditis caused by vancomycin-susceptible or -resistant *Enterococcus faecalis* (Lefort et al., Antimicrob Agents Chemother, 2000, 44:3017-3021, incorporated by reference herein in its entirety). Pharmacodynamic studies in a neutropenic mouse thigh model of *S. aureus* infection suggested that the parameter that best predicts oritavancin efficacy is the ratio between the free $C_{max}$ concentration and the minimal inhibitory concentration (MIC) of the offending organism (free Cmax/MIC) (Boylan, C. et al., Antimicrob Agents Chemother, 2003, 47:1700-1706). Additional favorable pharmacodynamic characteristics include prolonged post-antibiotic effects, and synergy with 3-lactams or aminoglycosides (Lefort et al., Antimicrob Agents Chemother, 2000, 44:3017-3021, incorporated by reference herein; Baltch et al., Antimicrob Agents Chemother 1998, 42:2564-2568, incorporated by reference herein in its entirety).

Accordingly, oritavancin can be classified as a highly concentration-dependent bactericidal antibiotic with prolonged persistent effects, in the same way as aminoglycosides and, to some extent, quinolones (Craig, Infect Dis Clin North Am, 2003, 17:479-501, incorporated by reference herein in its entirety). This pharmacodynamic profile contrasts with that of conventional glycopeptides for which efficacy relies mainly upon the area under the curve/MIC ratio, because they show time-dependent activity and persistent effects (Craig, Infect Dis Clin North Am, 2003, 17:479-501, incorporated by reference herein in its entirety).

One pharmacokinetic property of oritavancin is its prolonged retention in the organism, which destines it to a once-a-day scheme of administration. The exceptionally long terminal half-life suggests the existence of storage sites within the organism. Studies on cultured macrophages indicated that the drug accumulates slowly (by an endocytic process) but importantly in the lysosomes, from which its efflux is extremely slow. This explains why it is bactericidal against intracellular forms of *Staphylococcus* or *Enterococcus* infections, but not against cytosolic bacteria such as *Listeria monocytogenes* (Al Nawas et al., Infection 2000, 28:214-218, incorporated by reference herein in its entirety; Seral et al., Antimicrob Agents Chemother, 2003, 47:2283-2292v). Corroborating these data, a recent study in volunteers demonstrated that oritavancin reaches high concentrations not only in epithelial lining fluid but also in alveolar macrophages (Rodvold et al., Clin Microbiol Infect 2004, incorporated by reference herein in its entirety).

According to one embodiment, the glycopeptide antibiotic of the present invention is telavancin (TD-6424). Telavancin is a semi-synthetic derivative of vancomycin, possessing a hydrophobic side chain on the vancosamine sugar (decylaminoethyl) and a (phosphonomethyl) aminomethyl substituent on the cyclic peptidic core (FIG. 3; van Bambeke. F., Curr. Opin. Pharm., 4(5): 471-478; Judice, J. et al., Bioorg Med Chem Lett 2003, 13: 4165-4168, incorporated by reference herein in its entirety). The length of the hydrophobic side chain was chosen to reach a compromise between optimized activity against MRSA (8-10 carbons) and VanA *enterococci* (12-16 carbons). Pharmacological studies suggest that the enhanced activity of telavancin on *S. pneumoniae, S. aureus* (to a lesser extent), and staphylococci or *enterococci* harboring the vanA gene cluster results from a complex mechanism of action which, on the basis of data obtained with close analogs, involves a perturbation of lipid synthesis and possibly membrane disruption.

The polar substituent introduced on the resorcinol moiety improves the distribution of the molecule in the body and counterbalances the prolonging effect of the lipophilic side chain on the half-life, which is now approximately 7 h and still compatible with a once-daily administration. Pharmacodynamic properties include a prolonged post-antibiotic effect and a concentration-dependent bactericidal activity; therefore, one would propose to calculate the pharmacodynamic breakpoint on the basis of the free $C_{max}$/MIC ratio, as done for oritavancin.

According to one embodiment, the glycopeptide antibiotic of the present invention is dalbavancin (BI 397). Dalbavancin is a semi-synthetic derivative of A40926, a glycopeptide with a structure related to that of teicoplanin (FIG. 3; Malabarba et al., Curr Med Chem 2001, 8:1759-1773, incorporated by reference herein in its entirety; Malabarba et al., J Antibiot (Tokyo) 1994, 47:1493-1506, incorporated by reference herein in its entirety).

As with oritavancin and telavancin, dalbavancin is more active against *S. pneumoniae* than are conventional glycopeptides, and its activity against *S. aureus* is also substantially improved, which was not observed with the semisynthetic derivatives of vancomycin. However, studies have shown that it is not more active than teicoplanin against *enterococci* harboring the VanA phenotype of resistance to glycopeptides. Dalbavancin is also characterized by a marked bactericidal character and a synergism with penicillin. The pharmacodynamic breakpoint calculated (as for the other bactericidal glycopeptides) on the basis of the free $C_{max}$/MIC ratio is of the same order of magnitude. Pharmacokinetic parameters and pharmacodynamic breakpoints for glycopeptides at doses pertinent to their use in humans (or the foreseen doses for molecules in development) are shown in Table 3. Dalbavancin showed such a prolonged half-life that its plasma concentration exceeds the minimal bactericidal concentration of target organisms even at one week after administration of a single 1000 mg dose; free levels, however, are close to the MICs at these conditions (Steiert, M. et al., Curr Opin Investig Drugs 2002, 3:229-233, incorporated by reference herein in its entirety). These results indicate that a single dose of dalbavancin significantly reduces the bacterial load in animal models of granuloma pouch infection by MRSA (Jabes et al., Antimicrob Agents Chemother 2004, 48:1118-1123, incorporated by reference herein in its entirety), endocarditis by vancomycin-susceptible or -intermediate staphylococci (Lefort et al., Antimicrob Agents Chemother 2004, 48:1061-1064, incorporated by reference herein in its entirety), or pneumonia by penicillin-resistant pneumococci (Candiani et al., 41th Interscience Conference on Antimicrobial Agents and Chemotherapy 2001, Chicago, Ill. [Abstract 989], incorporated by reference herein in its entirety).

TABLE 3

Pharmacokinetic parameters and pharmacodynamic breakpoints for glycopeptides
(van Bambeke, Curr. Opin. Pharm., 2004, 4: 471-78, incorporated by reference herein)

| Parameter (units) | Glycopeptide and dosage | | | | |
|---|---|---|---|---|---|
| | Vancomycin (15 mg/kg) | Oritavancin (3 mg/kg) | Telavancin (7.5 mg/kg) | Teicoplanin (6 mg/kg) | Dalbavancin (15 mg/kg) |
| $C_{max}$ (mg/L) | 20-50 | 31 | 89 | 43 | 312 |
| $V_d$ (L/kg) | 0.3 | | 0.1 | 0.9-1.6 | 0.11 |
| Protein binding (%) | 10-55 | 90 | 90-93 | 90 | 98 |
| Terminal half-life (h) | 4-8 | 360 | 7 | 83-168 | 149 |
| AUC (mg · h/L) | 260 | 152 | 600 | 550 | 27103 |
| PD breakpoint based on (free AUC)/MIC ratio | 2 (15 mg/kg twice-daily) | 0.1 (3 mg/kg) 0.3 (10 mg/kg) | 0.5 | 0.4 (6 mg/kg), | 4 |
| PD breakpoint based on (free $C_{max}$)/MIC ratio | | 0.3 (3 mg/kg) 1 (10 mg/kg) | 1 | | 0.6 |

According to one embodiment, the glycopeptide antibiotic if the present invention is conjugated to an amino acid or a derivative thereof. In as further embodiment, conjugation of the glycopeptides is to the N terminus or C terminus of the amino acid or derivative thereof. In another embodiment, the glycopeptides antibiotic is conjugated to the amino acid side chain.

In one embodiment, the conjugation of the amino acid or derivative thereof to the glycopeptide antibiotic forms a stabilized glycopeptide antibiotic-amino acid complex. In one embodiment, the stabilized glycopeptide antibiotic-amino acid complex is associated with a lipid. For example, in one embodiment, the lipid is conjugated (e.g., bound) to the glycopeptide antibiotic-amino acid complex. In one embodiment, the glycopeptide antibiotic-amino acid complex is entrapped by the lipid component, for example, where the lipid is in the form of a liposome or plurality of liposomes.

In one embodiment, the stabilized glycopeptide antibiotic composition of the described invention includes an amino acid or derivative thereof. In one embodiment, the amino acid or derivative thereof is selected from the group consisting of alanine (ALA), D-alanine (D-ALA), alanine-alanine (ALA-ALA), beta-alanine (bALA), 3-aminobutanoic acid (3-ABA), gamma-aminobutyric acid (GABA), glutamic acid (GLU), D-glutamic acid (D-GLU), glycine (GLY), glycylglycine (GLY-GLY), aspartic acid (ASP), D-aspartic acid (D-ASP), bicine, tricine, sarcosine, iminodiacetic acid (IDAA), and combinations thereof. Structures of exemplary amino acids or derivatives thereof useful in the invention are shown below in Table 4.

TABLE 4

Structure of exemplary amino acids and derivatives thereof

| Amino acid/ Amino Acid Derivative | Structure |
|---|---|
| D-ALA D-Alanine | |
| ASP Aspartic acid | 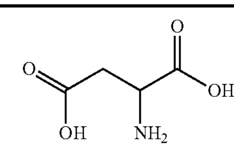 |
| Bicine | 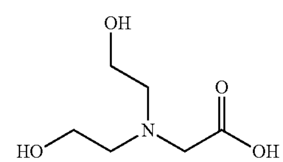 [SMILES: O=C(O)CN(CCO)CCO] |
| D-GLU D-Glutamic acid | 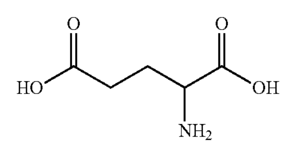 |
| GLY-GLY Glycylglycine | 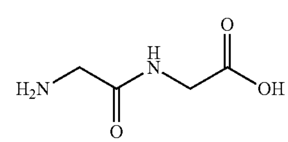 |
| IDAA Iminodiacetic acid | 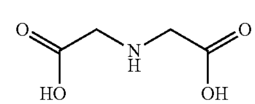 |

According to one embodiment, the stabilized lipid-based glycopeptide antibiotic composition maintains at least 98.0% of its original biological activity for at least 200 days at 4° C. According to another embodiment, the stabilized lipid-based glycopeptide antibiotic composition maintains at least 98.5% of its original biological activity for at least 150 days at 4° C. According to another embodiment, the stabilized lipid-based glycopeptide antibiotic composition maintains at least 99.0% of its original biological activity for at least 100 days at 4° C. According to another embodiment, the stabilized lipid-based glycopeptide antibiotic composition maintains at least 99.5% of its original biological activity for at least 50 days at 4° C. According to another embodiment, the stabilized lipid-based glycopeptide antibiotic composition maintains at least 99.9% of its original biological activity for at least two weeks at 4° C.

According to another embodiment, the stabilized lipid-based glycopeptide antibiotic composition maintains at least 80% of its original biological activity for at least 200 days at room temperature (RT).

According to one embodiment, the stabilized lipid-based glycopeptide antibiotic composition of the present invention produces product degradants crystalline at a rate less than 0.05% by weight per week at 4° C. According to a further embodiment, the stabilized lipid-based glycopeptide antibiotic composition produces product degradants at a rate less than 0.04% by weight per week at 4° C. According to a further embodiment, the stabilized lipid-based glycopeptide antibiotic composition produces product degradants at a rate less than 0.03% by weight per week at 4° C. According to a further embodiment, the stabilized lipid-based glycopeptide antibiotic composition produces product degradants at a rate less than 0.02% by weight per week at 4° C. According to a further embodiment, the stabilized lipid-based glycopeptide antibiotic composition produces product degradants at a rate less than 0.01% by weight per week at 4° C. In one embodiment, the product degradants produced at 4° C. are crystalline degradation products (i.e., CDP-I-m plus CDP-I-M)

According to one embodiment, the stabilized lipid-based glycopeptide antibiotic composition of the present invention produces product degradants at a rate less than about 0.5% by weight per week at room temperature. According to a further embodiment, the stabilized lipid-based glycopeptide antibiotic composition of the present invention produces product degradants at a rate less than about 0.4% by weight per week at room temperature. According to a further embodiment, the stabilized lipid-based glycopeptide antibiotic composition of the present invention produces product degradants at a rate less than about 0.3% by weight per week at room temperature. According to a yet further embodiment, the stabilized lipid-based glycopeptide antibiotic composition of the present invention produces product degradants at a rate less than about 0.2% by weight per week at room temperature. In one embodiment, the product degradants produced at room temperature are crystalline degradation products (i.e., CDP-I-m plus CDP-I-M)

In one embodiment, the stabilized lipid-based glycopeptide antibiotic composition comprising a lipid component, a glycopeptide antibiotic component, and an amino acid or derivative thereof is at least 44% more stable than a lipid-based glycopeptide antibiotic that does not comprise an amino acid or derivative thereof. In a further embodiment, the stabilized lipid-based glycopeptide antibiotic composition comprising a lipid component, a glycopeptide antibiotic component, and an amino acid or derivative thereof is at least 55% more stable than a lipid-based glycopeptide antibiotic that does not comprise an amino acid or derivative thereof. In a further embodiment, the stabilized lipid-based glycopeptide antibiotic composition comprising a lipid component, a glycopeptide antibiotic component, and an amino acid or derivative thereof is at least 66% more stable than a lipid-based glycopeptide antibiotic that does not comprise an amino acid or derivative thereof. In a further embodiment, the stabilized lipid-based glycopeptide antibiotic composition comprising a lipid component, a glycopeptide antibiotic component, and an amino acid or derivative thereof is at least 77% more stable than a lipid-based glycopeptide antibiotic that does not comprise an amino acid or derivative thereof. In a yet further embodiment, the stabilized lipid-based glycopeptide antibiotic composition comprising a lipid component, a glycopeptide antibiotic component, and an amino acid or derivative thereof is at least 88% more stable than a lipid-based glycopeptide antibiotic that does not comprise an amino acid or derivative thereof.

According to another embodiment, the molar ratio of the glycopeptide antibiotic to the amino acid or amino acid derivative ranges from about 1:1 to about 1:4. According to another embodiment, the molar ratio of the glycopeptide antibiotic to the amino acid or amino acid derivative ranges from about 1:1 to about 1:3. According to another embodiment, the molar ratio of the glycopeptide antibiotic to the amino acid or amino acid derivative ranges from about 1:1 to about 1:2. According to another embodiment, the molar ratio of the glycopeptide antibiotic to the amino acid or amino acid derivative is about 1:4. According to another embodiment, the molar ratio of the glycopeptide antibiotic to the amino acid or amino acid derivative is about 1:3. According to another embodiment, the molar ratio of the glycopeptide antibiotic to the amino acid or amino acid derivative is about 1:2. According to another embodiment, the molar ratio of the glycopeptide antibiotic to the amino acid or amino acid derivative is about 1:1.

According to another embodiment, the stabilized lipid-based glycopeptide antibiotic composition has a pH ranging from about 5.0 to about 6.5. According to another embodiment, the stabilized lipid-based glycopeptide antibiotic composition has a pH ranging from about 5.1 to about 6.5. According to another embodiment, the stabilized lipid-based glycopeptide antibiotic composition has a pH ranging from about 5.2 to about 6.5. According to another embodiment, the stabilized lipid-based glycopeptide antibiotic composition has a pH ranging from about 5.3 to about 6.5. According to another embodiment, the stabilized lipid-based glycopeptide antibiotic composition has a pH ranging from about 5.4 to about 6.5. According to another embodiment, the stabilized lipid-based glycopeptide antibiotic composition has a pH ranging from about 5.5 to about 6.5. According to another embodiment, the stabilized lipid-based glycopeptide antibiotic composition has a pH ranging from about 5.6 to about 6.5. According to another embodiment, the stabilized lipid-based glycopeptide antibiotic composition has a pH ranging from about 5.7 to about 6.5. According to another embodiment, the stabilized lipid-based glycopeptide antibiotic composition has a pH ranging from about 5.8 to about 6.5. According to another embodiment, the stabilized lipid-based glycopeptide antibiotic composition has a pH ranging from about 5.9 to about 6.5. According to another embodiment, the stabilized lipid-based glycopeptide antibiotic composition has a pH ranging from about 6.0 to about 6.5. According to another embodiment, the stabilized lipid-based glycopeptide antibiotic composition has a pH ranging from about 6.1 to about 6.5. According to another embodiment, the stabilized lipid-based glycopeptide antibiotic composition has a pH ranging from about 6.2 to about 6.5. According to another embodiment, the stabilized lipid-based glycopeptide antibiotic composition has a pH ranging from about 6.3 to about 6.5. According to another embodiment, the stabilized lipid-based glycopeptide antibiotic composition has a pH ranging from about 6.4 to about 6.5. According to another embodiment, the stabilized lipid-based glycopeptide antibiotic composition has a pH of 5.0. According to another embodiment, the stabilized lipid-based glycopeptide antibiotic composition has a pH of 5.5. According to another embodiment, the stabilized lipid-based glycopeptide antibiotic composition has a pH of 6.0. According to another embodiment, the stabilized lipid-based glycopeptide antibiotic composition has a pH of 6.5.

According to another embodiment, the concentration of the glycopeptide antibiotic in the composition ranges from 20 mg/mL to 200 mg/mL. According to another embodiment, the concentration of the glycopeptide antibiotic in the composition ranges from 30 mg/mL to 200 mg/mL. According to another embodiment, the concentration of the glycopeptide antibiotic in the composition ranges from 40 mg/mL to 200 mg/mL. According to another embodiment, the concentration of the glycopeptide antibiotic in the composition ranges from 50 mg/mL to 200 mg/mL. According to another embodiment, the concentration of the glycopeptide antibiotic in the composition ranges from 60 mg/mL to 200 mg/mL. According to another embodiment, the concentration of the glycopeptide antibiotic in the composition ranges from 70 mg/mL to 200 mg/mL. According to another embodiment, the concentration of the glycopeptide antibiotic in the composition ranges from 80 mg/mL to 200 mg/mL. According to another embodiment, the concentration of the glycopeptide antibiotic in the composition ranges from 90 mg/mL to 200 mg/mL. According to another embodiment, the concentration of the glycopeptide antibiotic in the composition ranges from 100 mg/mL to 200 mg/mL. According to another embodiment, the concentration of the glycopeptide antibiotic in the composition ranges from 110 mg/mL to 200 mg/mL. According to another embodiment, the concentration of the glycopeptide antibiotic in the composition ranges from 120 mg/mL to 200 mg/mL. According to another embodiment, the concentration of the glycopeptide antibiotic in the composition ranges from 130 mg/mL to 200 mg/mL. According to another embodiment, the concentration of the glycopeptide antibiotic in the composition ranges from 140 mg/mL to 200 mg/mL. According to another embodiment, the concentration of the glycopeptide antibiotic in the composition ranges from 150 mg/mL to 200 mg/mL. According to another embodiment, the concentration of the glycopeptide antibiotic in the composition ranges from 160 mg/mL to 200 mg/mL. According to another embodiment, the concentration of the glycopeptide antibiotic in the composition ranges from 170 mg/mL to 200 mg/mL. According to another embodiment, the concentration of the glycopeptide antibiotic in the composition ranges from 180 mg/mL to 200 mg/mL. According to another embodiment, the concentration of the glycopeptide antibiotic in the composition ranges from 190 mg/mL to 200 mg/mL. According to another embodiment, the concentration of the glycopeptide antibiotic in the composition is 200 mg/mL. According to another embodiment, the concentration of the glycopeptide antibiotic in the composition is 100 mg/mL.

According to another embodiment, the stabilized lipid-based glycopeptide antibiotic composition of the present invention comprises an aqueous dispersion of liposomes. The formulation can contain lipid excipients to form the liposomes, and salts/buffers to provide the appropriate osmolarity and pH. The formulation can comprise a pharmaceutical excipient. The pharmaceutical excipient can be a liquid, diluent, solvent or encapsulating material, involved in carrying or transporting any subject composition or component thereof from one organ, or portion of the body, to another organ, or portion of the body. Each excipient must be "acceptable" in the sense of being compatible with the subject composition and its components and not injurious to the patient. Suitable excipients include trehalose, raffinose, mannitol, sucrose, leucine, trileucine, and calcium chloride. Examples of other suitable excipients include (1) sugars, such as lactose, and glucose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Representative lipid-based glycopeptide antibiotic formulations are shown in Table 5.

TABLE 5

Representative formulation components

| Glycopeptide | Lipid Component | Amino Acid |
| --- | --- | --- |
| Vancomycin | DPPC | Bicine |
| Vancomycin | DPPC | GLU |
| Vancomycin | DPPC | GLY-GLY |
| Vancomycin | DPPC | IDAA |
| Vancomycin | DPPC | ASP |
| Vancomycin | DPPC | D-ALA |
| Vancomycin | DPPC + Cholesterol | Bicine |
| Vancomycin | DPPC + Cholesterol | GLU |
| Vancomycin | DPPC + Cholesterol | GLY-GLY |
| Vancomycin | DPPC + Cholesterol | IDAA |
| Vancomycin | DPPC + Cholesterol | ASP |
| Vancomycin | DPPC + Cholesterol | D-ALA |
| Vancomycin | DPPG | Bicine |
| Vancomycin | DPPG | GLU |
| Vancomycin | DPPG | GLY-GLY |
| Vancomycin | DPPG | IDAA |
| Vancomycin | DPPG | ASP |
| Vancomycin | DPPG | D-ALA |
| Vancomycin | DPPG + Cholesterol | Bicine |
| Vancomycin | DPPG + Cholesterol | GLU |
| Vancomycin | DPPG + Cholesterol | GLY-GLY |
| Vancomycin | DPPG + Cholesterol | IDAA |
| Vancomycin | DPPG + Cholesterol | ASP |
| Vancomycin | DPPG + Cholesterol | D-ALA |
| Vancomycin | DPPC + DPPG + Cholesterol | Bicine |
| Vancomycin | DPPC + DPPG + Cholesterol | GLU |
| Vancomycin | DPPC + DPPG + Cholesterol | GLY-GLY |
| Vancomycin | DPPC + DPPG + Cholesterol | IDAA |
| Vancomycin | DPPC + DPPG + Cholesterol | ASP |
| Vancomycin | DPPC + DPPG + Cholesterol | D-ALA |
| Vancomycin | POPC | Bicine |
| Vancomycin | POPC | GLU |
| Vancomycin | POPC | GLY-GLY |
| Vancomycin | POPC | IDAA |
| Vancomycin | POPC | ASP |
| Vancomycin | POPC | D-ALA |

In one embodiment, the present invention provides a stabilized glycopeptides composition comprising a lipid component, a glycopeptides antibiotic and an amino acid or derivative thereof. In one embodiment, the lipid to glycopeptide molar ratio is 10:1 or less, 9:1 or less, 8:1 or less, 7:1 or less, 6:1 or less, 5:1 or less, 4:1 or less, 3:1 or less, 2:1 or less, 1:1 or less, 0.75:1 or less or 0.5:1 or less. In another embodiment, the lipid to glycopeptide molar ratio is about 1:1, about 2:1, about 3:1, about 4:1 or about 5:1.

In one embodiment, the present invention relates to a stabilized lipid-glycopeptide antibiotic composition comprising a lipid component, a glycopeptide antibiotic, and an amino acid or derivative thereof, wherein the weight ratio of the total lipid component to the glycopeptide antibiotic is from about 0.1:1 to about 5:1. In a further embodiment, the weight ratio of the lipid component to the glycopeptide antibiotic is about 3:1 or less. In a further embodiment, the weight ratio of the lipid component to the glycopeptide antibiotic is about 1:1 or less. In another embodiment, the weight ratio of the lipid component to the glycopeptide antibiotic is less than 1:1.

It is understood that for the ranges of values provided above, each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Representative lipid-based glycopeptide antibiotic formulations with exemplary lipid to glycopeptide ratios are shown in Table 6.

TABLE 6

Representative formulations with lipid to drug ratios

| Glycopeptide Antibiotic | Lipid Component | Amino Acid | Lipid: glycopeptide |
|---|---|---|---|
| Vancomycin | DPPC | Bicine | 5:1 |
| Vancomycin | DPPC | GLU | 5:1 |
| Vancomycin | DPPC | GLY-GLY | 5:1 |
| Vancomycin | DPPC | IDAA | 5:1 |
| Vancomycin | DPPC | ASP | 5:1 |
| Vancomycin | DPPC | D-ALA | 5:1 |
| Vancomycin | DPPC + Cholesterol | Bicine | 5:1 |
| Vancomycin | DPPC + Cholesterol | GLU | 5:1 |
| Vancomycin | DPPC + Cholesterol | GLY-GLY | 5:1 |
| Vancomycin | DPPC + Cholesterol | IDAA | 5:1 |
| Vancomycin | DPPC + Cholesterol | ASP | 5:1 |
| Vancomycin | DPPC + Cholesterol | D-ALA | 5:1 |
| Vancomycin | DPPG | Bicine | 5:1 |
| Vancomycin | DPPG | GLU | 5:1 |
| Vancomycin | DPPG | GLY-GLY | 5:1 |
| Vancomycin | DPPG | IDAA | 5:1 |
| Vancomycin | DPPG | ASP | 5:1 |
| Vancomycin | DPPG | D-ALA | 5:1 |
| Vancomycin | DPPG + Cholesterol | Bicine | 5:1 |
| Vancomycin | DPPG + Cholesterol | GLU | 5:1 |
| Vancomycin | DPPG + Cholesterol | GLY-GLY | 5:1 |
| Vancomycin | DPPG + Cholesterol | IDAA | 5:1 |
| Vancomycin | DPPG + Cholesterol | ASP | 5:1 |
| Vancomycin | DPPG + Cholesterol | D-ALA | 5:1 |
| Vancomycin | DPPC + DPPG + Cholesterol | Bicine | 5:1 |
| Vancomycin | DPPC + DPPG + Cholesterol | GLU | 5:1 |
| Vancomycin | DPPC + DPPG + Cholesterol | GLY-GLY | 5:1 |
| Vancomycin | DPPC + DPPG + Cholesterol | IDAA | 5:1 |
| Vancomycin | DPPC + DPPG + Cholesterol | ASP | 5:1 |
| Vancomycin | DPPC + DPPG + Cholesterol | D-ALA | 5:1 |
| Vancomycin | POPC | Bicine | 5:1 |
| Vancomycin | POPC | GLU | 5:1 |
| Vancomycin | POPC | GLY-GLY | 5:1 |
| Vancomycin | POPC | IDAA | 5:1 |
| Vancomycin | POPC | ASP | 5:1 |
| Vancomycin | POPC | D-ALA | 5:1 |
| Vancomycin | DPPC | Bicine | 3:1 |
| Vancomycin | DPPC | GLU | 3:1 |
| Vancomycin | DPPC | GLY-GLY | 3:1 |
| Vancomycin | DPPC | IDAA | 3:1 |
| Vancomycin | DPPC | ASP | 3:1 |
| Vancomycin | DPPC | D-ALA | 3:1 |
| Vancomycin | DPPC + Cholesterol | Bicine | 3:1 |
| Vancomycin | DPPC + Cholesterol | GLU | 3:1 |
| Vancomycin | DPPC + Cholesterol | GLY-GLY | 3:1 |
| Vancomycin | DPPC + Cholesterol | IDAA | 3:1 |
| Vancomycin | DPPC + Cholesterol | ASP | 3:1 |
| Vancomycin | DPPC + Cholesterol | D-ALA | 3:1 |
| Vancomycin | DPPG | Bicine | 3:1 |
| Vancomycin | DPPG | GLU | 3:1 |
| Vancomycin | DPPG | GLY-GLY | 3:1 |
| Vancomycin | DPPG | IDAA | 3:1 |
| Vancomycin | DPPG | ASP | 3:1 |
| Vancomycin | DPPG | D-ALA | 3:1 |
| Vancomycin | DPPG + Cholesterol | Bicine | 3:1 |
| Vancomycin | DPPG + Cholesterol | GLU | 3:1 |
| Vancomycin | DPPG + Cholesterol | GLY-GLY | 3:1 |
| Vancomycin | DPPG + Cholesterol | IDAA | 3:1 |
| Vancomycin | DPPG + Cholesterol | ASP | 3:1 |
| Vancomycin | DPPG + Cholesterol | D-ALA | 3:1 |
| Vancomycin | DPPC + DPPG + Cholesterol | Bicine | 3:1 |
| Vancomycin | DPPC + DPPG + Cholesterol | GLU | 3:1 |
| Vancomycin | DPPC + DPPG + Cholesterol | GLY-GLY | 3:1 |
| Vancomycin | DPPC + DPPG + Cholesterol | IDAA | 3:1 |
| Vancomycin | DPPC + DPPG + Cholesterol | ASP | 3:1 |
| Vancomycin | DPPC + DPPG + Cholesterol | D-ALA | 3:1 |
| Vancomycin | POPC | Bicine | 3:1 |
| Vancomycin | POPC | GLU | 3:1 |
| Vancomycin | POPC | GLY-GLY | 3:1 |
| Vancomycin | POPC | IDAA | 3:1 |
| Vancomycin | POPC | ASP | 3:1 |
| Vancomycin | POPC | D-ALA | 3:1 |
| Vancomycin | DPPC | Bicine | 2:1 |
| Vancomycin | DPPC | GLU | 2:1 |
| Vancomycin | DPPC | GLY-GLY | 2:1 |
| Vancomycin | DPPC | IDAA | 2:1 |
| Vancomycin | DPPC | ASP | 2:1 |
| Vancomycin | DPPC | D-ALA | 2:1 |
| Vancomycin | DPPC + Cholesterol | Bicine | 2:1 |
| Vancomycin | DPPC + Cholesterol | GLU | 2:1 |
| Vancomycin | DPPC + Cholesterol | GLY-GLY | 2:1 |
| Vancomycin | DPPC + Cholesterol | IDAA | 2:1 |
| Vancomycin | DPPC + Cholesterol | ASP | 2:1 |
| Vancomycin | DPPC + Cholesterol | D-ALA | 2:1 |
| Vancomycin | DPPG | Bicine | 2:1 |
| Vancomycin | DPPG | GLU | 2:1 |
| Vancomycin | DPPG | GLY-GLY | 2:1 |
| Vancomycin | DPPG | IDAA | 2:1 |
| Vancomycin | DPPG | ASP | 2:1 |
| Vancomycin | DPPG | D-ALA | 2:1 |
| Vancomycin | DPPG + Cholesterol | Bicine | 2:1 |
| Vancomycin | DPPG + Cholesterol | GLU | 2:1 |
| Vancomycin | DPPG + Cholesterol | GLY-GLY | 2:1 |
| Vancomycin | DPPG + Cholesterol | IDAA | 2:1 |
| Vancomycin | DPPG + Cholesterol | ASP | 2:1 |
| Vancomycin | DPPG + Cholesterol | D-ALA | 2:1 |
| Vancomycin | DPPC + DPPG + Cholesterol | Bicine | 2:1 |
| Vancomycin | DPPC + DPPG + Cholesterol | GLU | 2:1 |
| Vancomycin | DPPC + DPPG + Cholesterol | GLY-GLY | 2:1 |
| Vancomycin | DPPC + DPPG + Cholesterol | IDAA | 2:1 |
| Vancomycin | DPPC + DPPG + Cholesterol | ASP | 2:1 |
| Vancomycin | DPPC + DPPG + Cholesterol | D-ALA | 2:1 |

TABLE 6-continued

Representative formulations with lipid to drug ratios

| Glycopeptide Antibiotic | Lipid Component | Amino Acid | Lipid: glycopeptide |
|---|---|---|---|
| Vancomycin | POPC | Bicine | 2:1 |
| Vancomycin | POPC | GLU | 2:1 |
| Vancomycin | POPC | GLY-GLY | 2:1 |
| Vancomycin | POPC | IDAA | 2:1 |
| Vancomycin | POPC | ASP | 2:1 |
| Vancomycin | POPC | D-ALA | 2:1 |
| Vancomycin | DPPC | Bicine | 1:1 |
| Vancomycin | DPPC | GLU | 1:1 |
| Vancomycin | DPPC | GLY-GLY | 1:1 |
| Vancomycin | DPPC | IDAA | 1:1 |
| Vancomycin | DPPC | ASP | 1:1 |
| Vancomycin | DPPC | D-ALA | 1:1 |
| Vancomycin | DPPC + Cholesterol | Bicine | 1:1 |
| Vancomycin | DPPC + Cholesterol | GLU | 1:1 |
| Vancomycin | DPPC + Cholesterol | GLY-GLY | 1:1 |
| Vancomycin | DPPC + Cholesterol | IDAA | 1:1 |
| Vancomycin | DPPC + Cholesterol | ASP | 1:1 |
| Vancomycin | DPPC + Cholesterol | D-ALA | 1:1 |
| Vancomycin | DPPG | Bicine | 1:1 |
| Vancomycin | DPPG | GLU | 1:1 |
| Vancomycin | DPPG | GLY-GLY | 1:1 |
| Vancomycin | DPPG | IDAA | 1:1 |
| Vancomycin | DPPG | ASP | 1:1 |
| Vancomycin | DPPG | D-ALA | 1:1 |
| Vancomycin | DPPG + Cholesterol | Bicine | 1:1 |
| Vancomycin | DPPG + Cholesterol | GLU | 1:1 |
| Vancomycin | DPPG + Cholesterol | GLY-GLY | 1:1 |
| Vancomycin | DPPG + Cholesterol | IDAA | 1:1 |
| Vancomycin | DPPG + Cholesterol | ASP | 1:1 |
| Vancomycin | DPPG + Cholesterol | D-ALA | 1:1 |
| Vancomycin | DPPC + DPPG + Cholesterol | Bicine | 1:1 |
| Vancomycin | DPPC + DPPG + Cholesterol | GLU | 1:1 |
| Vancomycin | DPPC + DPPG + Cholesterol | GLY-GLY | 1:1 |
| Vancomycin | DPPC + DPPG + Cholesterol | IDAA | 1:1 |
| Vancomycin | DPPC + DPPG + Cholesterol | ASP | 1:1 |
| Vancomycin | DPPC + DPPG + Cholesterol | D-ALA | 1:1 |
| Vancomycin | POPC | Bicine | 1:1 |
| Vancomycin | POPC | GLU | 1:1 |
| Vancomycin | POPC | GLY-GLY | 1:1 |
| Vancomycin | POPC | IDAA | 1:1 |
| Vancomycin | POPC | ASP | 1:1 |
| Vancomycin | POPC | D-ALA | 1:1 |

According to another aspect, the described invention provides a method for preparing a stabilized lipid-based glycopeptide antibiotic composition, wherein the method comprises:

infusing, in an in-line fashion, a first stream of a lipid solution containing a lipid component in a solvent with a second stream of an aqueous solution comprising a glycopeptide antibiotic and an amino acid or a derivative thereof, wherein the amino acid or the derivative thereof binds to the glycopeptide antibiotic and forms a stabilized glycopeptide antibiotic-amino acid complex, and the stabilized glycopeptide antibiotic-amino acid complex is entrapped by or complexed with the a lipid component (i.e., one lipid or a mixture of multiple lipids).

According to some embodiments, the first stream in step (a) contains a lipid dissolved in a solvent. According to some such embodiments, the solvent is ethanol.

According to another embodiment, the lipid solution comprises from about 2 mg/mL to 200 mg/mL of lipids. According to another embodiment, the lipid solution comprises about 20 mg/mL of lipids.

Examples of the lipid component that can be used in preparing the stabilized lipid-based glycopeptide antibiotic composition of the present invention includes, but is not limited to, phosphatidylcholine (PC), phosphatidylglycerol (PG), phosphatidylinositol (PI), phosphatidylserine (PS), phosphatidylethanolamine (PE), phosphatidic acid (PA), egg phosphatidylcholine (EPC), egg phosphatidylglycerol (EPG), egg phosphatidylinositol (EPI), egg phosphatidylserine (EPS), phosphatidylethanolamine (EPE), phosphatidic acid (EPA), soy phosphatidylcholine (SPC), soy phosphatidylglycerol (SPG), soy phosphatidylserine (SPS), soy phosphatidylinositol (SPI), soy phosphatidylethanolamine (SPE), soy phosphatidic acid (SPA), hydrogenated egg phosphatidylcholine (HEPC), hydrogenated egg phosphatidylglycerol (HEPG), hydrogenated egg phosphatidylinositol (HEPI), hydrogenated egg phosphatidylserine (HEPS), hydrogenated phosphatidylethanolamine (HEPE), hydrogenated phosphatidic acid (HEPA), hydrogenated soy phosphatidylcholine (HSPC), hydrogenated soy phosphatidylglycerol (HSPG), hydrogenated soy phosphatidylserine (HSPS), hydrogenated soy phosphatidylinositol (HSPI), hydrogenated soy phosphatidylethanolamine (HSPE), hydrogenated soy phosphatidic acid (HSPA), dipalmitoylphosphatidylcholine (DPPC), dimyristoylphosphatidylcholine (DMPC), dimyristoylphosphatidylglycerol (DMPG), dipalmitoylphosphatidylglycerol (DPPG), distearoylphosphatidylcholine (DSPC), distearoylphosphatidylglycerol (DSPG), dioleoylphosphatidylcholine (DOPC), dioleylphosphatidylethanolamine (DOPE), palmitoylstearoylphosphatidyl-choline (PSPC), palmitoylstearolphosphatidylglycerol (PSPG), mono-oleoyl-phosphatidylethanolamine (MOPE), tocopherol, tocopherol hemisuccinate, cholesterol sulfate, cholesteryl hemisuccinate, cholesterol derivatives, ammonium salts of fatty acids, ammonium salts of phospholipids, ammonium salts of glycerides, myristylamine, palmitylamine, laurylamine, stearylamine, dilauroyl ethylphosphocholine (DLEP), dimyristoyl ethylphosphocholine (DMEP), dipalmitoyl ethylphosphocholine (DPEP) and distearoyl ethylphosphocholine (DSEP), N-(2,3-di-(9-(Z)-octadecenyloxy)-prop-1-yl-N,N,N-trimethylammonium chloride (DOTMA), 1,2-bis(oleoyloxy)-3-(trimethylammonio) propane (DOTAP), distearoylphosphatidylglycerol (DSPG), dimyristoylphosphatidylacid (DMPA), dipalmitoylphosphatidylacid (DPPA), distearoylphosphatidylacid (DSPA), dimyristoylphosphatidylinositol (DMPI), dipalmitoylphosphatidylinositol (DPPI), distearoylphosphatidylinositol (DSPI), dimyristoylphosphatidylserine (DMPS), dipalmitoylphosphatidylserine (DPPS), distearoylphosphatidylserine (DSPS), or a mixture thereof.

According to another embodiment, the lipid component that can be used in preparing a stabilized lipid-based glycopeptide antibiotic composition of the present invention includes mixed phospholipids, e.g., palmitoylstearoylphosphatidylcholine (PSPC) and palmitoylstearoylphosphatidylglycerol (PSPG)), triacylglycerol, diacylglycerol, seranide, sphingosine, sphingomyelin, and single acylated phospholipids, such as mono-oleoyl-phosphatidylethanol amine (MOPE).

According to another embodiment, the lipid component that can be used in preparing the stabilized lipid-based glycopeptide antibiotic composition of the present invention includes ammonium salts of fatty acids, phospholipids and glycerides, sterols, phosphatidylglycerols (PGs), phosphatidic acids (PAs), phosphotidylcholines (PCs), phosphatidylinositols (PIs) and the phosphatidylserines (PSs). The fatty acids include fatty acids of carbon chain lengths of 12 to 26 carbon atoms that are either saturated or unsaturated.

Some specific examples include, but are not limited to, myristylamine, palmitylamine, laurylamine and stearylamine, dilauroyl ethylphosphocholine (DLEP), dimyristoyl ethylphosphocholine (DMEP), dipalmitoyl ethylphosphocholine (DPEP) and distearoyl ethylphosphocholine (DSEP), N-(2,3-di-(9 (Z)-octadecenyloxy)-prop-1-yl-N,N,N-trimethylammonium chloride (DOTMA) and 1,2-bis(oleoyloxy)-3-(trimethylammonio)propane (DOTAP).

According to another embodiment, the lipid component consists essentially of a phosphatidylcholine. According to another embodiment, the lipid component consists essentially of dipalmitoylphosphatidylcholine (DPPC). According to another embodiment, the lipid component consists essentially of palmitoyloleoylphosphatidylcholine (POPC).

According to another embodiment, the lipid component consists essentially of phosphatidylglycerol. According to another embodiment, the lipid component consists essentially of 1-palmitoyl-2-oleoyl-sn-glycero-3-phosphoglycerol (POPG).

According to another embodiment, the lipid component includes a sterol, including, but not limited to, cholesterol and ergosterol. In one embodiment, the lipid component consists of a sterol and one additional lipid. In a further embodiment, the sterol is cholesterol.

According to another embodiment, the first flow rate is between 0.1 L/min and 100 L/min. According to another embodiment, the first flow rate is between 0.5 L/min and 10 L/min. According to another embodiment, the first flow rate is between 0.5 L/min and 1.5 L/min. According to another embodiment, the first flow rate is about 10 L/min. According to another embodiment, the first flow rate is about 1 L/min.

According to another embodiment, the molar ratio of the glycopeptide antibiotic to the amino acid or amino acid derivative ranges from about 1:1 to about 1:4. According to another embodiment, the molar ratio of the glycopeptide antibiotic to the amino acid or amino acid derivative ranges from about 1:1 to about 1:3. According to another embodiment, the molar ratio of the glycopeptide antibiotic to the amino acid or amino acid derivative ranges from about 1:1 to about 1:2. According to another embodiment, the molar ratio of the glycopeptide antibiotic to the amino acid or amino acid derivative is about 1:4. According to another embodiment, the molar ratio of the glycopeptide antibiotic to the amino acid or amino acid derivative is about 1:3. According to another embodiment, the molar ratio of the glycopeptide antibiotic to the amino acid or amino acid derivative is about 1:2. According to another embodiment, the molar ratio of the glycopeptide antibiotic to the amino acid or amino acid derivative is about 1:1.

According to another embodiment, the aqueous solution comprises between about 20 mg/mL and about 500 mg/mL of the glycopeptide antibiotic. According to another embodiment, the first stream comprises between about 50 mg/mL and about 250 mg/mL of the glycopeptide antibiotic. According to another embodiment, the first stream comprises between about 100 mg/mL and about 200 mg/mL of the glycopeptide antibiotic. According to another embodiment, the first stream comprises about 100 mg/mL of the glycopeptide antibiotic. According to another embodiment, the first stream comprises about 200 mg/mL of the glycopeptide antibiotic.

According to another embodiment, the aqueous solution has pH of from 5.0 to 6.5. According to another embodiment, the aqueous solution has pH of from 5.1 to 6.5. According to another embodiment, the aqueous solution has pH of from 5.2 to 6.5. According to another embodiment, the aqueous solution has pH of from 5.3 to 6.5. According to another embodiment, the aqueous solution has pH of from 5.4 to 6.5. According to another embodiment, the aqueous solution has a pH ranging from 5.5 to 6.5. According to another embodiment, the aqueous solution has pH of from 5.6 to 6.5. According to another embodiment, the aqueous solution has pH of from 5.7 to 6.5. According to another embodiment, the aqueous solution has pH of from 5.8 to 6.5. According to another embodiment, the aqueous solution has pH of from 5.9 to 6.5. According to another embodiment, the aqueous solution has pH of from 6.0 to 6.5. According to another embodiment, the aqueous solution has pH of from 6.1 to 6.5. According to another embodiment, the aqueous solution has pH of from 6.2 to 6.5. According to another embodiment, the aqueous solution has pH of from 6.3 to 6.5. According to another embodiment, the aqueous solution has pH of from 6.4 to 6.5. According to another embodiment, the aqueous solution has a pH of 5.0. According to another embodiment, the aqueous solution has a pH of 5.5. According to another embodiment, the aqueous solution has a pH of 6.0. According to another embodiment, the aqueous solution has a pH of 6.5.

According to one embodiment, the second flow rate is between 0.1 L/min and 100 L/min. According to another embodiment, the second flow rate is between 0.5 L/min and 10 L/min. According to another embodiment, the second flow rate is between 0.5 L/min and 2 L/min. According to another embodiment, the second flow rate is between 1 L/min and 2 L/min. According to another embodiment, the second flow rate is about 1.5 L/min. According to another embodiment, the second flow rate is about 10 L/min.

According to one embodiment, the ratio of the second flow rate to the first flow rate is from about 0.1:1.0 to about 1:0.1.0. According to another embodiment, the ratio of the second flow rate to the first flow rate is from about 0.5:1.0 to about 2.0:1.0. According to another embodiment, the ratio of the second flow rate to the first flow rate is from about 1.0:1.0 to about 2.0:1.0. According to one embodiment, the ratio of the second flow rate to the first flow rate is about 1.5:1.0.

According to another embodiment, the saline solution comprises from about 0.9% wt/wt to about 1.5% wt/wt of sodium chloride (NaCl). According to another embodiment, the saline solution comprises less than 0.9% wt/wt of sodium chloride (NaCl). According to another embodiment, the saline solution comprises about 0.9% wt/wt of sodium chloride (NaCl). According to another embodiment, the saline solution comprises from about 1.0% wt/wt to about 1.5% wt/wt of sodium chloride (NaCl). According to another embodiment, the saline solution comprises from 1.1% wt/wt to 1.5% wt/wt of sodium chloride (NaCl). According to another embodiment, the saline solution comprises from about 1.2% wt/wt to about 1.5% wt/wt of sodium chloride (NaCl). According to another embodiment, the saline solution comprises from about 1.3% wt/wt to about 1.5% wt/wt of sodium chloride (NaCl). According to another embodiment, the saline solution comprises from about 1.4% wt/wt to about 1.5% wt/wt of sodium chloride (NaCl). According to another embodiment, the saline solution comprises about 1.5% wt/wt of sodium chloride (NaCl). According to another embodiment, the saline solution comprises at least 1.5% wt/wt of sodium chloride (NaCl).

According to one embodiment, the saline solution flow rate is between 0.1 L/min and 10 L/min. According to another embodiment, the saline solution flow rate is between 0.5 L/min and 2 L/min. According to another embodiment, the saline solution flow rate is about 1.5 L/min. According to another embodiment, the saline solution flow rate is about 10 L/min.

According to another embodiment, the method produces an infused mixture, wherein the infused mixture comprises a first population of glycopeptide antibiotics entrapped with the lipid and a second population of glycopeptide antibiotics unentrapped with the lipid.

According to another embodiment, the method of preparation further comprises washing the infused mixture comprising lipid-associated or lipid-unassociated glycopeptide antibiotics by infusing a washing feed at a fourth flow rate, wherein the washing feed comprises a saline solution.

According to another embodiment, the washing step is carried out following the formation of infused mixture, wherein the infused mixture comprises a first population of glycopeptide antibiotics entrapped with the lipid and a second population of glycopeptide antibiotics unentrapped with the lipid.

According to another embodiment, the saline solution comprises from about 0.9% wt/wt to about 1.5% wt/wt of sodium chloride (NaCl). According to another embodiment, the saline solution comprises 0.9% wt/wt of sodium chloride (NaCl). According to another embodiment, the saline solution comprises from about 1.0% wt/wt to about 1.5% wt/wt of sodium chloride (NaCl). According to another embodiment, the saline solution comprises from 1.1% wt/wt to 1.5% wt/wt of sodium chloride (NaCl). According to another embodiment, the saline solution comprises from about 1.2% wt/wt to about 1.5% wt/wt of sodium chloride (NaCl). According to another embodiment, the saline solution comprises from about 1.3% wt/wt to about 1.5% wt/wt of sodium chloride (NaCl). According to another embodiment, the saline solution comprises from 1.4% wt/wt to about 1.5% wt/wt of sodium chloride (NaCl). According to another embodiment, the saline solution comprises 1.5% wt/wt of sodium chloride (NaCl).

According to another embodiment, the method further comprises a step for concentrating lipid-associated glycopeptide antibiotics in the formulation.

According to another aspect, the described invention provides a method for treating a bacterial pulmonary infection, the method comprising administering to a subject in need thereof a therapeutically effective amount of a stabilized lipid-based glycopeptide antibiotic composition, wherein the composition comprises:

(a) a lipid component, (b) a glycopeptide antibiotic component, and (c) an amino acid or a derivative thereof, wherein the amino acid or derivative thereof binds to the glycopeptide antibiotic and forms a stabilized glycopeptide antibiotic-amino acid complex, and wherein the stabilized glycopeptide antibiotic-amino acid complex is entrapped by the lipid.

According to another embodiment, the stabilized lipid-based glycopeptide antibiotic composition can treat infections caused by Gram-positive bacteria, including, but not limited to, genera *Staphylococcus*, *Streptococcus*, *Enterococcus*, *Bacillus*, *Corynebacterium*, *Nocardia*, *Clostridium*, and *Listeria*.

Staphylococci are Gram-positive spherical bacteria that occur in microscopic clusters resembling grapes. While there are 20 species of *Staphylococcus*, only *Staphylococcus aureus* and *Staphylococcus epidermis* are known to be significant in their interactions with humans. *S. aureus* colonizes mainly the nasal passages, but it may be found regularly in most anatomical locales, including skin oral cavity, and gastrointestinal tract. *S. epidermis* is an inhabitant of the skin. Examples of Staphylocci treatable with the lipid-based glycopeptide antibiotic composition of the present invention, include, but are not limited to, *S. aureus*, *S. auricularis*, *S. carnosus*, *S. epidermidis*, *S. haemolvticus*, *S. hyicus*, *S. intermedius*, *S. lugdunensis*, *S. saprophyticus*, *S. sciuri*, *S. simulans*, and *S. warneri*.

Streptococci are Gram-positive, non-motile cocci that divide in one plane, producing chains of cells. The Streptococci are a very heterogeneous group of bacteria. The primary pathogens include *S. pyrogenes* and *S. pneumoniae* but other species can be opportunistic. *S. pyrogenes* is the leading cause of bacterial pharyngitis and tonsillitis. It can also produce sinusitis, otitis, arthritis, and bone infections. Some strains prefer skin, producing either superficial (impetigo) or deep (cellulitis) infections. *S. pneumoniae* is the major cause of bacterial pneumonia in adults. Its virulence is dictated by its capsule. Toxins produced by streptococci include: streptolysins (S & O), NADase, hyaluronidase, streptokinase, DNAses, erythrogenic toxin (which causes scarlet fever rash by producing damage to blood vessels; requires that bacterial cells are lysogenized by phage that encodes toxin). Examples of Streptococci treatable with the lipid-based glycopeptide antibiotic composition of the present invention include, but are not limited to, *S. agalactiae*, *S. anginosus*, *S. bovis*, *S. canis*, *S. constellatus*, *S. dysgalactiae*, *S. equi*, *S. equinus*, *S. iniae*, *S. intermedius*, *S. mitis*, *S. mutans*, *S. oralis*, *S. parasanguinis*, *S. peroris*, *S. pneumoniae*, *S. pyogenes*, *S. ratti*, *S. salivarius*, *S. salivarius* ssp. *thermophilus*, *S. sanguinis*, *S. sobrinus*, *S. suis*, *S. uberis*, *S. vestibularis*, *S. viridans*, and *S. zooepidemicus*.

The genus *Enterococci* consists of Gram-positive, facultatively anaerobic organisms that are ovoid in shape and appear on smear in short chains, in pairs, or as single cells. *Enterococci* are important human pathogens that are increasingly resistant to antimicrobial agents. These organisms were considered previously part of the genus *Streptococcus* but have recently been reclassified into their own genus, called *Enterococcus*. To date, 12 species pathogenic for humans have been described, including the most common human isolates, *Enterococcus faecalis* and *Enterococcus faecium*. *Enterococci* cause between 5 and 15% of cases of endocarditis, which is treated best by the combination of a cell wall-active agent (such as penicillin or vancomycin) and an aminoglycoside to which the organism is not highly resistant; this characteristically results in a synergistic bactericidal effect. Examples of *Enterococci* treatable with the lipid-based glycopeptide antibiotic composition of the present invention include, but are not limited to, *E. avium*, *E. durans*, *E. faecalis*, *E. faecium*, *E. gallinarum*, and *E. solitarius*.

Bacteria of the genus *Bacillus* are acrobic, endospore-forming, gram-positive rods. The genus is one of the most diverse and commercially useful groups of microorganisms. Representatives of this genus are distributed widely in soil, air, and water where they are involved in a range of chemical transformations. Some *Bacillus* species are known to cause health problems in humans. For example, Anthrax is caused by *Bacillus anthracis*. Humans acquire the disease directly from contact with infected herbivores or indirectly via their products. The clinical forms include (1) cutaneous anthrax, from handling infected material; (2) intestinal anthrax, from eating infected meat; and (3) pulmonary anthrax from inhaling spore-laden dust. Several other *Bacillus* spp., in particular *B. cereus* and to a lesser extent *B. subtilis* and *B. licheniformis*, are associated periodically with bacteremia/septicemia, endocarditis, meningitis, and infections of wounds, the ears, eyes, respiratory tract, urinary tract, and gastrointestinal tract. *Bacillus cereus* causes two distinct food poisoning syndromes: a rapid-onset emetic syndrome characterized by nausea and vomiting, and a slower-onset diarrheal syndrome. Examples of pathogenic *Bacillus* species whose infection is treatable with the lipid-based glycopeptide antibiotic composition of the present invention, include, but are not limited to, *B. anthracis*, *B. cereus*, and *B. coagulans*.

Corynebacteria are small, generally non-motile, Gram-positive, non sporulating, pleomorphic bacilli. They are chemoorganotrophic, aerobic, or facultatively anaerobic, and they exhibit a fermentative metabolism under certain conditions. *Corybacterium diphtheriae* is the etiological agent of diphtheria, an upper respiratory disease mainly affecting children. The virulence factors (i.e., diphtheria toxin) have been studied extensively. Examples of Corynebacterial species treatable with the lipid-based glycopeptide antibiotic composition of the present invention include, for example, but are not limited to, *Corynebacterium diphtheria*, *Corynebacterium pseudotuberculosis*, *Corynebacterium tenuis*, *Corynebacterium striatum*, and *Corynebacterium minutissimum*.

The bacteria of the genus *Nocardia* are Gram-positive, partially acid-fast rods, which grow slowly in branching chains resembling fungal hyphae. Three species cause nearly all human infections: *N. asteroides*, *N. brasiliensis*, and *N. caviae*. Infection is by inhalation of airborne bacilli from an environmental source (soil or organic material); the disease is not contagious. Skin lesions caused by *N. brasiliensis* often result from direct inoculation. *Nocardia* subverts antimicrobial mechanisms of phagocytes, causing abscess or rarely granuloma formation with hematogenous or lymphatic dissemination to the skin or central nervous system. Examples of Nocardial species treatable with the lipid-based glycopeptide antibiotic composition of the present invention, include, for example, but are not limited to, *N. aerocolonigenes*, *N. africana*, *N. argentinensis*, *N. asteroides*, *N. blackwelli*, *N. brasiliensis*, *N. brevicatena*, *N. carnea*, *N. caviae*, *N. cerradoensis*, *N. corallina*, *N. cyriacigeorgica*, *N. dassonvillei*, *N. elegans*, *N. farcinica*, *N. nigiitansis*, *N. nova*, *N. opaca*, *N. otitidis-cavarium*, *N. paucivorans*, *N. pseudobrasiliensis*, *N. rubra*, *N. transvelencesis*, *N. uniformis*, *N. vaccinii*, and *N. veterana*.

Clostridia are spore-forming. Gram-positive, anaerobes. Clostridia are rod-shaped, but when producing spores they appear more like drumsticks with a bulge at one end. There are three species of clostridia that cause widely recognized and often-deadly diseases. *C. tetani* is the etiological agent of tetanus, *C. botulinum* is the etiological agent of botulism, and *C. perfringens* is one of the etiological agents of gas gangrene. Tetanus is contracted through contact between spores of *C. tetani* and an open wound, such as stepping on a rusty nail. If an anaerobic environment is present, the spores will germinate. Tetanus is a neurological disease in which *C. tetani* releases an exotoxin called tetanus toxin, which blocks the release of neurotransmitters from the presynaptic membrane of inhibitory interneurons of spinal cord and brainstem of mammals that regulate muscle contraction. Examples of *Clostridium* species treatable with the lipid-based glycopeptide antibiotic composition of the present invention, include, for example, but are not limited to, *C. botulinum*, *C. tetani*, *C. difficile*. *C. perfringens*, and *C. sordellii*.

*Listeria* are non spore-forming, nonbranching Gram-positive rods that occur individually or form short chains. *Listeria* are intracellular pathogens that use host-produced actin filaments for motility within the host cell. *L. monocytogenes* is the causative agent of listeriosis. *L. monocytogenes* is a food-borne pathogen, which can survive normal refrigeration processes. It can cause severe disease in immunocompromised individuals, and pregnant women. Examples of *Listeria* species treatable with the lipid-based glycopeptide antibiotic composition of the present invention, include, for example, but are not limited to, *L. grayi*, *L. innocua*, *L. ivanovii*, *L. monocytogenes*, *L. seeligeri*, *L. murrayi*, and *L. welshimeri*.

Other Examples of Gram-positive bacterial species, whose infection is treatable with the lipid-based glycopeptide antibiotic composition of the present invention, include, but are not limited to, Methicillin-resistant *Staphylococcus aureus* (MRSA), *Escherichia coli*, *Klebsiella*, *Enterobacter*, *Serratia*, *Haemophilus*, *Yersinia pesos*, *Burkholderia pseudomallei*, *Burkholderia cepacia*, *Burkholderia gladioli*, *Burkholderia multivorans*, *Burkholderia vietnamiensis*, *Mycobacterium tuberculosis*, *Mycobacterium avium* complex (MAC) (*Mycobacterium avium* and *Mycobacterium intracellulare*), *Mycobacterium kansasii*, *Mycobacterium xenopi*, *Mycobacterium marinum*, *Mycobacterium mucogenicum*, *Mycobacgerium gordonae*, *Mycobacterium ulcerans*, and *Mycobacterium fortuitum* complex (including, but not limited to, *Mycrobacterium fortuitum*, *Mycrobacterium peregrinum*, *Mycrobacterium chelonae*, *Mycrobacterium abscessus*, and *Mycrobacterium mucogenicum*.

Methicillin-resistant *Staphyloccus aureus* (MRSA) is a type of *staphylococcus* bacteria that is resistant to certain antibiotics called beta-lactams. These antibiotics include methicillin and other more common antibiotics such as oxacillin, penicillin, and amoxicillin.

*Mycobacteria* are non-motile, pleomorphic rods, related to the *Actinomyces*. They are relatively impermeable to various basic dyes but once stained, they retain the dyes with tenacity. They resist decolorization with acidified organic solvents and are therefore called acid-fast. They may appear to be Gram positive, but they take up the stain weakly and irregularly and without requiring iodine treatment to retain it.

On the basis of growth rate, catalase and niacin production, and pigmentation in light or dark, *mycobacteria* are classified into members of the *Mycobacterium tuberculosis* complex (including, but not limited to, *M. tuberculosis. M. bovis*, *Mycobacterium bovis* BCG, *Mycobacterium africanum*, *Mycobacterium microti*, *Mycobacterium canettii*, *Mycobacterium caprae*, and *Mycobacterium pinnipedii*) and nontuberculous species. Most *Mycobacteria* are found in habitats such as water or soil. However, a few are intracellular pathogens of animals and humans. *Mycobacterium tuberculosis*, along with *M. bovis*, *M. africanum*, and *M. microti*, all cause the disease known as tuberculosis (TB). Each member of the TB complex is pathogenic, but *M. tuberculosis* is pathogenic for humans while *M. bovis* is usually pathogenic for animals. Tuberculous *mycobacteria* enter the alveoli by airborne transmission. They resist destruction by alveolar macrophages and multiply, forming the primary lesion or tubercle; they then spread to regional lymph nodes, enter circulation, and reseed the lungs. Tissue destruction results from cell-mediated hypersensitivity.

*Mycobacterium abscessus* is part of the *Mycobacterium fortuitum* complex, a group of rapidly-growing *Mycobacteria* that are ubiquitous in the environment (soil and water). *Mycobacterium fortuitum* complex, for example, includes: *Mycobacterium fortuitum*, *Mycobacterium peregrinum*, *Mycobacterium chelonae*, *Mycobacterium abscessus*, and *Mycobacterium mucogenicum*. *Mycobacterium fortuitum* complex isolates are responsible for almost all human infections caused by rapidly-growing *Mycobacteria*. Infections range from localized wound infections to respiratory disease to serious disseminated infections. *Mycobacterium abscessus* usually causes respiratory and soft tissue/skin infections.

*Mycobacterium avium* complex (MAC) is a commonly isolated group of *Mycobacteria* and is widely distributed in nature (water, soils, birds and other animals and dust). The *M. avium* complex includes *M. avium* and *M. intracellulare*. Infections in immunocompetent patients are usually pulmonary; infections in immunosuppressed patients (e.g., patients who contracted AIDS or patients whose CD4+ cell counts are less than 200) are usually disseminated. MAC isolates are often drug resistant and difficult to treat; treatment is only recommended for the immunosuppressed and in cases of repeated isolation where clinical symptoms exist.

*Mycobacterium chelonae* is part of the *Mycobacterium fortuitum* complex, a group of rapidly-growing *Mycobacteria* that are ubiquitous in the environment (soil and water). *Mycobacterium chelonae* usually causes soft tissue and skin infections. It is necessary to differentiate the *Mycobacterium fortuitum* group (*Mycobacterium fortuitum* and *Mycobacterium peregrinum*) from *Mycobacterium chelonae* and *Mycobacterium abscessus* as the latter two species of the complex are very resistant to anti-mycobacterial drug therapies.

*Mycobacterium fortuitum* and *Mycobacterium peregrinum* are part of the *Mycobacterium fortuitum* complex. *Mycobacterium fortuitum* complex includes: *Mycobacterium fortuitum*, *Mycobacterium peregrinum*, *Mycobacterium chelonae*, *Mycobacterium abscessus*, and *Mycobacterium mucogenicum*. *Mycobacterium fortuitum* complex isolates are responsible for almost all human infections caused by rapidly-growing *Mycobacteria*. The spectrum of diseases caused by these organisms includes soft-tissue abscesses, sternal wound infections after cardiac surgery, prosthetic valve endocarditis, disseminated and localized infection in haemodialysis and peritoneal dialysis patients, pulmonary disease, traumatic wound infection, and disseminated disease often with cutaneous lesions.

*Mycobacterium kansasii* is a significant cause of chronic pulmonary disease in humans, which resembles the disease caused by *Mycobacterium tuberculosis*. In contrast to *Mycobacterium tuberculosis* infection, however, there is minimal risk of human to human transmission. Risk factors often predispose infection (underlying pulmonary disease, cancer, alcoholism, and the like). *Mycobacterium kansasii* is commonly isolated from water samples; infection is thought to be via aerosol route. *Mycobacterium kansasii* is the second most common cause of mycobacterial infection in AIDS patients (after *Mycobacterium avium* complex).

*Mycobacterium marinum* is a fish pathogen found in environmental waters. It grows best below 33° C. and causes a tuberculosis-like disease in fish and a chronic skin lesion known as "swimming pool granuloma" in humans. Infection is acquired by injury of a limb around a home aquarium or marine environment and can lead to a series of ascending subcutaneous abscesses. *M. marinum* resembles *M. kansasii* in being photochromogenic. *M. marinum* varies in susceptibility to antimicrobial agents.

Previously termed "*Mycobacterium chelonae*-like organisms (MCLO)" *Mycobacterium mucogenicum* is part of the *Mycobacterium fortuitum* complex. *Mycobacterium mucogenicum* is the rare cause of human disease; it is estimated that most respiratory isolates are non-pathogenic (except in immunocompromised patients) while most non-respiratory isolates are pathogenic (usually wound infections). *Mycobacterium mucogenicum* isolates have a mucoid appearance on laboratory media.

*Mycobacterium scrofulaceum* is a common cause of lymphadenitis in children aged 1 to 3 years. Lymphadenitis usually involves a single node or a cluster of nodes in the submandibular area. Characteristically, the nodes enlarge slowly over a period of weeks. There are very few local or systemic symptoms. Untreated, the infection will usually point to the surface, rupture, form a draining sinus and eventually calcify. Infection in other tissues occurs occasionally. A very few cases resembling progressive primary tuberculosis have been encountered in children. In children, metastatic bone disease may be prominent. Colonies are usually yellow-orange even when grown in the dark (scotochromogenic). They are usually resistant to antituberculosis drugs in vitro.

*Mycobacterium ulcerans*, found mainly in Africa and Australia, grow only below 33° C. It causes chronic deep cutaneous ulcers in man and usually produces lesions in the cooler parts of the body. *Mycobacterium ulcerans* has a unique drug sensitivity pattern, i.e., resistance to INH and ethambutol and susceptibility to streptomycin and rifampin. Human disease responds poorly to drug treatment and extensive excision followed by skin grafting is often necessary.

Studies have suggested that the source of human *Mycobacterium xenopi* infection is aerosolized water, similar to *Mycobacterium avium* complex. *Mycobacterium xenopi* is not as ubiquitous in all water supplies as *Mycobacterium avium*, preferring to grow in hot water supplies. For immunocompetent patients, pulmonary disease is most common; risk factors include underlying lung disease, heavy smoking, alcohol abuse and exposure to water containing these *Mycobacteria*. AIDS is another risk factor for *Mycobacterium xenopi* infection, often leading to disseminated infection in these patients.

The subject or patient in need of treatment, in one embodiment, has a pulmonary disease. In one embodiment, the pulmonary disease is cystic fibrosis, bronchiectasis, pneumonia, or chronic obstructive pulmonary disease (COPD).

In another embodiment, the subject or patient in need of treatment has osteomyelitis. In another embodiment, the subject or patient in need of treatment has endocarditis, bronchitis, hepatitis, myocarditis, and/or nephritis. In another embodiment, the subject or patient in need of treatment has bacteremia. In another embodiment, the subject or patient in need of treatment has a skin or connective tissue infection, including, but not limited to, folliculitis, cellulitis, furuncules, or pymyositis. In another embodiment, the subject or patient in need of treatment has a wound or surgical site infection.

The therapeutic agents in the compositions of the present invention are delivered in therapeutically effective amounts. Combined with the teachings provided herein, by choosing among the various active compounds and weighing factors such as potency, relative bioavailability, patient body weight, severity of adverse side-effects and mode of administration, an effective prophylactic or therapeutic treatment regimen may be planned which does not cause substantial toxicity and yet is effective to treat the particular subject. The effective amount for any particular application may vary depending on such factors as the disease or condition being treated, the particular therapeutic agent(s) being administered, the size of the subject, or the severity of the disease or condition. One of ordinary skill in the art may determine empirically the effective amount of a particular therapeutic agent(s) without necessitating undue experimentation. In one embodiment, the highest safe dose according to some medical judgment is employed. The terms “dose” and “dosage” are used interchangeably herein.

For any compound described herein the therapeutically effective amount may be initially determined from preliminary in vitro studies and/or animal models. A therapeutically effective dose also may be determined from human data for therapeutic agent(s), which have been tested in humans and for compounds, which are known to exhibit similar pharmacological activities, such as other related active agents. The applied dose may be adjusted based on the relative bioavailability and potency of the administered compound. Adjusting the dose to achieve maximal efficacy based on the methods described above and other methods is well within the capabilities of the ordinarily skilled artisan.

According to some embodiments, the stabilized lipid-based glycopeptide antibiotic is administered in an amount greater than a minimum inhibitory concentration (MIC) for the pulmonary infection. For example, the MIC of the pulmonary infection is at least about 0.10 micrograms/mL, about 0.10 to 10 micrograms/mL, or about 0.10 to 5 micrograms/mL.

According to another embodiment, following administration of the stabilized lipid-based glycopeptide antibiotics, the $Log_{10}$ CFU (colony-forming unit) in the lung of the subject, or in sputum or tissue collected from the lung, are reduced. $Log_{10}$ CFU is the log value of colony-forming unit (CFU). In microbiology, colony-forming unit (CFU or cfu) refers to a measure of viable bacterial numbers. Unlike direct microscopic counts where all cells, dead and living, are counted, CFU measures viable cells. According to some embodiments, following administration of the stabilized lipid-based glycopeptide antibiotics, the $Log_{10}$ CFU in the lung of the subject can be reduced by at least about 0.5, about 1.0, about 1.5, about 2.0, or about 2.5. According to another embodiment, the total CFU in the lung is less than about 1.0, about 0.75, about 0.5, or about 0.25 after administration of the stabilized lipid-based glycopeptide antibiotic formulation. According to another embodiment, the pulmonary infection in the lung of the subject is reduced following administration of the stabilized lipid-based glycopeptide antibiotics. According to another embodiment, the pulmonary infection in the lung of the subject is eradicated following administration of the stabilized lipid-based glycopeptide antibiotics. According to another embodiment, the pulmonary infection is reduced more than by inhalation treatment with the same dose of free glycopeptide antibiotic. According to another embodiment, the rate of reduction or eradication of the pulmonary infection in a population of subjects is higher with treatment with the lipid based glycopeptide antibiotic formulation when compared to a population treated with the same dose of free inhaled glycopeptide antibiotic. According to another embodiment, the reduction of infection across a population treated with the inhaled stabilized glycopeptide antibiotic formulation is at least about 20, about 30, about 40, about 50, about 70, about 80, or about 90% greater when compared to treatment with inhaled free glycopeptide antibiotic. According to another embodiment, the pulmonary infection is reduced in a shorter period of time when compared to treatment with the same dose of inhaled free vancomycin. According to another embodiment, the time to recurrence of pulmonary infection or need for medical intervention is extended to a longer period of time when compared to treatment with the same dose of inhaled free vancomycin.

According to another embodiment, the stabilized lipid-based glycopeptide antibiotic of the described invention can be administered by inhalation as a nebulized spray, powder, or aerosol, or by intratracheal administration. According to another embodiment, the administration is less frequent and/or has an enhanced therapeutic index compared to inhalation of the free drug or a parenteral form of the drug. Additionally, the time for administering the desired therapeutic dose of glycopeptide antibiotic is reduced compared to inhalation of the free drug. Thus, in some embodiments, the lipid-based glycopeptide antibiotic formulation is more effective than inhalation of the same amount of the free drug. Liposomes or other lipid formulations are particularly advantageous due to their ability to protect the drug while being compatible with the lung lining or lung surfactant. While not being bound by any particular theory, it is believed that the lipid-based glycopeptide antibiotic formulation of the present invention has a depot effect in the lung. As such, the lipid-based glycopeptide antibiotic maintains its therapeutic bioavailability for a period of time after administration by inhalation is complete. According to some embodiments, this period of time is longer than the amount of time that free glycopeptide antibiotic remains therapeutically available. For example, the therapeutic bioavailability of the lipid-based glycopeptide antibiotic may be longer than 3, 4, 5, 6, 7, 8, 9 or 10 days after treatment, or even longer than two weeks after administration.

According to some embodiments, at least about 25% of the glycopeptide antibiotic is associated with the liposome after nebulization. According to another embodiment, at least about 50% or at least about 60% of the glycopeptide antibiotic is associated with the liposome after nebulization. According to another embodiment, about 50 to 95%, about 50 to 80% or about 60 to 75% of the glycopeptide antibiotic is associated with the liposome after nebulization.

According to some embodiments, the stabilized lipid-based glycopeptide antibiotic is administered intravenously, subcutaneously, orally, nasally, intraperitoneally, sublingually, bucally, transdermally, by subcutaneous or subdermal implantation, or intramuscularly.

According to some embodiments, the stabilized lipid-based glycopeptide antibiotic is administered by injection. According to further embodiments, the stabilized lipid-based glycopeptide antibiotic is administered by intravenous injection. According to another embodiment, the administration is less frequent and/or has an enhanced therapeutic index compared to injection of the free drug or a parenteral form of the drug. Additionally, the time for administering the desired therapeutic dose of glycopeptide antibiotic is reduced compared to injection of the free drug. Thus, in some embodiments, the lipid-based glycopeptide antibiotic formulation is more effective than injection of the same amount of the free drug. According to another embodiment, the time to recurrence of a bacterial infection or need for medical intervention is extended to a longer period of time when compared to treatment with the same dose of injected free vancomycin. According to some embodiments, the stabilized lipid-based glycopeptide antibiotic composition is administered at a dose of about 50 to 1000 mg/day, about 100 to 500 mg/day, or about 250 to 500 mg/day. According to another embodiment, the dose is about 100 mg/day. According to another embodiment, the dose is about 200 mg, about 300 mg, about 400 mg, or about 500 mg per day.

According to another embodiment, the stabilized lipid-based glycopeptide antibiotic composition is administered at a dose of from about 0.000001 mg/kg body weight to about 10 g/kg body weight. According to another embodiment, the stabilized lipid-based glycopeptide antibiotic composition is administered at a dose of from about 0.000002 mg/kg body weight to about 10 g/kg body weight. According to another embodiment, the stabilized lipid-based glycopeptide antibiotic composition is administered at a dose of from about 0.000003 mg/kg body weight to about 10 g/kg body weight. According to another embodiment, the stabilized lipid-based glycopeptide antibiotic composition is administered at a dose of from about 0.000004 mg/kg body weight to about 10 g/kg body weight. According to another embodiment, the stabilized lipid-based glycopeptide antibiotic composition is administered at a dose of from about 0.000005 mg/kg body weight to about 10 g/kg body weight. According to another embodiment, the stabilized lipid-based glycopeptide antibiotic composition is administered at a dose of from about 0.000006 mg/kg body weight to about 10 g/kg body weight. According to another embodiment, the stabilized lipid-based glycopeptide antibiotic composition is administered at a dose of from about 0.000007 mg/kg body weight to about 10 g/kg body weight. According to another embodiment, the stabilized lipid-based glycopeptide antibiotic composition is administered at a dose of from about 0.000008 mg/kg body weight to about 10 g/kg body weight. According to another embodiment, the stabilized lipid-based glycopeptide antibiotic composition is administered at a dose of from about 0.000009 mg/kg body weight to about 10 g/kg body weight. According to another embodiment, the stabilized lipid-based glycopeptide antibiotic composition is administered at a dose of from about 0.00001 mg/kg body weight to about 10 g/kg body weight. According to another embodiment, the stabilized lipid-based glycopeptide antibiotic composition is administered at a dose of from about 0.00002 mg/kg body weight to about 10 g/kg body weight. According to another embodiment, the stabilized lipid-based glycopeptide antibiotic composition is administered at a dose of from about 0.0003 mg/kg body weight to about 10 g/kg body weight. According to another embodiment, the stabilized lipid-based glycopeptide antibiotic composition is administered at a dose of from about 0.00004 mg/kg body weight to about 10 g/kg body weight. According to another embodiment, the stabilized lipid-based glycopeptide antibiotic composition is administered at a dose of from about 0.00005 mg/kg body weight to about 10 g/kg body weight. According to another embodiment, the stabilized lipid-based glycopeptide antibiotic composition is administered at a dose of from about 0.00006 mg/kg body weight to about 10 g/kg body weight. According to another embodiment, the stabilized lipid-based glycopeptide antibiotic composition is administered at a dose of from about 0.00007 mg/kg body weight to about 10 g/kg body weight. According to another embodiment, the stabilized lipid-based glycopeptide antibiotic composition is administered at a dose of from about 0.00008 mg/kg body weight to about 10 g/kg body weight. According to another embodiment, the stabilized lipid-based glycopeptide antibiotic composition is administered at a dose of from about 0.00009 mg/kg body weight to about 10 g/kg body weight. According to another embodiment, the stabilized lipid-based glycopeptide antibiotic composition is administered at a dose of from about 0.0001 mg/kg body weight to about 10 g/kg body weight. According to another embodiment, the stabilized lipid-based glycopeptide antibiotic composition is administered at a dose of about 0.0005 mg/kg body weight. According to another embodiment, the stabilized lipid-based glycopeptide antibiotic composition is administered at a dose of about 0.001 mg/kg body weight. According to another embodiment, the stabilized lipid-based glycopeptide antibiotic composition is administered at a dose of about 0.005 mg/kg body weight. According to another embodiment, the stabilized lipid-based glycopeptide antibiotic composition is administered at a dose of about 0.01 mg/kg body weight. According to another embodiment, the stabilized lipid-based glycopeptide antibiotic composition is administered at a dose of about 0.1 mg/kg body weight. According to another embodiment, the stabilized lipid-based glycopeptide antibiotic composition is administered at a dose of about 1 mg/kg body weight. According to another embodiment, the stabilized lipid-based glycopeptide antibiotic composition is administered at a dose of about 10 mg/kg body weight. According to another embodiment, the stabilized lipid-based glycopeptide antibiotic composition is administered at a dose of about 20 mg/kg body weight. According to another embodiment, the stabilized lipid-based glycopeptide antibiotic composition is administered at a dose of about 30 mg/kg body weight. According to another embodiment, the stabilized lipid-based glycopeptide antibiotic composition is administered at a dose of about 40 mg/kg body weight. According to another embodiment, the stabilized lipid-based glycopeptide antibiotic composition is administered at a dose of about 50 mg/kg body weight. According to another embodiment, the stabilized lipid-based glycopeptide antibiotic composition is administered at a dose of about 60 mg/kg body weight. According to another embodiment, the stabilized lipid-based glycopeptide antibiotic composition is administered at a dose of about 70 mg/kg body weight. According to another embodiment, the stabilized lipid-based glycopeptide antibiotic composition is administered at a dose of about 80 mg/kg body weight. According to another embodiment, the stabilized lipid-based glycopeptide antibiotic composition is administered at a dose of about 90 mg/kg body weight. According to another embodiment, the stabilized lipid-based glycopeptide antibiotic composition is administered at a dose of about 100 mg/kg body weight. According to another embodiment, the stabilized lipid-based glycopeptide antibiotic composition is administered at a dose of about 110 mg/kg body weight. According to another embodiment, the stabilized lipid-based glycopeptide antibiotic composition is administered at a dose of about 120 mg/kg body weight. According to another embodiment, the stabilized lipid-based glycopeptide antibiotic composition is administered at a dose of about 130 mg/kg body weight. According to another embodiment, the stabilized lipid-based glycopeptide antibiotic composition is administered at a dose of about 140 mg/kg body weight. According to another embodiment, the stabilized lipid-based glycopeptide antibiotic composition is administered at a dose of about 150 mg/kg body weight. According to another embodiment, the stabilized lipid-based glycopeptide antibiotic composition is administered at a dose of about 160 mg/kg body weight. According to another embodiment, the stabilized lipid-based glycopeptide antibiotic composition is administered at a dose of about 170 mg/kg body weight. According to another embodiment, the stabilized lipid-based glycopeptide antibiotic composition is administered at a dose of about 180 mg/kg body weight. According to another embodiment, the stabilized lipid-based glycopeptide antibiotic composition is administered at a dose of about 190 mg/kg body weight. According to another embodiment, the stabilized lipid-based glycopeptide antibiotic composition is administered at a dose of about 200 mg/kg body weight. According to another embodiment, the stabilized lipid-based glycopeptide antibiotic composition is administered at a dose of about 250 mg/kg body weight. According to another embodiment, the stabilized lipid-based glycopeptide antibiotic composition is administered at a dose of about 500 mg/kg body weight.

According to some embodiments, the stabilized lipid-based glycopeptide antibiotic composition is administered intratracheally. According to another embodiment, the stabilized lipid-based glycopeptide antibiotic composition is administered via inhalation. According to some embodiments, the stabilized lipid-based glycopeptide antibiotic composition is administered via a nebulizer. According to another embodiment, administering occurs parenterally. According to another embodiment, administering occurs intravenously. According to another embodiment, administering occurs intramuscularly. According to another embodiment, administering occurs intraperitoneally.

According to another embodiment, the composition is administered 1 time to 4 times a day. According to another embodiment, the composition is administered once a day, twice a day, three times a day or four times a day. According to another embodiment, the composition is administered in a daily treatment cycle for a period of time, or is administered in a cycle of every other day, every third day, every fourth day, every fifth day, every $6^{th}$ day or once a week for a period of time, the period of time being from one week to several months, for example, 1, 2, 3, or 4 weeks, or 1, 2, 3, 4, 5, or 6 months.

The described invention may be embodied in other specific forms without departing from the spirit or essential attributes thereof and, accordingly, reference should be made to the appended claims, rather than to the foregoing specification, as indicating the scope of the invention.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Unless indicated otherwise, parts are parts by weight, molecular weight is weight average molecular weight, temperature is in degrees Centigrade, and pressure is at or near atmospheric.

Example 1. Vancomycin Stability in Aqueous Solution Reagents and Equipment

Cholesterol (Cat. No. 700000P) and dipalmitoylphosphatidylcholine (DPPC, Cat. No. 850355P) were purchased from Avanti Polar Lipids Certified Reference Standard. Vancomycin Chloride (Lot HVN0701303) was purchased from North China Pharmaceutical Group. Methanol (HPLC grade, Cat No. AH230-4), Acetonitrile (HPLC grade), Ammonium Hydroxide (HPLC grade) were purchased from Burdick & Jackson. Glacial Acetic Acid (HPLC grade; JT9515-3) and Sodium Chloride (ACS Reagent; Cat. No. 3628-05) were purchased from JT Baker. Purified water was prepared by using Milli-Q 18.0 MΩ water.

High Performance Liquid Chromatography (HPLC) is from Shimadzu (10 AVP equipped UV-detector and CORONA Charged Aerosol Detector (CAD) and HPLC software is from LC Solutions™. Refrigerated multipurpose centrifuge (5810R) is from Eppendorf (Westbury, N.Y.).

Vancomycin Normal Phase HILIC HPLC Assay

A vancomycin Normal Phase HILIC HPLC assay was performed using a Shimadzu 10AVP HPLC system equipped with UV detector (CAD optional) under the following conditions:
 Column: ZIC-HILIC 150×4.6 mm, 3.5 um, 200 A (SeQuant)
 Column temperature: 30 C
 Mobile phase: Acetonitrile 37%, Methanol 24%, water 39%, Acetic acid 0.08%, Ammonium hydroxide 0.02%
 Flow rate: 0.5 mL/min, Isocratic
 Injection volume: 20 μL
 Samples are dissolved in mobile phase. A mix of mobile phase with n-propanol 4:1 can be used when preparing lipid containing samples.
 Vancomycin standards: useful range 10-200 mg/mL, dissolved in mobile phase. Calibration curve is fitted by a linear function
 UV detector: Wavelength 280 nm
 Chromatogram: retention time for
  CDP-I-M: about 14 min
  CDP-I-m: about 16 min
  Vancomycin: about 24 min
  additional major peaks are at: 20, 22, 27 min. Total recording time 35 min Vancomycin Reverse Phase HPLC Assay A vancomycin Reverse phase HPLC assay (which cannot be used for lipid containing samples) was performed using a Shimadzu 10AVP HPLC system equipped with UV detector (CAD optional) under the following conditions:
 Column: Atlantis-® dC18, 5μ, 250×4.6 mm (Waters)
 Mobile phase A: acetonitrile 5%, ammonium acetate 15 mM, pH 6.0. Mobile phase B: acetonitrile 20%, ammonium acetate 15 mM, pH 6.0. Ammonium acetate 1 M solution pH 6.0: approximately 6% glacial acetic acid (1 M) and 9% ammonium hydroxide 30% solution.
 Flow rate: 1 mL/min, Binary gradient

| Time (minutes) | Solvent B (%) |
| --- | --- |
| 0 | 15 |
| 15 | 20 |
| 25 | 35 |
| 35 | 60 |
| 40 | 100 |
| 45 | 100 |
| 50 | 15 |
| 55 | 15 |

Injection volume: 20 ILL
 Samples are dissolved in mobile phase.
 Vancomycin standards: useful range 10-200 mg/mL, dissolved in mobile phase. Calibration curve is fitted by a linear function
 UV detector: Wavelength 280 nm
 Chromatogram: retention time for
  CDP-I-M: about 7 min
  CDP-I-m: about 16 min
  Vancomycin: about 26 min
  Total recording time 55 min Vancomycin Assay by UV-Vis The samples to be analyzed were dissolved in n-propanol/$H_2O$ solution (60/40, vol/vol) so that the final vancomycin HCl concentrations were between 0 μg/ml and 200 μg/ml. Pre-dilution with $H_2O$ may be necessary if the vancomycin concentration in the original sample is >10 mg/mL. The concentrations of the samples were calculated by comparing their absorbance at 280 nm with that of a linear standard curve (standards were prepared from raw material at 0, 50, 100, 150 and 200 g/ml).

Alternatively, samples were dissolved in the mobile phase used for the HILIC HPLC method mixed with n-propanol at 3:1 vol. In the latter case, the vancomycin extinction coefficient was 5.4 mg/mL$^{-1}$ cm$^{-1}$, or about 7800 M$^{-1}$ cm$^{-1}$ (1 A per 185 μg/ml)

Lipid HPLC Assay

A lipid HPLC assay was performed using a Shimadzu 10AVP HPLC system equipped with a Corona Charge Aerosol Detector (CAD) under the following conditions and parameters:

Column: Phenomenex Luna 3μ, C8(2), 75×4.6 mm
Column temperature: 30° C.
Mobile phase: Acetonitrile 43%, n-Propanol 43%, water 14%, Acetic acid 0.1%, TEA 0.1%
Flow rate: 1 mL/min, Isocratic
Injection volume: 20 μL
Samples were dissolved in Solution A: Acetonitrile 30%, n-Propanol 30%, water 40%
Lipid standards (DPPC/Cholesterol 20/10, 30/15, and 40/20 μg/mL)
Calibration is fitted by a linear function
Chromatogram: retention time for cholesterol~4 min, DPPC~6 min, total recording time 10 min Samples of Vancomycin Solution for Stability Study Vancomycin solution samples (1 mL of 200 mg/mL) were put in 4 mL glass vials and incubated at the indicated temperature. Selected samples were also incubated at a lower concentration (20 mg/mL).

Normal Phase HILIC HPLC Assay for Vancomycin

Previously, a reverse phase HPLC assay was developed and used in the first study on development of liposomal vancomycin (U.S. Publication No. US 2009-0104257, entitled "Liposomal Vancomycin Formulations," which is incorporated herein by reference in its entirety). The method employed an Atlantis® dC18 column (Waters) and used a binary mobile phase gradient with Acetonitrile concentration changing 7% to 20% in water. The mobile phase, however, was too polar to dissolve lipid containing samples. Organic phase extraction was tried but had challenges.

Figure 4:
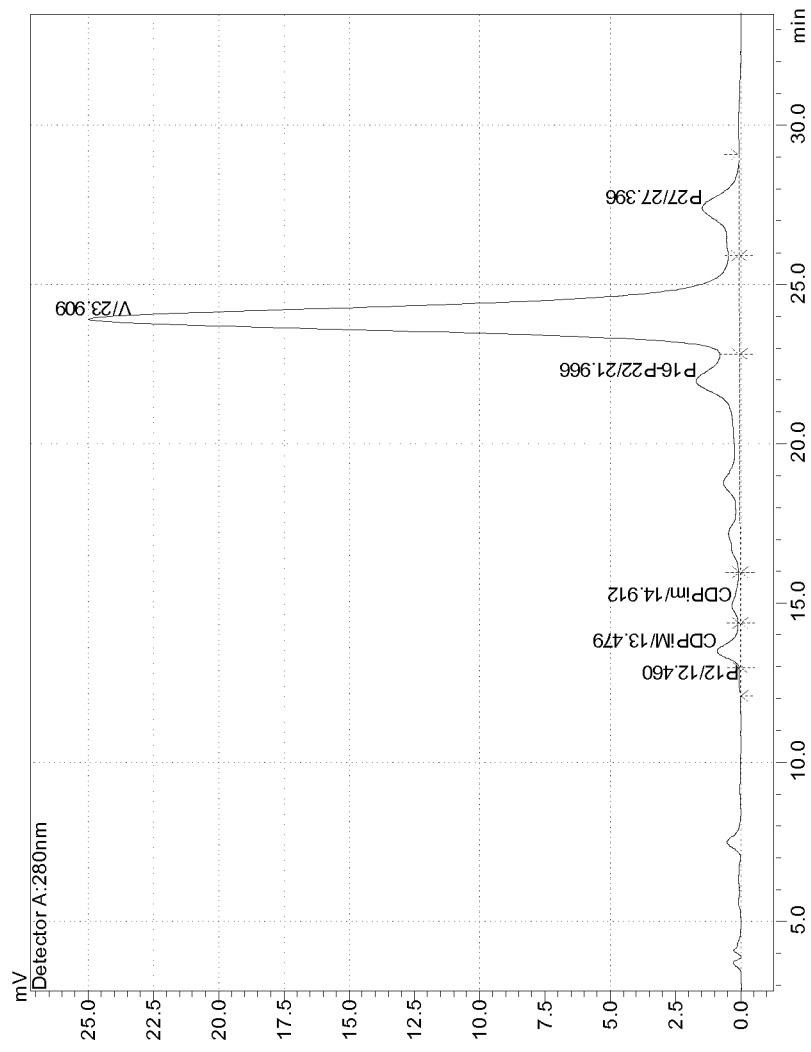
FIG. 4 is a typical chromatogram of vancomycin using a ZIC-HILIC column. CDP-I-M, CDP-I-m, and Vancomycin peaks are shown at retention times of 13, 5, 4.9, and 23.9, respectively.

In the present invention, a new assay, i.e., Normal phase HILIC (Hydrophilic Interaction Liquid Chromatography) HPLC assay was developed. The new assay utilizes a ZIC-HILIC column (SeQuant) and separates compounds by polar differences. Moreover, the HILIC method can use less polar mobile phase and thus is able to dissolve both vancomycin and lipid (see Materials and Methods section). Particularly, the mobile phase was selected as: Acetonitrile 37%, Methanol 24%, water 39%. Acetic acid 0.08%, Ammonium hydroxide 0.02%. The drawbacks of this method are: high (but manageable) sensitivity to mobile phase composition, and wider peaks compared to RP assay. See FIG. 4 for a typical chromatograph.

Chemical Stability of Vancomycin in Aqueous Solution

Samples of vancomycin solutions at a concentration of 200 mg/mL and pH 5.0, 5.5, 6.0, and 6.5 were prepared by adding the appropriate amount of NaOH solution (50 mM or 100 mM). In buffered samples, an appropriate amount of buffer or amino acid additive was added. The pH values were chosen to cover the range between the lowest and highest acceptable values of pH, including pH 5.0 for lipid stability reasons and pH 6.5, above which degradation is expected to be impractically fast.

The concentration of 200 mg/mL was chosen to mimic what a high intra-liposomal might be but was no higher than this for practical handling purposes. All samples were liquid solutions upon preparation. During incubation, most samples turned into a gel-like consistency and later solidified further into a wax-like form. In some samples with a high level of degradation, crystal granules were observed embedded in the formed gel.

The Experiment was started with vancomycin samples, in which pH was adjusted by adding NaOH or an organic base (e.g., Tris-base, Ethanol Amine (EOA), or Tri-Ethanol Amine (TEOA)) as shown in Table 7. For comparison, lower concentration solutions (20 mg/mL) also were prepared by diluting 200 mg/mL samples 10-fold in water. Samples were incubated at 4° C. (in refrigerator) and at ambient temperature (about 23° C., which is referred herein to as "room temperature" or "RT").

TABLE 7

Samples with pH adjusted by NaOH or organic bases

| Base Used | pH | Base added mol/mol |
|---|---|---|
| NaOH | 5.0 | 0.16 |
| | 5.5 | 0.18 |
| | 6.0 | 0.20 |
| | 6.5 | 0.28 |
| TRIS | 6.0 | 0.22 |
| | 6.5 | 0.31 |
| TEOA | 6.0 | 0.23 |
| EOA | 6.5 | 0.30 |

TEOA (Tri-Ethanol amine),
EOA (Ethanol amine)

TABLE 8

Degradation of vancomycin: Effect of pH, presence of organic buffers, ethanol, and ammonium ions, Temperature = 4° C.

| | (CDPI-m + CDPI-M) % at week: | | | | | | Slope | |
|---|---|---|---|---|---|---|---|---|
| Sample | 0 | 1 | 2 | 4 | 8 | 12 | %/w | R^2 |
| 200 mg/mL | | | | | | | | |
| NaOHpH5 | 0.5 | 0.68 | 0.74 | 0.93 | 1.40 | 1.54 | 0.09 | 0.97 |
| NaOHpH55 | 0.5 | 0.73 | 1.07 | 1.11 | 1.67 | 2.39 | 0.15 | 0.98 |
| NaOHpH6 | 0.5 | 0.74 | 1.38 | 1.69 | 2.60 | 2.90 | 0.20 | 0.94 |
| NaOHpH65 | 0.5 | 1.07 | 1.66 | 2.55 | 5.78 | 4.46 | 0.39 | 0.78 |
| NaOHpH5 + NH4Cl | 0.5 | 0.77 | 0.80 | 0.92 | 1.60 | 1.77 | 0.11 | 0.96 |
| NaOHpH6 | 0.5 | 0.74 | 1.38 | 1.69 | | | 0.31 | 0.92 |
| NaOHpH6 + EtOH | 0.5 | 0.67 | 1.19 | 2.28 | | | 0.46 | 0.97 |
| TrispH6 | 0.5 | 0.69 | 1.47 | 1.82 | | | 0.35 | 0.91 |
| TEOApH6 | 0.5 | 0.79 | 1.04 | 2.11 | | | 0.40 | 0.97 |
| EOApH6 | 0.5 | 0.79 | 1.22 | 2.19 | | | 0.43 | 0.99 |
| NaOHpH6.5 | 0.5 | 1.07 | 1.66 | 2.55 | | | 0.51 | 0.99 |
| NaOHpH6.5 + EtOH | 0.5 | 0.93 | 2.06 | 2.15 | | | 0.43 | 0.81 |
| TrispH6.5 | 0.5 | 1.32 | 2.20 | 2.78 | | | 0.56 | 0.93 |
| TEOApH6.5 | 0.5 | 1.15 | 1.78 | 2.87 | | | 0.59 | 1.00 |
| EOApH6.5 | 0.5 | 0.98 | 1.94 | 3.08 | | | 0.66 | 0.99 |
| 20 mg/mL | | | | | | | | |
| NaOHpH5 | 0.5 | 0.90 | 1.24 | 1.69 | 3.29 | 4.52 | 0.34 | 1.00 |
| NaOHpH55 | 0.5 | 1.23 | 1.34 | 2.29 | 3.59 | 4.80 | 0.35 | 0.99 |
| NaOHpH6 | 0.5 | 1.34 | 1.61 | 2.09 | 3.09 | 3.31 | 0.22 | 0.90 |
| NaOHpH65 | 0.5 | 1.11 | 2.05 | 2.97 | 2.16 | 2.42 | 0.12 | 0.38 |

Figure 5:
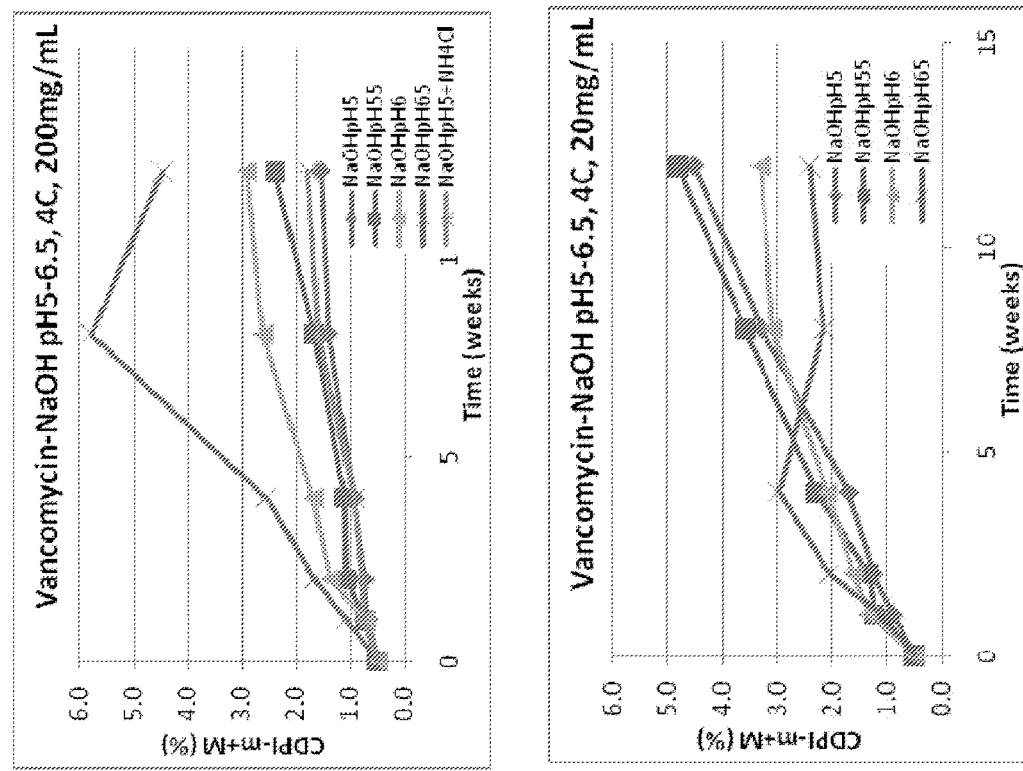
FIG. 5 is a graph of vancomycin degradation over time at pH of 5, 5.5, 6, or 6.5, at 4° C., and at a concentration of 200 mg/mL (top panel) or 20 mg/mL (bottom panel).
Figure 6:
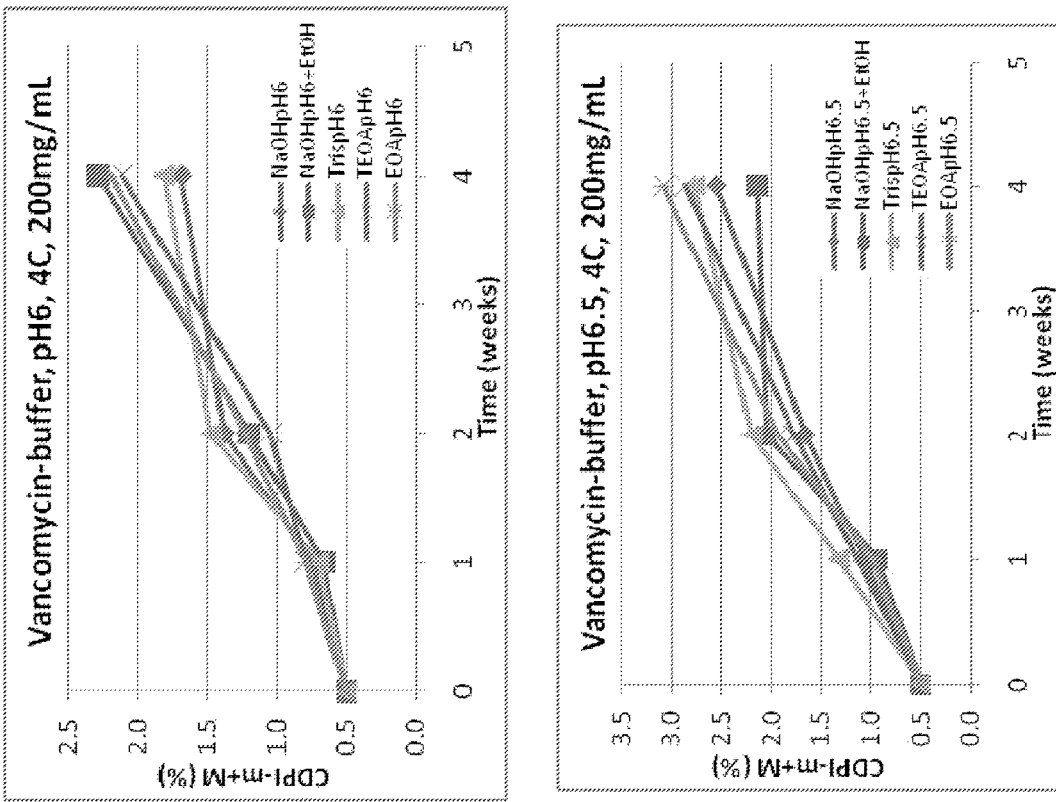
FIG. 6 is a graph of vancomycin degradation over time in NaOH (diamonds); NaOH with EtOH (squares); Tris-base (triangle symbols); Tri-Ethanol Amine (TEOA; Xs); or Ethanol Amine (EOA; asterisks) at 4° C. and at pH 6 (top panel) or pH 6.5 (bottom panel).

A higher concentration and lower pH, vancomycin was more stable (Table 8, FIG. 5). At low concentration, the effect seemed to be unclear or even reversed. The main difference in low and high concentration samples was their physical state. At high concentration vancomycin over time formed a gel-like structure. At low concentration, it stayed liquid until a white precipitate started to form. Excluding sodium ions and using instead organic buffer bases to adjust pH did not change degradation kinetics noticeably (FIG. 6).

Figure 7:
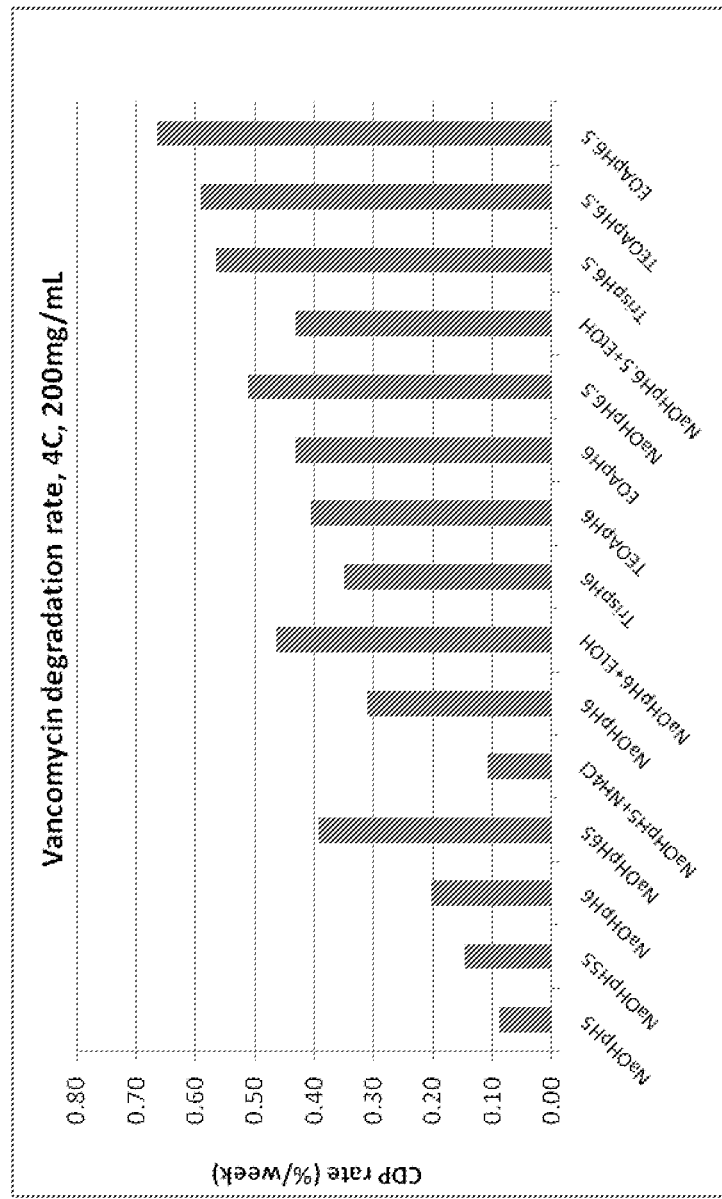
FIG. 7 is a bar graph of the rate of degradation of vancomycin at 4° C. in the presence of the indicated organic buffers at the indicated pH.

Overall, the summary plot in FIG. 7 shows that at high concentration and low pH vancomycin can be somewhat stable with a degradation rate of about 0.1% per week. This, however, is not believed to be good enough to develop a practical commercial product. Addition of an equimolar amount of ammonium ions (NH$_4$Cl) did not improve vancomycin stability. Ethanol at 10% efficiently prevented vancomycin gelation and precipitation, but again did not slow down its degradation rate.

Figure 8:
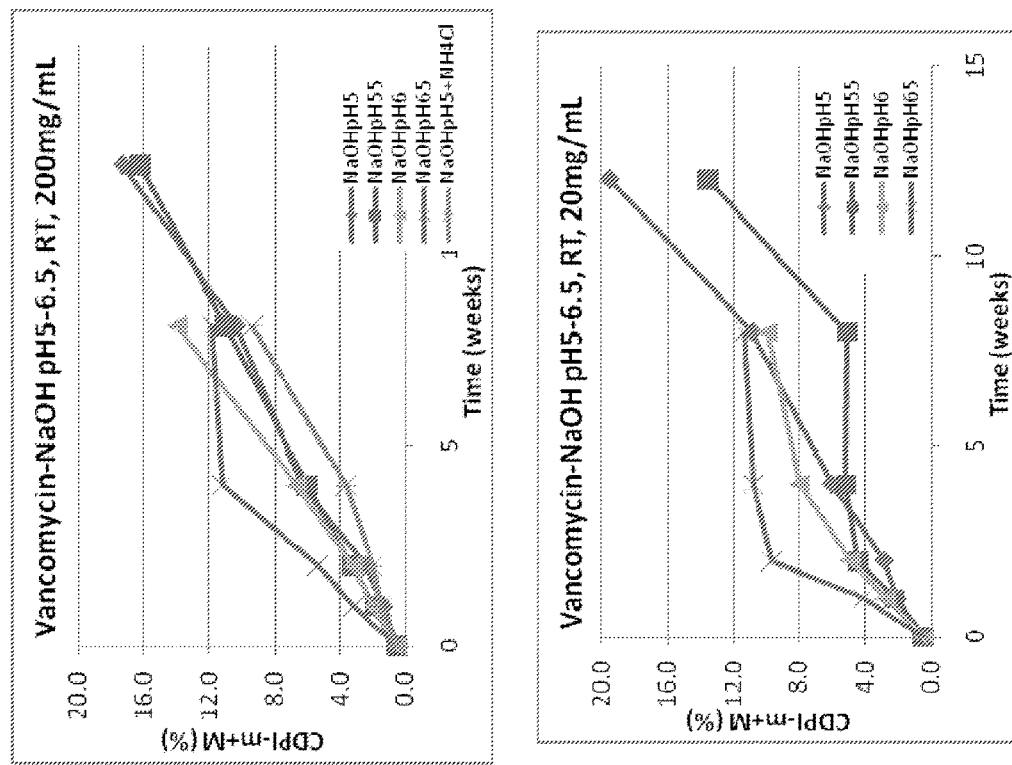
FIG. 8 is a graph of the degradation of vancomycin over time at pH of 5, 5.5, 6, or 6.5, at room temperature (RT), and at a concentration of 200 mg/mL (top panel) or 20 mg/mL (bottom panel).
Figure 9:
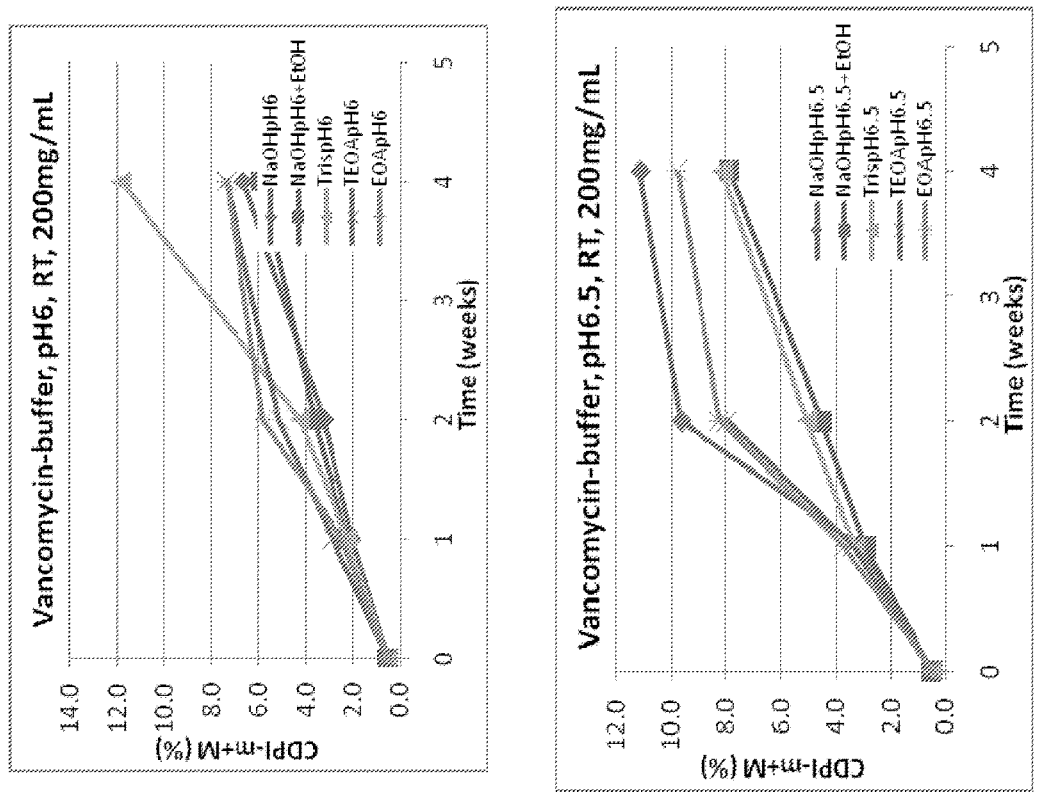
FIG. 9 is a graph of the degradation of vancomycin over time in the presence of NaOH (diamonds); NaOH with EtOH (squares); Tris-base (triangles); Tri-Ethanol Amine (TEOA; Xs); or Ethanol Amine (EOA; asterisks), at room temperature (RT), and at pH 6 (top panel) or pH 6.5 (bottom panel).
Figure 10:
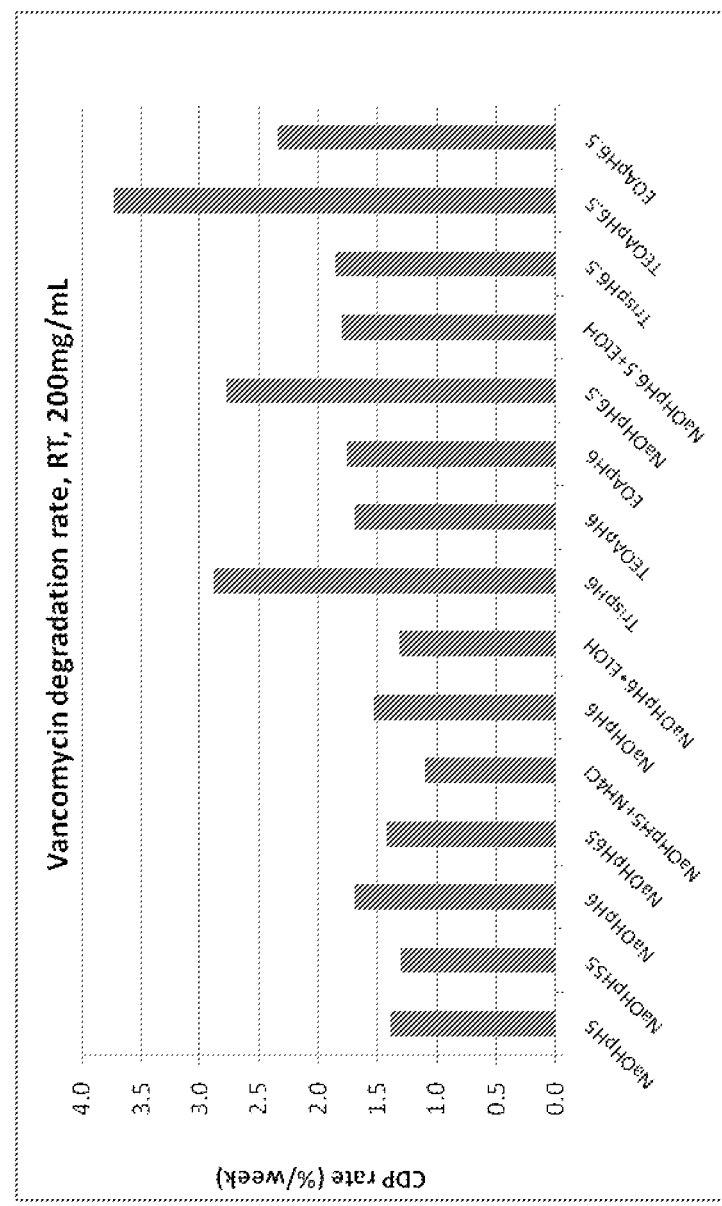
FIG. 10 is a graph of vancomycin degradation rates at room temperature (RT) in the presence of the indicated organic buffers and at the indicated pH.

At room temperature, degradation rates were about tenfold higher but the data showed greater variability (Table 9 and FIGS. 8-10).

TABLE 9

The Effect of pH, presence of organic buffers, ethanol, and ammonium ions on degradation of vancomycin at room temperature (RT)

| Sample | (CDPI-m + CDPI-M) % at week: | | | | | | Slope | |
|---|---|---|---|---|---|---|---|---|
| | 0 | 1 | 2 | 4 | 8 | 12 | %/w | $\hat{R}2$ |
| 200 mg/mL | | | | | | | | |
| NaOHpH5 | 0.5 | 1.34 | 2.47 | 6.28 | 10.37 | 17.3 | 1.39 | 0.99 |
| NaOHpH55 | 0.5 | 1.86 | 3.30 | 5.97 | 11.0 | 16.2 | 1.30 | 1.00 |
| NaOHpH6 | 0.5 | 2.04 | 3.23 | 6.66 | 14.0 | | 1.69 | 1.00 |
| NaOHpH65 | 0.5 | 3.16 | 5.36 | 11.1 | 11.8 | | 1.42 | 0.83 |
| NaOHpH5 + NH4Cl | 0.5 | 1.49 | 1.99 | 3.63 | 9.4 | | 1.10 | 0.97 |
| NaOHpH6 | 0.5 | 2.04 | 3.23 | 6.66 | | | 1.53 | 1.00 |
| NaOHpH6 + EtOH | 0.5 | 2.27 | 3.65 | 5.86 | | | 1.32 | 0.99 |
| TrispH6 | 0.5 | 2.25 | 4.23 | 11.9 | | | 2.88 | 0.96 |
| TEOApH6 | 0.5 | 2.85 | 5.12 | 7.36 | | | 1.70 | 0.96 |
| EOApH6 | 0.5 | 2.45 | 5.79 | 7.38 | | | 1.75 | 0.92 |
| NaOHpH6.5 | 0.5 | 3.16 | 9.65 | 11.1 | | | 2.77 | 0.86 |
| NaOHpH6.5 + EtOH | 0.5 | 2.92 | 4.51 | 7.87 | | | 1.80 | 0.99 |
| TrispH6.5 | 0.5 | 3.32 | 5.05 | 8.16 | | | 1.86 | 0.98 |
| TEOApH6.5 | 0.5 | 3.38 | 7.97 | | | | 3.73 | 0.98 |
| EOApH6.5 | 0.5 | 3.70 | 8.25 | 9.79 | | | 2.34 | 0.88 |
| Temp RT | | | | | | | | |
| NaOHpH5 | 0.5 | 2.12 | 2.87 | 6.03 | 10.8 | 19.5 | 1.53 | 0.98 |
| NaOHpH55 | 0.5 | 2.22 | 4.44 | 5.15 | 5.08 | 13.6 | 0.89 | 0.84 |
| NaOHpH6 | 0.5 | 2.80 | 4.89 | 7.97 | 9.85 | | 1.13 | 0.89 |
| NaOHpH65 | 0.5 | 4.16 | 9.65 | 10.8 | 11.3 | | 1.20 | 0.64 |

There was no clear effect of buffers, ammonium ions, or added ethanol. The high variability in data might be explained by the non-homogeneous nature of samples after long incubation at room temperature. Samples solidified and exhibited a number of crystalline granules embedded within. Taking an aliquot of sample for analysis often resulted in getting a portion of sample of varying consistency.

Example 2. Effect of Amino Acid Additives on Chemical Stability of Vancomycin

It has been known that some peptides as short as two or three amino acids can bind tightly to vancomycin and thus stabilize its structure against deamidation (Harris et al., 1985, J. Antibiot, 38(1):51-7). Two such peptides have been identified, i.e., Ac-D-Ala-D-Ala and Di-Ac-L-Lys-D-Ala-D-Ala. While they potentially could be used to provide improved vancomycin stability, they are not cost-effective means of improving vancomycin stability.

Below is a list of amino acids identified for testing (Table 10). Amino acids were added on a mole per mole base unless otherwise stated. Final pH was adjusted to pH 5.0 or pH 5.5 where indicated by adding an appropriate amount of NaOH. Samples at a concentration 200 mg/mL were placed 1 mL each into 4 mL glass vials and incubated at a certain controlled temperature. Samples were analyzed by HILIC HPLC, and CDP % was calculated as a sum of CDP-I-m and CDP-1-M % to total vancomycin and its products.

TABLE 10

Amino Acids And Derivatives Used In Stability Study.

| Amino acid | Chemical structure |
|---|---|
| ALA-ALA | 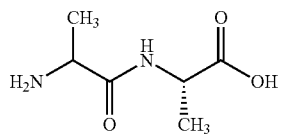 |
| GLY, Glycine | 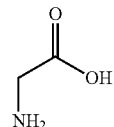 |
| ALA, Alanine<br>2-Aminopropionic acid | 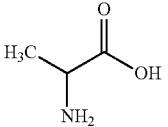 |
| bALA, beta-Alanine<br>3-Aminopropionic acid | 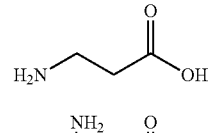 |
| 3-ABA<br>3-Aminobutanoic acid | 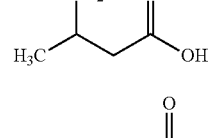 |
| GABA<br>4-Aminobutanoic acid | 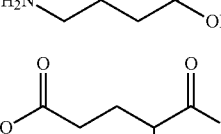 |
| GLU, Glutamic acid<br>2-Aminopentanedioic acid | 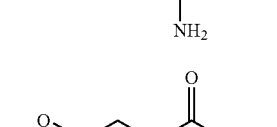 |
| ASP, Aspartic acid<br>2-Aminobutanedioic acid | 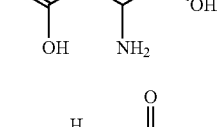 |
| Sarcosine<br>N-Methylglycine | 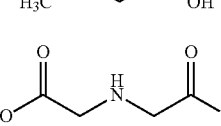 |
| IDAA<br>Iminodiacetic acid | 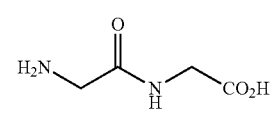 |
| GLY-GLY<br>Glycyl-glycine | 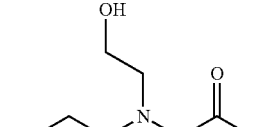 |
| Bicine | 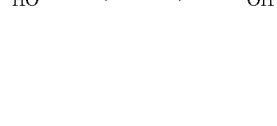 |

TABLE 10-continued

Amino Acids And Derivatives Used In Stability Study.

| Amino acid | Chemical structure |
|---|---|
| Tricine | (structure: tris(hydroxymethyl)methylglycine) |

Figure 11:
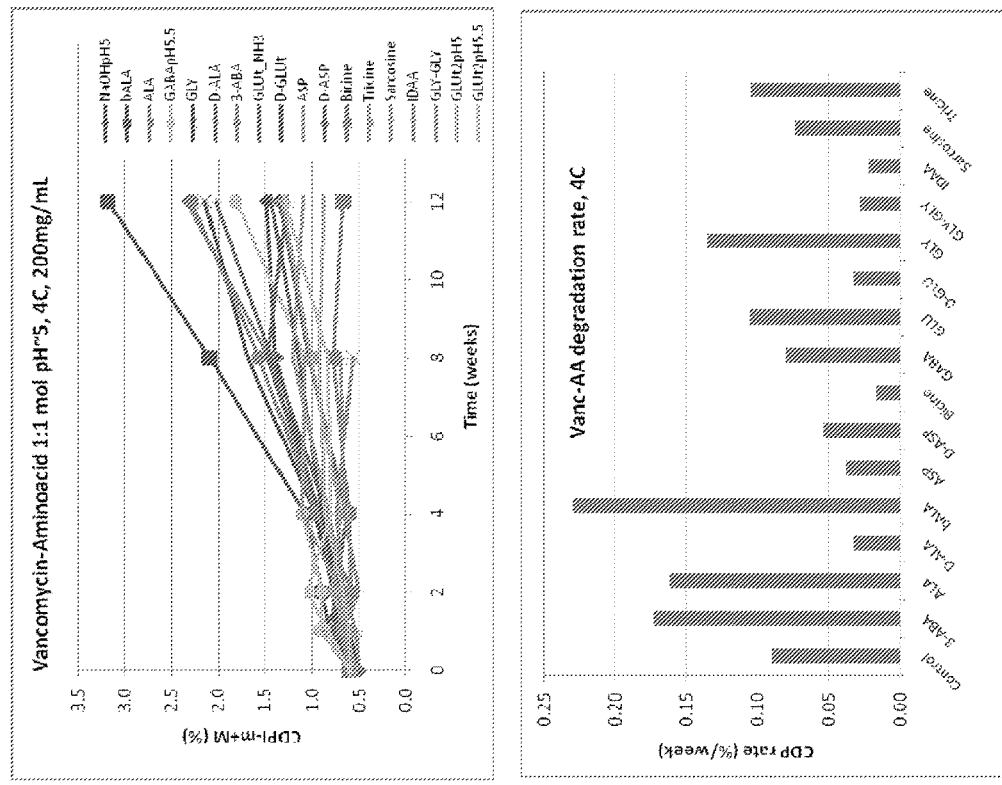
FIG. 11 is a graph of vancomycin degradation over time (top panel) and vancomycin degradation rates (bottom panel) in vancomycin compositions with the indicated amino acid or derivative thereof at 4° C. Amino acids were added on a mole per mole basis unless otherwise stated. In the top panel, the vancomycin compositions comprise: control (NaOH alone, pH 5, dark diamonds); bALA (dark squares); ALA (dark triangles); GABA, pH5.5 (light circles); GLY (dark line with X symbols); D-ALA (dark line with asterisk symbols); 3-ABA (dark circles); GLU (dark line with plus symbols); G-GLU (dark line with no symbols); ASP (medium line with no symbols); D-ASP (light diamonds); bicine (light squares); tricine (light triangles); sarcosine (light line with Xs); IDAA (light line with asterisks); GLY-GLY (light line with plus symbols); GLU, pH 5 (2:1 ratio of GLU-vancomycin, pH5; lighter line with no symbols); and GLU, pH5.5 (2:1 ratio of GLU-vancomycin, pH5.5; lightest line with no symbols).

A detailed stability data table at 4° C. is presented in Table 11 and FIG. 11. A significant difference was found in the rate of degradation, with the worst rate found for samples incubated with L-ALA, b-ALA, 3-ABA, and GLY. At the same time, great improvement was seen when using Bicine, Imino-diacetic acid (IDAA), glycylglycine (GLY-GLY), and GLU at 2:1 mol ratio with vancomycin. A rate of as low as 0.01% per week was observed for some compounds, including Bicine, IDAA, and GLY-GLY. In comparison, control compounds that do not comprise an amino acid or derivative thereof exhibited a rate of 0.09%. Thus, the stabilized glycopeptide antibiotic composition comprising an amino acid such as, for example, Bicine. IDAA, or GLY-GLY was at least 88% more stable at 4° C. than a glycopeptide antibiotic that does not comprise an amino acid or derivative thereof.

TABLE 11

Degradation of vancomycin data table: Effect of amino additives at 4° C.

| Amino acid added | (CDPI-m + CDPI-M) % at week: | | | | | | Slope |
|---|---|---|---|---|---|---|---|
| | 0 | 1 | 2 | 4 | 8 | 12 | %/w |
| NaOHpH5 | 0.50 | 0.61 | 0.69 | 0.98 | 1.39 | 1.49 | 0.00 |
| bALA | 0.60 | 0.81 | 0.80 | 1.07 | 2.09 | 3.18 | 0.21 |
| ALA | 0.60 | 0.69 | 0.76 | 0.97 | 1.46 | 2.34 | 0.14 |
| GABApH5.5 | 0.60 | 0.91 | 0.89 | 1.11 | 1.08 | 1.81 | 0.08 |
| GLY | 0.60 | 0.76 | 0.77 | 0.96 | 1.68 | 2.14 | 0.13 |
| D-ALA | 0.60 | 0.74 | 0.70 | 0.92 | 1.48 | 1.27 | 0.07 |
| B-ABA | 0.60 | 0.65 | 0.57 | 0.85 | 1.57 | 2.29 | 0.15 |
| GLUt_NH3 | 0.60 | 0.83 | 0.72 | 0.84 | 1.44 | 2.08 | 0.12 |
| D-GlUt | 0.60 | 0.68 | 0.75 | 0.89 | 1.14 | 1.43 | 0.07 |
| ASP | 0.60 | 0.75 | 0.65 | 0.82 | 1.20 | 1.09 | 0.05 |
| D-ASP | 0.60 | 0.74 | 0.74 | 0.63 | 1.03 | 1.35 | 0.06 |
| Bicine | 0.60 | 0.66 | 0.58 | 0.61 | 0.77 | 0.67 | 0.01 |
| Tricine | 0.60 | 0.62 | 0.78 | 0.69 | 1.02 | 1.32 | 0.06 |
| Sarcosine | 0.54 | 0.69 | 0.70 | 1.11 | 1.08 | | 0.07 |
| IDAA | 0.50 | 0.54 | 0.66 | 0.74 | 0.56 | | 0.01 |
| GLY-GLY | 0.60 | 0.66 | 0.50 | 0.66 | 0.69 | | 0.01 |
| GLUt2pH5 | 0.60 | 0.61 | 0.67 | 0.86 | 0.92 | 0.87 | 0.03 |
| GLUt2pH5.5 | 0.60 | 0.82 | 1.06 | 0.79 | 0.83 | 1.29 | 0.04 |

TABLE 12

Degradation of vancomycin data table: Rate of degradation at 4° C. with amino acid additives relative to control.

| Amino acid | Structure | Rate of degradation relative to control |
|---|---|---|
| D-ALA D-Alanine | (structure) | 0.36% weight/week |
| ASP Aspartic acid | (structure) | 0.42% weight/week |
| Bicine | (structure) | 0.18% weight/week |
| D-GLU D-Glutamic acid | (structure) | 0.37% weight/week |
| GLY-GLY Glycylglycine | (structure) | 0.31% weight/week |
| IDAA Iminodiacetic acid | (structure) | 0.24% weight/week |

Figure 12:
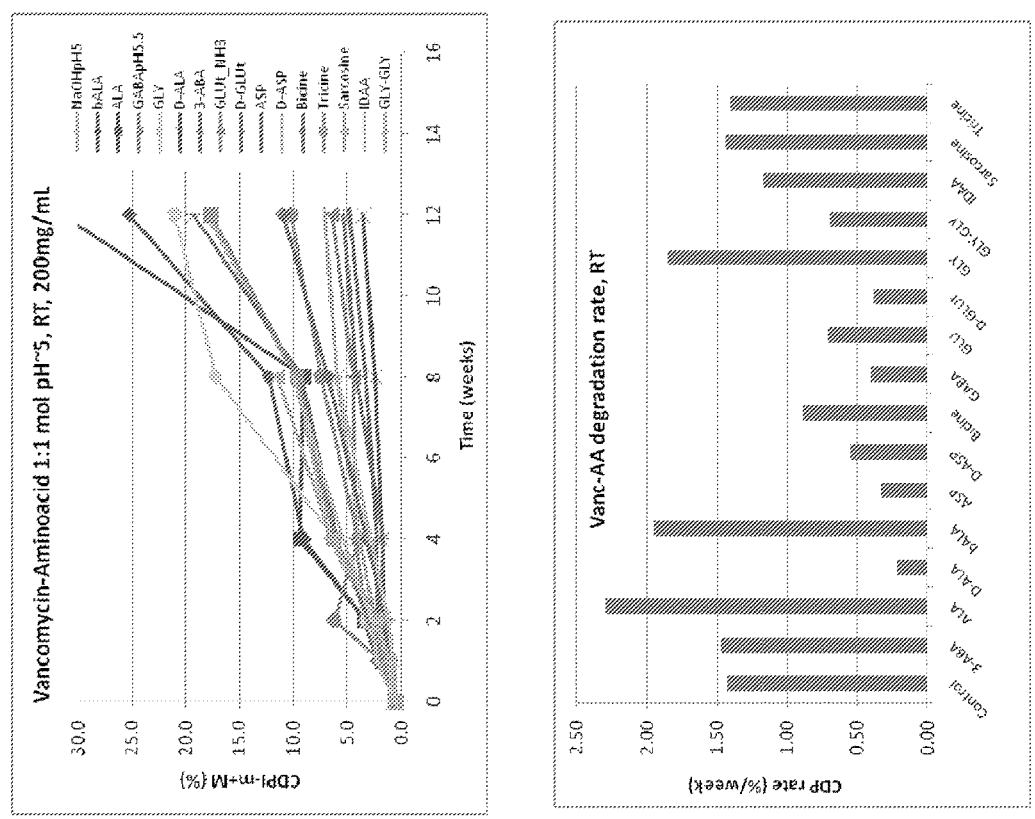
FIG. 12 is a graph of vancomycin degradation over time (top panel) and vancomycin degradation rates (bottom panel) in vancomycin compositions with the indicated amino acid or derivative thereof at RT. Amino acids were added on a mole per mole base unless otherwise stated. In the top panel, the vancomycin compositions comprise: control (NaOH alone, pH 5, light line with plus symbol); bALA (dark diamonds); ALA (dark squares); GABA, pH5.5 (dark triangles); GLY (light circles); D-ALA (dark line with X symbols); 3-ABA (dark line with asterisk symbols); GLUt (dark circles); G-GLUt (dark line with plus symbols); ASP (dark line with no symbols); D-ASP (medium line with no symbols); bicine (light diamonds); tricine (light squares); sarcosine (light triangles); IDAA (light line with asterisk symbols); GLY-GLY (light line with plus symbols); GLU pH5 (2:1 ratio of GLU-vancomycin, pH5; light line with X symbols); and GLU pH5.5 (2:1 ratio of GLU-vancomycin, pH5.5; light line with asterisk symbols).

A similar study conducted for samples at room temperature is presented in Table 13 and FIG. 12. Some of the amino acids that did not perform very well at 4° C. were much better in stabilizing vancomycin at room temperature. GABA, D-ALA, D-GLU, and ASP reduced degradation to about 0.2-0.4% per week, compared to about 1.4% per week in control. Thus, the stabilized glycopeptide antibiotic composition comprising amino acid or derivative thereof such as, for example, GABA, D-ALA, D-GLU, or ASP was about 71.4% to about 85.7% more stable at RT than a glycopeptide antibiotic that does not comprise an amino acid or derivative thereof.

TABLE 13

Degradation of vancomycin data table: Effect of amino acid additives at room temperature (RT).

| Sample | (CDPI-m + CDPI-M) % at week: | | | | | | Slope | Ratio |
|---|---|---|---|---|---|---|---|---|
| | 0 | 1 | 2 | 4 | 8 | 12 | %/w | Rt/4 C. |
| NaOHpH5 | 0.50 | 1.38 | 2.80 | 6.58 | 9.89 | 18.10 | 1.43 | 16.3 |
| b-ALA | 0.50 | 2.31 | 3.40 | 9.04 | 12.27 | 25.30 | 1.95 | 9.3 |
| ALA | 0.50 | 1.76 | 3.35 | 9.39 | 9.02 | 31.48 | 2.29 | 16.3 |
| GABApH5.5 | 0.50 | 2.20 | 3.18 | 4.23 | 4.44 | 6.44 | 0.41 | 5.0 |
| GLY | 0.50 | 1.56 | 3.24 | 6.14 | 17.19 | 21.04 | 1.85 | 14.0 |
| D-ALA | 0.50 | 1.35 | 1.61 | 1.73 | 2.49 | 3.56 | 6.22 | 3.3 |
| B-ABA | 0.50 | 1.51 | 3.03 | 6.03 | 9.23 | 19.28 | 1.48 | 10.1 |
| GLUt_NH3 | 0.50 | 1.54 | 5.20 | 4.05 | 7.42 | 10.22 | 0.71 | 6.1 |
| B-GLUt | 0.50 | 1.57 | 1.98 | 1.68 | 4.17 | 5.86 | 8.38 | 5.6 |
| ASP | 0.50 | 0.80 | 2.22 | 2.27 | 3.24 | 6.81 | 0.33 | 7.5 |
| B-ASP | 0.50 | 1.46 | 2.47 | 3.80 | 5.97 | 7.08 | 0.94 | 9.3 |
| Bicine | 0.50 | 0.89 | 1.47 | 3.21 | 6.26 | 10.96 | 8.89 | 89.4 |
| Tricine | 0.50 | 1.15 | 2.09 | 6.21 | 8.66 | 17.63 | 1.41 | 23.9 |

TABLE 13-continued

Degradation of vancomycin data table: Effect of amino acid additives at room temperature (RT).

| Sample | (CDPI-m + CDPI-M) % at week: | | | | | | Slope %/w | Ratio Rt/4 C. |
|---|---|---|---|---|---|---|---|---|
|  | 0 | 1 | 2 | 4 | 8 | 12 |  |  |
| Sarcosine | 0.54 | 1.17 | 2.33 | 6.48 | 11.47 |  | 1.44 | 19.8 |
| IDAA | 0.50 | 2.29 | 2.76 | 5.39 | 10.07 |  | 1.17 | 145 |
| GLY-GLY | 0.66 | 0.72 | 1.24 | 2.80 | 5.92 |  | 0.69 | 60.3 |

The ratio of the rate of conversion at room temperature (RT) to the rate at 4° C. is calculated in the last column in Table 13. This ratio varies dramatically, from 3.3 for D-ALA to 145 for IDAA. This could indicate that different AA affect differently the conversion reaction of vancomycin to CDP. Without being limited by theory, the rate could have changed through a change in activation energy, or through change in other factors such as the functional group orientation or the probability of collision.

One way to study those factors is to determine the rate of conversion at different temperatures and present the data in the form of an Arrhenius plot. An Arrhenius plot displays the logarithm of kinetic constants (ln(k), ordinate axis) plotted against inverse temperature (1/T, abscissa). For a single rate-limited thermally activated process, an Arrhenius plot gives a straight line from which the activation energy and the pre-exponential factor can both be determined.

The Arrhenius equation can be written as:

$$\ln(k) = \ln(A) - \frac{E_a}{R}\left(\frac{1}{T}\right)$$

where:

k=Rate constant
A=Pre-exponential factor
$E_a$=Activation energy
R=Gas constant
T=Absolute temperature, K When plotted in the manner described above, the value of the "y-intercept" will correspond to ln(A), and the gradient of the line will be equal to $-E_a/R$. The pre-exponential factor, A, is a constant of proportionality that takes into account a number of factors, such as the frequency of collision between and the orientation of the reacting particles.

TABLE 14

Degradation of vancomycin at number of different controlled temperatures.

| Sample | Temp | | | | | | Slope K | E kJ/mol | $R^2$ |
|---|---|---|---|---|---|---|---|---|---|
|  | 50 | 40 | 30 | 23 | 15 | 4 |  |  |  |
|  | $10^3/T$ | | | | | | | | |
|  | 3.10 | 3.19 | 3.30 | 3.38 | 3.47 | 3.61 |  |  |  |
| CDP-I rate %/week | | | | | | | | | |
| V_NaOH | 42.44 | 13.53 | 3.48 | 1.67 | 0.81 | 0.15 |  |  |  |
| V_Bicine2 | 28.88 | 4.91 | 1.01 | 0.40 | 0.14 | 0.01 |  |  |  |
| V_GLYGLY1 | 33.90 | 6.00 | 2.03 | 1.14 | 0.22 | 0.05 |  |  |  |
| V_GLYGLY1.5 | 25.78 | 3.69 | 1.57 | 0.87 | 0.23 | 0.04 |  |  |  |
| V_GLYGLY2 | 33.12 | 6.19 | 1.70 | 0.97 | 0.25 | 0.04 |  |  |  |
| V_GLU2 | 38.46 | 5.18 | 1.50 | 0.95 | 0.33 | 0.05 |  |  |  |
| Ln (CDP-I rate) | | | | | | | | | |
| V_NaOH | 3.75 | 2.60 | 1.25 | 0.51 | −0.21 | −1.92 | −10.8 | 89.7 | 0.99 |
| V_Bicine2 | 3.36 | 1.59 | 0.01 | −0.92 | −2.00 | −4.57 | −14.8 | 123 | 0.99 |
| V_GLYGLY1 | 3.52 | 1.79 | 0.71 | 0.13 | −1.52 | −3.06 | −12.5 | 104 | 0.99 |
| V_GLYGLY1.5 | 3.25 | 1.31 | 0.45 | −0.14 | −1.46 | −3.23 | −11.9 | 99 | 0.98 |
| V_GLYGLY2 | 3.50 | 1.82 | 0.53 | −0.03 | −1.39 | −3.32 | −12.8 | 106 | 0.99 |
| V_GLU2 | 3.65 | 1.64 | 0.40 | −0.06 | −1.11 | −3.07 | −12.2 | 102 | 0.98 |

Figure 13:
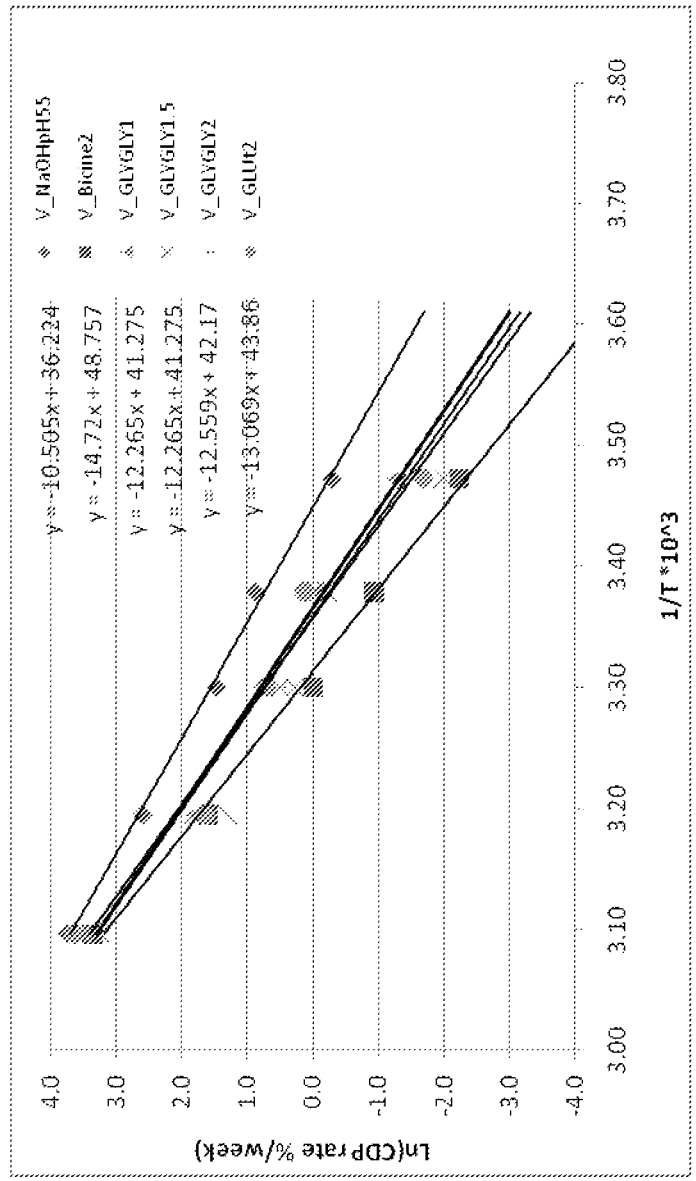
FIG. 13 shows an Arrhenius plot for vancomycin degradation rates based on Table 14. Vancomycin in NaOH at pH 5.5 (diamonds); Bicine-vancomycin in a 2:1 ratio (squares); GLY-GLY-vancomycin in a 1:1 ratio (triangles); GLY-GLY-vancomycin in a 1.5:1 ratio (Xs); GLY-GLY-vancomycin in a 2:1 ratio (asterisks); and GLU-vancomycin in a 2:1 ratio (circles).

For this evaluation vancomycin samples at 200 mg/mL and pH adjusted to pH 5.5 were used. From the slope of the fitted line on Arrhenius plot (FIG. 13), the activation energy for vancomycin to CDP conversion has been determined (Table 14). In a control sample with no amino acid, the activation energy was 89.7 kJ/ml. All tested amino acids increased activation energy, with Bicine leading to an increase of about 123 kJ/mol.

Example 3. Stability of Liposomal Vancomycin-Amino Acid Formulations

Figure 14:
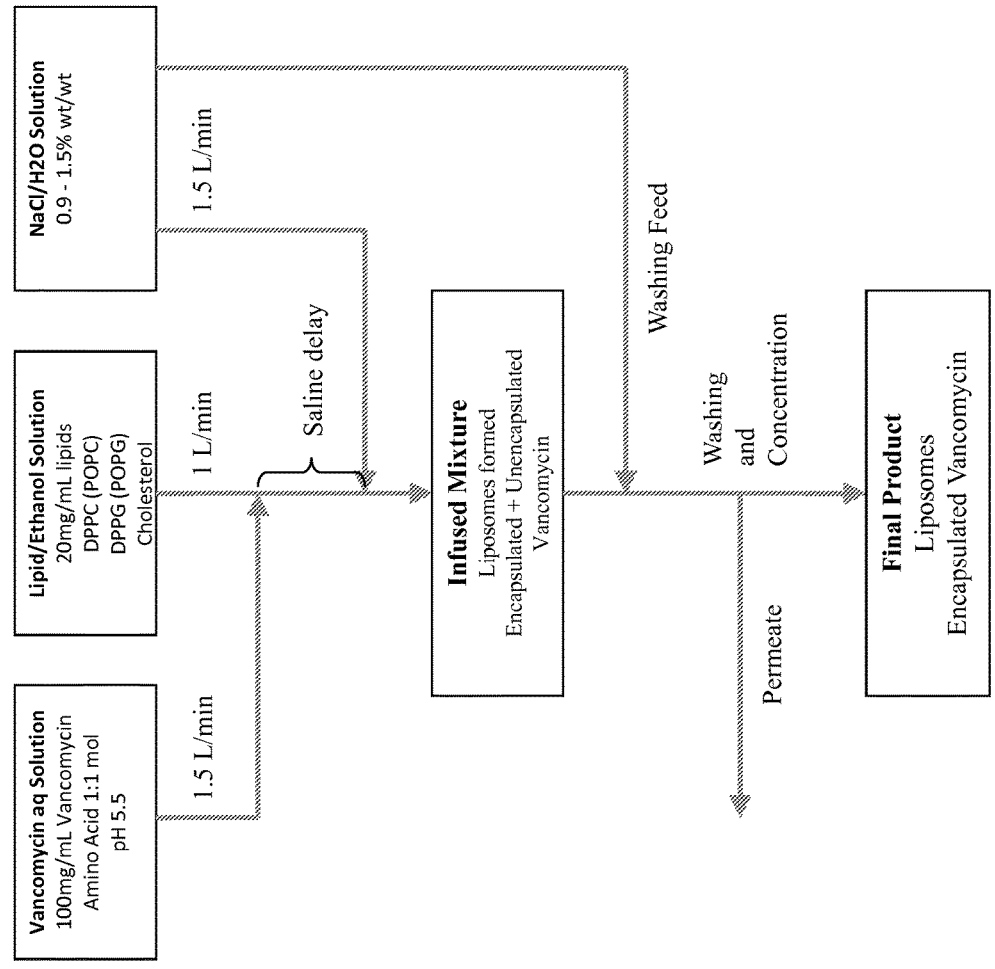
FIG. 14 shows a liposomal vancomycin infusion diagram (three stream infusion process).

Three formulations (see Table 15) of liposomal vancomycin were prepared using the 3-stream infusion process shown in FIG. 14.

TABLE 15

Composition of liposomal vancomycin batches used for stability study.

| Batch | AA | Lipid Composition | Washing NaCl |
|---|---|---|---|
| L-VGLUt0330 | GLU | DPPC/Chol (50:50 mol %) | 0.90% |
| L-VDGLUt0405 | D-GLU | DPPC/DPPG/Chol (47.5:5:47.5 mol %) | 1.50% |

TABLE 15-continued

Composition of liposomal vancomycin batches used for stability study.

| Batch | AA | Lipid Composition | Washing NaCl |
|---|---|---|---|
| LPG-VGLUto408 | GLU | DPPC/Chol (50:50 mol %) | 1.50% |

Liposomes were washed and concentrated to about 20 mg/mL lipid. The drug:lipid ratio was about 0.2. Approximately 1 mL each sample was incubated at 4° C. and at RT. Over time liposomes settled in the first two batches. Supernatant in those samples were analyzed for vancomycin as a measure of free vancomycin. Degradation of total vancomycin was measured after vortexing the sample and taking an aliquot of 10 µL.

Figure 15:
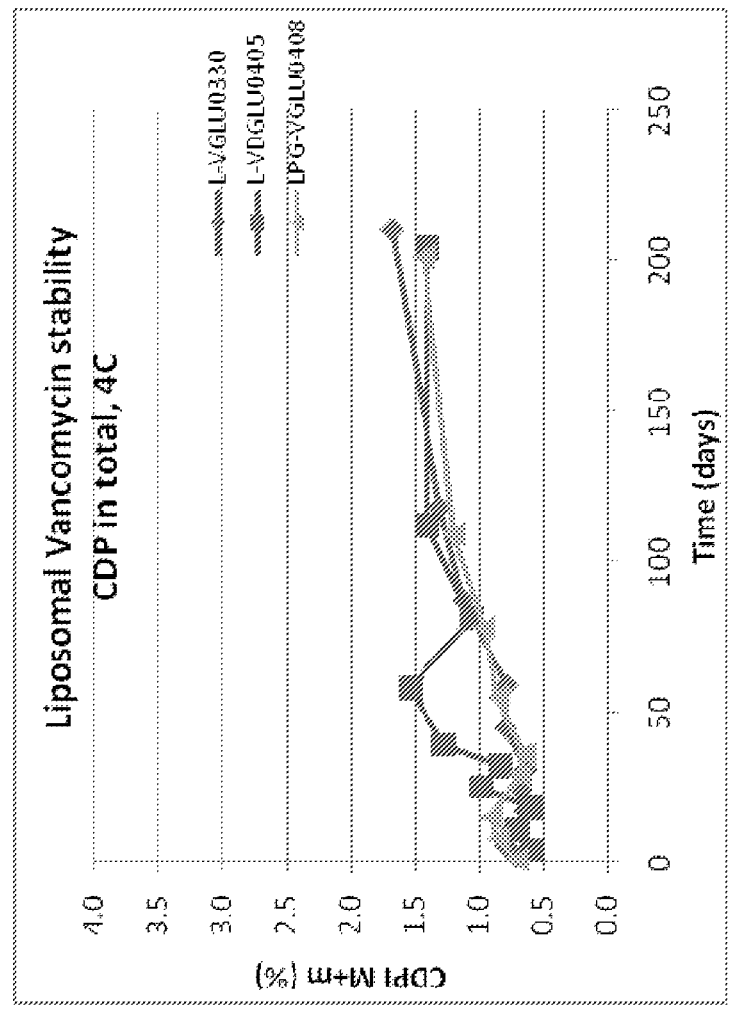
FIG. 15 is a graph of the stability over time of liposomal vancomycin-GLU compositions at 4° C. The batches of liposomal vancomycin compositions tested are those shown in Table 15 (i.e., diamonds correspond to L-VGLU0330, comprising GLU and DPPC/cholesterol; squares correspond to L-VDGLU0405, comprising D-GLU and DPPC/DPPG/cholesterol; and triangles correspond to LPG-VGLU0408, comprising GLU and DPPC/cholesterol).
Figure 16:
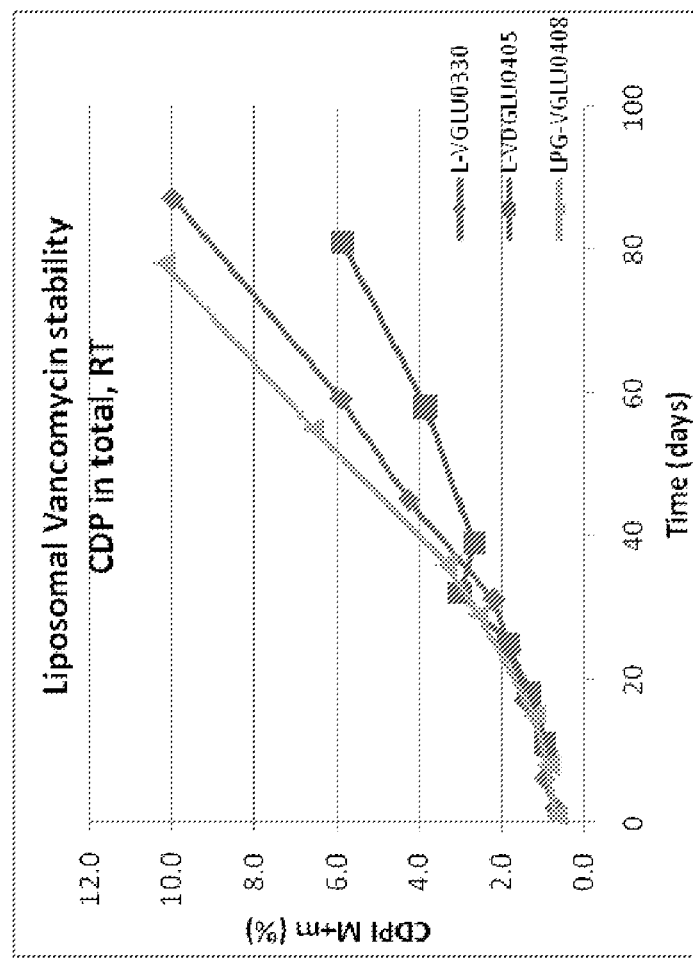
FIG. 16 is a graph of the stability over time of liposomal vancomycin-GLU compositions at RT. The batches of liposomal vancomycin compositions tested are those shown in Table 15 (i.e., diamonds correspond to L-VGLU0330, comprising GLU and DPPC/cholesterol; squares correspond to L-VDGLU0405, comprising D-GLU and DPPC/DPPG/cholesterol; and triangles correspond to LPG-VGLU0408, comprising GLU and DPPC/cholesterol).

The data are presented in Table 16 and FIGS. 15 and 16. From this limited incubation time one can see that vancomycin stability inside liposomes is comparable or better than in a solution of vancomycin with GLU added. For example, the rate for vancomycin-GLU (1:1) was 0.12% per week (Table 11), compared to 0.025 to 0.035% per week (Table 16) when encapsulated in liposomes.

Figure 17:
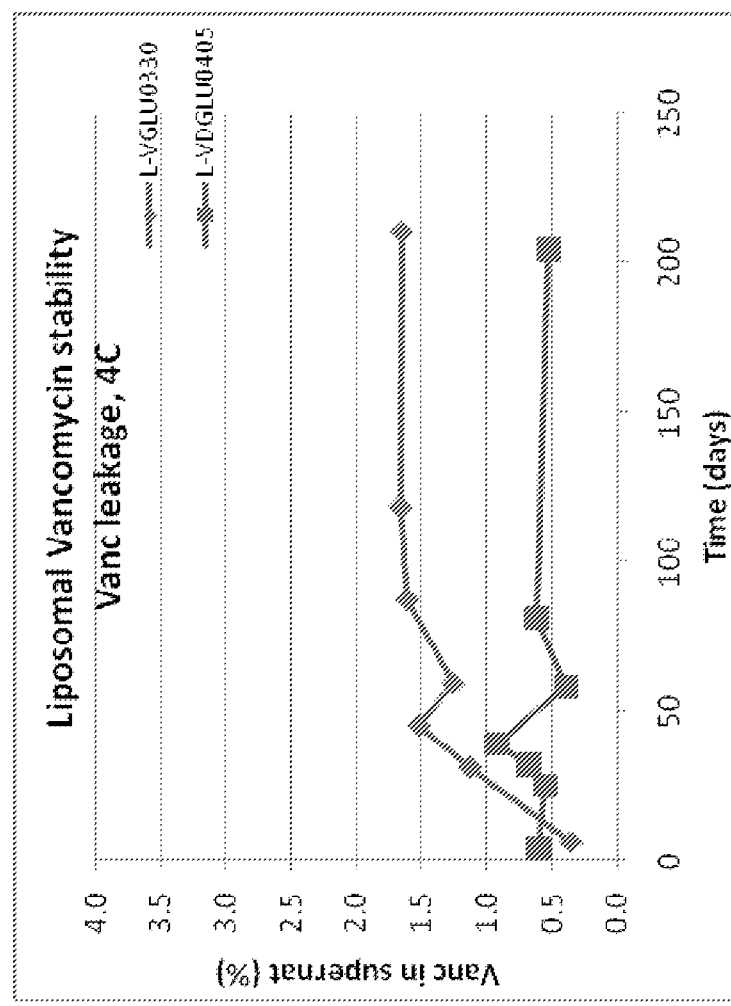
FIG. 17 is a graph of stability over time of liposomal vancomycin-GLU compositions at 4° C. The batches of liposomal vancomycin compositions tested are those shown in Table 15 (i.e., diamonds correspond to L-VGLU0330, comprising GLU and DPPC/cholesterol; and squares correspond to L-VDGLU0405, comprising D-GLU and DPPC/DPPG/cholesterol).
Figure 18:
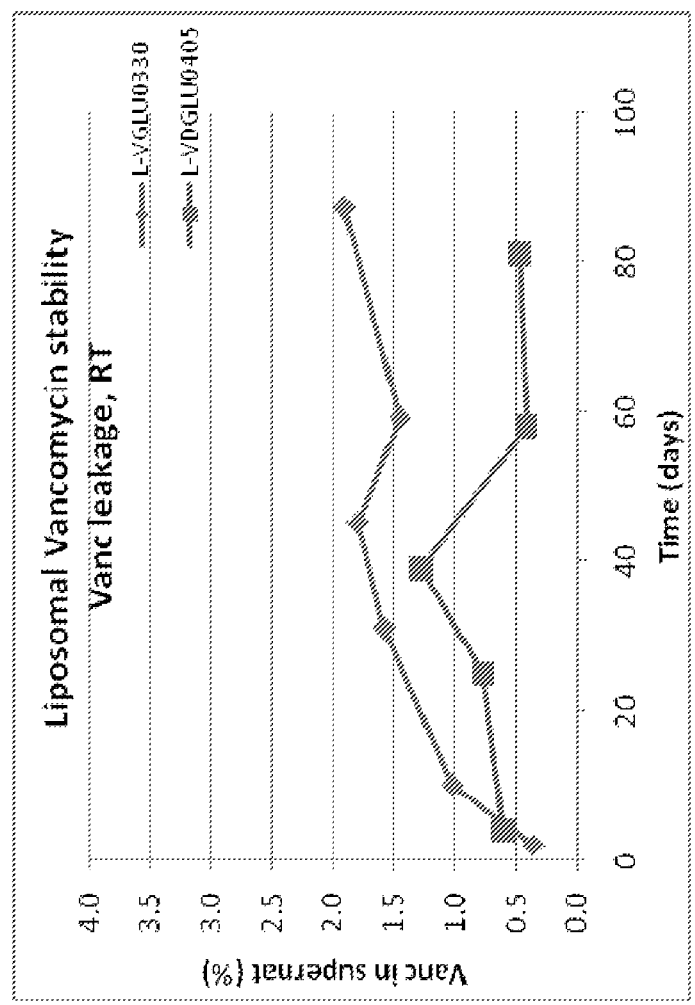
FIG. 18 is a graph of stability over time of liposomal vancomycin-GLU compositions at RT. The batches of liposomal vancomycin compositions tested are those shown in Table 15 (i.e., diamonds correspond to L-VGLU0330, comprising GLU and DPPC/cholesterol; and squares correspond to L-VDGLU0405, comprising D-GLU and DPPC/DPPG/cholesterol).

In addition, an estimate of free vancomycin based on the vancomycin level in supernatant indicates modest or low leak at 4° C. and at RT (FIGS. 17 and 18, respectively). Thus, the stabilized lipid-based glycopeptide antibiotic compositions of the present invention are unexpectedly more stable in comparison to glycopeptide antibiotic compositions that are not lipid-based and/or do not comprise an amino acid or derivative thereof.

TABLE 16

Degradation rates of vancomycin-GLU inside liposomes

| Batch | Degradation rate, %/w 4° C. | RT |
|---|---|---|
| L-VGLU0330 | 0.035 | 0.76 |
| L-VDGLU0405 | 0.028 | 0.47 |
| LPG-VGLU0408 | 0.025 | 0.89 |

In summary, the data indicate that the addition of amino acids and their derivatives remarkably affected the degradation rate of vancomycin. The most promising amino acids were Bicine, Imino-diacetic acid (IDAA), glycylglycine (GLY-GLY), and GLU (when used at 2:1 mol ratio with vancomycin). At 4° C., degradation rates as low as 0.01% per week were observed. Arrhenius plots for degradation in the presence of key amino acids could be fitted well to a linear function. The data suggested that improvement in stability is caused by an increase in activation energy value from 87 kJ/mol to up to 120 kJ/mol. Furthermore, encapsulation in liposomes of the vancomycin-amino acid compositions exhibited superior chemical stability.

Example 4. Stability of Liposomal Glycopeptide Antibiotic-Amino Acid Formulations Formulations of liposomal glycopeptide antibiotic comprising teicoplanin, telavancin, oritavancin, decaplanin or dalbavancin are prepared using the 3-stream infusion process shown in FIG. 14. Lipid components in the formulations comprise DPPC, DPPC+cholesterol, DPPG, DPPG+cholesterol, DPPC+DPPC+cholesterol, or POPC. Amino acid components in the formulations comprise Bicine, GLU, GLY-GLY, IDAA, ASP, or D-ALA.

Liposomes are washed and concentrated to about 20 mg/mL lipid. Approximately 1 mL each sample is incubated at 4° C. and at RT. To assess the stability of the glycopeptide antibiotic in the formulation, supernatant is analyzed for free glycopeptide antibiotic. Degradation of total glycopeptide antibiotic is measured after vortexing the sample and taking an aliquot of 10 µL.

All publications, protocols, patents and patent applications cited herein are incorporated herein by reference in their entireties for all purposes.

While the described invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the invention. All such modifications are intended to be within the scope of the claims appended hereto.

The invention claimed is:

1. A stabilized lipid-based glycopeptide antibiotic composition comprising:
    a lipid component;
    a glycopeptide antibiotic component; and
    an amino acid or derivative thereof,
    wherein the amino acid or the derivative thereof reduces the degradation rate of the glycopeptide antibiotic, and wherein the antibiotic composition is at least 44% more stable than an antibiotic composition comprising the same lipid component and the same glycopeptide antibiotic component, that does not comprise an amino acid or a derivative thereof.

2. The stabilized lipid-based glycopeptide antibiotic composition according to claim 1, wherein the stabilized glycopeptide antibiotic-amino acid complex is entrapped by the lipid component.

3. The stabilized lipid-based glycopeptide antibiotic composition according to claim 1, wherein the antibiotic composition is at least 77% more stable, or at least 88% more stable, than an antibiotic composition comprising the same lipid component and the same glycopeptide antibiotic component, that does not comprise an amino acid or a derivative thereof.

4. The stabilized lipid-based glycopeptide antibiotic composition according to claim 1, wherein the composition produces product degradants at a rate less than 0.05% by weight per week at 4° C., or a rate less than 0.02% by weight per week at 4° C., or a rate less than 0.01% by weight per week at 4° C.

5. The stabilized lipid-based glycopeptide antibiotic composition according to claim 1, wherein the lipid component comprises a phospholipid.

6. The stabilized lipid-based glycopeptide antibiotic composition according to claim 5, wherein the phospholipid is selected from the group consisting of phosphatidylcholine (PC), phosphatidylglycerol (PG), phosphatidylinositol (PI), phosphatidylserine (PS), phosphatidylethanolamine (PE), phosphatidic acid (PA), and a mixture thereof.

7. The stabilized lipid-based glycopeptide antibiotic composition according to claim 1, wherein the lipid component comprises a sterol.

8. The stabilized lipid-based glycopeptide antibiotic composition according to claim 7, wherein the sterol is cholesterol.

9. The stabilized lipid-based glycopeptide antibiotic composition according to claim 1, wherein the lipid component comprises a phospholipid and a sterol.

10. The stabilized lipid-based glycopeptide antibiotic composition according to claim 1, wherein the lipid component comprises dipalmitoylphosphatidylcholine (DPPC).

11. The stabilized lipid-based glycopeptide antibiotic composition according to claim 1, wherein the lipid component comprises dipalmitoylphosphatidylcholine (DPPC) and cholesterol.

12. The stabilized lipid-based glycopeptide antibiotic composition according to claim 1, wherein the lipid component comprises dipalmitoylphosphatidylglycerol (DPPG).

13. The stabilized lipid-based glycopeptide antibiotic composition according to a claim 1, wherein the lipid component comprises dipalmitoylphosphatidylglycerol (DPPG) and cholesterol.

14. The stabilized lipid-based glycopeptide antibiotic composition according to claim 1, wherein the lipid component comprises dipalmitoylphosphatidylcholine (DPPC), dipalmitoylphosphatidylglycerol (DPPG), and cholesterol.

15. The stabilized lipid-based glycopeptide antibiotic composition according to claim 2, wherein the lipid component is a liposome, a lipid clathrate or a proliposome.

16. The stabilized lipid-based glycopeptide antibiotic composition according to claim 1, wherein the glycopeptide antibiotic is vancomycin.

17. The stabilized lipid-based glycopeptide antibiotic composition according to claim 1, wherein the amino acid is D-alanine, aspartic acid, bicine, D-glutamic acid, glycylglycine (Gly-Gly) or iminodiacetic acid.

18. The stabilized lipid-based glycopeptide antibiotic composition according to claim 1, wherein a molar ratio of the glycopeptide antibiotic component to the amino acid or derivative thereof is from about 1:1 to about 1:4, from about 1:1 to about 1:2, about 1:1 or about 1:2.

19. The stabilized lipid-based glycopeptide antibiotic composition according to claim 1, wherein the composition comprises an amino acid or derivative thereof is a dipeptide or a tripeptide.

20. A method for treating a bacterial infection in a patient in need thereof, the method comprising administering to the patient, a therapeutically effective amount of a stabilized lipid-based glycopeptide antibiotic composition comprising a lipid component, a glycopeptide antibiotic component, and an amino acid or derivative thereof, wherein the amino acid or the derivative thereof reduces the degradation rate of the glycopeptide antibiotic, and wherein the antibiotic composition is at least 44% more stable than an antibiotic composition comprising the same lipid component and the same glycopeptide antibiotic component, that does not comprise an amino acid or a derivative thereof.

* * * * *